United States Patent
Griffith et al.

(10) Patent No.: US 12,054,511 B2
(45) Date of Patent: *Aug. 6, 2024

(54) SYNTHESIS OF PHOSPHATE DERIVATIVES

(71) Applicant: NuCana plc, Central Scotland (GB)

(72) Inventors: Hugh Griffith, Central Scotland (GB); Gordon Kennovin, Central Scotland (GB); Venkata Lakshmi Narasimha Rao Dammalapati, Hyderabad (IN); Mani Bushan Kotala, Hyderabad (IN)

(73) Assignee: NuCana plc, Edinburgh (GB)

( * ) Notice: Subject to any disclaimer, the term of this patent is extended or adjusted under 35 U.S.C. 154(b) by 32 days.

This patent is subject to a terminal disclaimer.

(21) Appl. No.: 17/888,312

(22) Filed: Aug. 15, 2022

(65) Prior Publication Data

US 2022/0402962 A1    Dec. 22, 2022

Related U.S. Application Data

(63) Continuation of application No. 16/623,263, filed as application No. PCT/GB2018/051638 on Jun. 14, 2018, now Pat. No. 11,414,452.

(30) Foreign Application Priority Data

Jun. 14, 2017   (GB) .................................... 1709471

(51) Int. Cl.
   *C07H 19/207*    (2006.01)
   *C07H 1/02*      (2006.01)
   *C07H 19/10*     (2006.01)
   *C07H 19/20*     (2006.01)

(52) U.S. Cl.
   CPC ............ *C07H 19/207* (2013.01); *C07H 1/02* (2013.01); *C07H 19/10* (2013.01); *C07H 19/20* (2013.01)

(58) Field of Classification Search
   None
   See application file for complete search history.

(56) References Cited

U.S. PATENT DOCUMENTS

| | | |
|---|---|---|
| 6,245,750 B1 | 6/2001 | Shepard |
| 6,683,061 B1 | 1/2004 | Shepard et al. |
| 7,462,605 B2 | 12/2008 | Shepard et al. |
| 7,608,599 B2 | 10/2009 | Klumpp et al. |
| 7,964,580 B2 | 6/2011 | Sofia et al. |
| 8,263,575 B2 | 9/2012 | McGuigan et al. |
| 8,618,076 B2 | 12/2013 | Ross et al. |
| 8,642,756 B2 | 2/2014 | Ross et al. |
| 8,658,616 B2 | 2/2014 | McGuigan et al. |
| 8,759,318 B2 | 6/2014 | Chamberlain et al. |
| 8,841,275 B2 | 9/2014 | Du et al. |
| 8,859,756 B2 | 9/2014 | Du et al. |
| 8,871,737 B2 | 10/2014 | Smith et al. |
| 8,933,053 B2 | 1/2015 | McGuigan et al. |
| 9,090,642 B2 | 7/2015 | Cho et al. |
| 9,221,866 B2 | 12/2015 | McGuigan et al. |
| 9,278,990 B2 | 3/2016 | Smith et al. |
| 9,365,605 B2 | 6/2016 | Beigelman et al. |
| 9,487,544 B2 | 11/2016 | Cho et al. |
| 9,655,915 B2 | 5/2017 | McGuigan et al. |
| 9,815,864 B2 | 11/2017 | Beigelman et al. |
| 9,834,577 B2 | 12/2017 | Dammalapati et al. |
| 9,862,743 B2 | 1/2018 | Beigelman et al. |
| 10,005,810 B2 | 6/2018 | McGuigan et al. |
| 10,022,390 B2 | 7/2018 | McGuigan et al. |
| 10,538,541 B2 | 1/2020 | Yuan et al. |
| 10,660,912 B2 | 5/2020 | Griffith |
| 10,662,213 B2 | 5/2020 | Griffith et al. |
| 10,669,300 B2 | 6/2020 | Griffith |
| 10,689,413 B2 | 6/2020 | Yuan et al. |
| 10,774,104 B2 | 9/2020 | Kotala et al. |
| 10,786,523 B2 | 9/2020 | Griffith et al. |
| 2010/0249068 A1 | 9/2010 | Beigelman et al. |
| 2012/0070411 A1 | 3/2012 | Beigelman et al. |
| 2018/0237466 A1 | 8/2018 | Yuan et al. |
| 2018/0369266 A1 | 12/2018 | Kennovin et al. |
| 2019/0022117 A1 | 1/2019 | Griffith |
| 2019/0374564 A1 | 12/2019 | Griffith et al. |
| 2020/0181189 A1 | 6/2020 | Griffith et al. |
| 2021/0100825 A1 | 4/2021 | Griffith et al. |

FOREIGN PATENT DOCUMENTS

| | | |
|---|---|---|
| CN | 105646629 A | 6/2016 |
| DE | 279248 A1 | 5/1990 |
| GB | 1377027 A | 12/1974 |
| WO | WO 2012/040127 A1 | 9/2010 |
| WO | WO 2010/135569 A1 | 11/2010 |

(Continued)

OTHER PUBLICATIONS

CommonOrganicChemistry.com, TEA (Triethylamine), internet article published Oct. 20, 2014, https://web.archive.org/web/20141020041711/https://www.commonorganicchemistry.com/Common_Reagents/Triethylamine/Triethylamine.htm. (Year: 2014).*

Agarwal RP., Han T., Fernandez M., Collateral resistance of a dideoxycytidine-resistant cell line to 5-fluoro-2'-deoxyuridine. Biochem. Biophys. Res. Commun. 1999; 262:657-60.

Antúnez, Carmen J., "Design, Synthesis and Biological Evaluation of Nucleoside Phosphoramidates with potential Anticancer Activity," A Thesis submitted for the degree of Philosophiae Doctor in Cardiff University, Jan. 2017; 269 pages.

Ayusawa D., Koyama H., Iwata K., Seno T., Single-step selection of mouse FM3A cell mutants defective in thymidylate synthetase. Somatic Cell Genet. 1980; 6:261-70.

(Continued)

*Primary Examiner* — Layla D Berry
(74) *Attorney, Agent, or Firm* — Knowles Intellectual Property Strategies, LLC

(57) ABSTRACT

The present invention is a process for the preparation of certain 5'-phosphoramidate nucleotide diastereoisomers. The phosphoramidates include those useful in the treatment of cancer such as NUC-3373 (5-fluoro-2'-deoxyuridine-5'-O-[1-naphthyl(benzyloxy-L-alaninyl)]phosphate].

26 Claims, No Drawings

(56) References Cited

FOREIGN PATENT DOCUMENTS

| WO | WO 2011/123672 A1 | 10/2011 |
|---|---|---|
| WO | WO 2012/040126 A1 | 3/2012 |
| WO | WO 2012/117246 A1 | 9/2012 |
| WO | WO 2015/081133 A1 | 6/2015 |
| WO | WO 2016/012781 A1 | 1/2016 |
| WO | WO 2016/181093 A1 | 11/2016 |
| WO | WO 2017/109491 A1 | 6/2017 |
| WO | WO 2017/207993 A1 | 12/2017 |
| WO | WO 2019/043392 A1 | 3/2019 |

OTHER PUBLICATIONS

Ayusawa D., Koyama H., Seno T., Resistance to methotrexate in thymidylate synthetase-deficient mutants of cultured mouse mammary tumor FM3A cells. Cancer Res. 1981; 41: 1497-501.
Balzarini J. et al.; "Role of thymidine kinase in the inhibitory activity of 5-substituted-2'-deoxyuridines on the growth of human and murine tumor cell lines." Biochem Pharmacol. 1982: 31: 1089-1095.
Balzarini J. et al.; Strategies for the measurement of the inhibitory effects of thymidine analogs on the activity of thymidylate synthase in intact murine leukemia L1210 cells. Biochem. Biophys Acta 1984; 785:36-45.
Balzarini, J. et al., "Mechanism of anti-HIV action of masked alaninyl d4T-MP derivatives," Proc. Natl. Acad. Sci. U.S.A. 1996, 93, pp. 7295-7299.
Beck A., et al.; "A role for dihydropyrimidine dehydrogenase and thymidylate synthase in tumour sensitivity to fluorouracil." Eur J Cancer 1994; 30A:1517-22.
Birkus, G. et al., "Cathepsin A is the major hydrolase catalyzing the intracellular hydrolysis of the antiretroviral nucleotide phosphonoamidate prodrugs GS-7340 and GS-9131," Antimicrob. Agents Chemother. 2007, 51, pp. 543-550.
Blanka Gönczy; "Design, Synthesis and Biological Evaluation of Nucleotide Pro-drugs Centred on Clinically Active Anticancer Nucleosides," Thesis of Cardiff School of Pharmacy and Pharmaceutical Sciences Cardiff University; 2016.
Bronckaers A., Balzarini I., Liekens S., The cytostatic activity of pyrimidine nucleosides is strongly modulated by Mycoplasma hyorhinis infection: Implications for cancer therapy. Biochem Pharmacol 2008; 76: 188-97.
Bronckaers A., Gago F., Balzarini J., Liekens S., The dual role of thymidine phosphorylase in cancer development and chemotherapy. Med Res Rev 2009; 29:903-53.
Cahard, D. et al., "Aryloxy Phosphoramidate Triesters as Pro-Tides," Mini-Reviews in Medicinal Chemistry, 2004, 4, DD. 371-382.
CAS Abstract accession No. 1997:432895 of Drug Design and Discovery 1995 vol. 13 (1) Nillroth et al pp. 43-54.
CAS Abstract accession No. 1995:297145 of Antiviral Chemistry & Chemotherapy, 1995, vol. 6(1), Nillroth et al., pp. 50-64.
Chan P.J. et al. Prevalence of mycoplasma conserved DNA in malignant ovarian cancer detected using sensitive PCR-ELISA Gynecol Oncol 1996;63:258-60.
Charron J. and Langelier Y, Analysis of deoxycytidine (dC) deaminase activity in herpes simplex vims-infected or HSV TK-transformed cells: association with mycoplasma contamination but not with vims infection. J Gen Virol 1981; 57:245-50.
Ciaparrone M. et al.; Predictive role of thymidylate synthase, dihydropyrimidine dehydrogenase and thymidine phosphorylase expression in colorectal cancer patients receiving adjuvant 5-fluorouracil. Oncology 2006; 70:366-77.
Ciccolini J. et al.; Thymidine phosphorylase and fluoropyrimidines efficacy: a Jekyll and Hyde story. Curr Med Chem Anticancer Agents 2004; 4:71-81.
Congiatu, C. et al.; "Design, Synthesis and Biological Evaluation of Some Novel Nucleotide Prodrugs as Potential Anticancer Agents," Nucleosides, Nucleotides and Nucleic Acids (2005) 24:5-7, 485-489.
Congiatu C. et al.; Novel potential anticancer naphthyl phosphoramidates of BVdU: separation of diastereoisomers and assignment of the absolute configuration of the phosphorus center. J. Med. Chem. 2006; 49:452-455.
Congiatu, Costantino; et al., "Design, Synthesis and Biological Evaluation of Some Novel Nucleotide Prodrugs as Potential Anticancer Agents," A Thesis submitted to the University of Wales for the Degree of Philosophiae Doctor, 2006; pp. 1-290.
Dang, Q. et al., "Discovery of Potent and Specific Fructose-1,6-Bisphosphatase Inhibitors and a Series of Orally-Bioavailable Phosphoramidase-Sensitive Prodrugs for the Treatment of Type 2 Diabetes," J. Am. Chem. Soc. 2007,129, pp. 15491-15502.
De Bruin M. et al.; Role of platelet derived endothelial cell growth factor thymidine phosphorylase in fluoropyrimidine sensitivity and potential role of deoxyribose-1-phosphate. Nucleosides Nucleotides Nucleic Acids 2004; 23:1485-90.
Derudas, M. et al., "The Application of Phosphoramidate Protide Technology to Acyclovir Confers Anti-HIV Inhibition," J. Med. Chem. 2009, 52, pp. 5520-5530.
English Abstract for DD279248 published Aug. 20, 1996, WPI Accession No. 1990-327965 [199044].
Ensminger, W.D., et al., "Clinical Pharmacology of Hepatic Arterial Chemotherapy," Seminars in Oncology, vol. 10. No. 2, pp. 176-182, Jun. 1983.
Ferrari, Valentina; "Synthesis and Biological Evaluation of Novel Nucleosides and Nucleotides as Potential Therapeutic Agents," A Thesis submitted in accordance with the conditions governing candidates for the degree of Philosophiae Doctor in Cardiff University, Sep. 2015; 409 pages.
Galmarini C.M. et al.; Nucleoside analogues and nucleobases in cancer treatment. Lancet Oncol 2002; 3:415-24.
Golub et al., Molecular Classification of Cancer: Class Discovery and Class Prediction by Gene Expression Monitoring, Science (1999), vol. 286, 531-537.
Grem, J. L., "5-Fluorouracil: forty-plus and still ticking. A review of its preclinical and clinical development," Invest. New Drugs 2000, 18, pp. 299-313.
Harris S.A., et al.; "Synthesis and antiviral evaluation of phosphoramidate derivatives of (E)-5-(2-bromovinyl)-2'deoxyuridine," Antiviral Chemistry & Chemotherapy, 2002, 12:293-300.
Hatse S., De C.E., Balzarini J., Role of antimetabolites of purine and pyrimidine nucleotide metabolism in tumor cell differentiation. Biochem Phannacol 1999; 58:539-55.
Hecker S.J. and Erion M.D., Prodrugs of phosphates and phosphonates. J. Med. Chem. 2008; 51:2328-45.
Heidelberger, C., et al., "Fluorinated Pyrimidines, A New Class of Tumour-Inhibitory Compounds"; Nature 1957 pp. 663-666.
Holland, J. F .; Frei, E .; Pizzomo, G .; Diasio, R. B.; Cheng, Y. C.: "Cancer Medicine" 7th Ed. BC Decker: Hamilton, Ontario, Canada, 2006.
Homsi, J. et al., "Hepatic arterial infusion of chemotherapy for hepatic metastases from colorectal cancer," Cancer Control 2006, 13, pp. 42-47.
Huang S., Li J.Y., Wu I., Meng L., Shou CC., Mycoplasma infections and different human carcinomas. World J Gastroenterol 2001; 7:266-9.
International Search in International Application PCT/GB2012/050457, dated Apr. 19, 2012; 5 pages.
Written Opinion in International Application PCT/GB2012/050457, dated Sep. 1, 2013; 6 pages.
International Preliminary Report on Patentability in International Application PCT/GB2012/050457, dated Sep. 3, 2013; 7 pages.
International Search Report in International Application PCT/GB2011/001446, dated Jan. 26, 2012; 4 Pages.
Ishikawa, Tohru, et al., Tumor selective delivery of 5-Fluorouracil by Capecitabine, aNew Oral Fluoropyrimidine Carbamate, in Human Cancer Xenografts, Cytostatics Group, Nippon Roche Research Center, Kamaxura-City, Kanagawa 247. Japan, Biochemical Pharmacology, vol. 55, pp. 1091-1097 (1998).
Jette L. et al.; Resistance of colorectal cancer cells to 5-FUdR and 5-FU caused by Mycoplasma infection. Anticancer Res 2008; 28:2175-80.

(56) References Cited

OTHER PUBLICATIONS

Jones, B. C et al., "Synthesis and anti-HIV activity of some novel phosphorodiamidate derivatives of 3'-asido-3'-deoxythymidine (AZT)," Antiviral Chemistry & Chemotherapy (1991) 2(1) pp. 35-39.
Kamoshida S., et al.; Immunohistochemical demonstration of fluoropyrimidine-metabolizing enzymes in various types of cancer. Oncol Rep. 2005.14: 1223-30.
Kidder M., Chan P.I., Seraj 1,M., Patton W,C., King "A Assessment of archived paraffin-embedded cervical condyloma tissues for mycoplasma-conserved DNA using sensitive PCR-ELISA," Gynecol Oncol 1998; 71:254-257.
Kinsella A. Rand Smith D., Tumor resistance to anti metabolites. Gen Pharmacol 1998; 30:623-6.
Koopman M. et al.; A review on the use of molecular markers of cytotoxic therapy for colorectal cancer, what have we learned? Eur J Cancer 2009; 45: 1935-49.
Kosaka T. et al.; Effects of thymidine phosphorylase levels in cancer, background mucosa, and regional lymph nodes on survival of advanced gastric cancer patients receiving postoperative fluoropyrimidine therapy. Oncol Rep 2004; 12:1279-86.
Lala et al., Role of nitric oxide in tumor progression: Lessons from experimental tumors, Cancer and Metastasis Reviews (1998), 17, 91-106.
Lackey et al., Enzyme-catalyzed therapeutic agent (ECTA) design: activation of the antitumor ECTA compound NB1011 by thymidylate synthase, Biochemical Pharmacology 61 (2001) pp. 179-189.
Lee, W. A. et al., "Selective intracellular activation of a novel prodrug of the human immunodeficiency virus reverse transcriptase inhibitor tenofovir leads to preferential distribution and accumulation in lymphatic tissue," Antimicrob Agents Chemother. 2005, 49, pp. 1898-1906.
Liekens S. et al.; Improvement of purine and pyrimidine antimetabolite-based anticancer treatment by selective suppression of mycoplasma-encoded catabolic enzymes. Lancet Oncol. 2009; 10:628-35.
Longley D.B. et al.; 5-fluorouracil: mechanisms of action and clinical strategies. Nat Rev Cancer 2003; 3:330-8.
Malet-Martino, M. et al., "Clinical studies of three oral prodrugs of 5-fluorouracil (capecitabine, UFT, S-1): a review," Oncologist, 2002, 7, pp. 288-323.
McGuigan, C. et al.; Phosphoramidate derivatives of d4T as inhibitors of HIV: The effect of amino acid variation. Antiviral Res. 1997, 35, 195.
McGuigan, Christopher et al.; Anti-cancer ProTides: tuning the activity of BVDU phosphoramidates related to thymectacin, Bioorganic & Medicinal Chemistry, 2005, vol. 13(2005) pp. 3219-3227.
McGuigan, C. et al.; "Design, synthesis and evaluation of a novel double pro-drug: INX-08189. A new clinical candidate for hepatitis C virus," Bioorg. Med. Chem. Lett. 2010, 20 pp. 4850-4854.
McGuigan, C. et al.; "Application of Phosphoramidate Pronucleotide Technology to Abacavir Leads to a Significant Enhancement of Antiviral Potency," J. Med. Chem. 2005, 48, pp. 3504-3515.
McGuigan, C. et al.; "Aryl phosphoramidate derivatives of d4T have improved anti-HIV efficacy in tissue vulture and may act by the generation of a novel intracellular metabolite," J. Med. Chem. 1996, 39, 1748-1753.
McGuigan, C. et al.; "Intracellular delivery of bioactive AZT nucleotides by aryl phosphate derivatives of AZT," Med. Chem. 1993; 36, 1048-1052.
McGuigan Christopher et al.; "Phosphoramidate ProTides of 2'-C-methylguanosine as highly potent inhibitors of hepatitis C virus. Study of their in vitro and in vivo properties", J Med Chem 2010; 53:4949-57.
Mehellou, Y. et al.; Phosphoramidates of 2'-β-D-arabinouridine (AraU) as phosphate prodrugs: design, synthesis, in vitro activity and metabolism. Bioorg. Med. Chem. 2010, 18, 2439.
Mehellou, J. et al.; Aryloxy phosphoramidate triesters: a technology for delivering mono-phosphorylated nucleosides and sugars into cells, Chem. Med. Chem., 2009, 4, 11, 1779.

Mehellou, Y. et al. "The Protide Prodrug Technology: From the Concept to the Clinic," J. Med. Chem. 2018, 61, 2211-2226.
Moertel C.G., Chemotherapy for colorectal cancer. N Engl J Med 1994; 330:1136-42.
Murakami Y., et al.; Different mechanisms of acquired resistance to fluorinated pyrimidines in human colorectal cancer cells. Int J Oncol, 2000; 17:277-83.
Neale G.A. et al.; Enzymes of pyrimidine deoxyribonucleotide metabolism in Mycoplasmamycoides subsp. mycoides. J Bacteriol 1983; 156:1001-5.
Nillroth et al. "Specific interaction between HIV-1 proteinase and 5'-phosphate peptidomimetic derivatives of nucleoside analogs," Drug Design and Discovery 1995 vol. 13(1) pp. 43-54.
Nillroth et al., "The use of 5'-phosphate derivatives of nucleoside analogues as inhibitors of HIV-1 replication," Antiviral Chemistry & Chemotherapy 1995 vol. 6(1), pp. 50-64.
Noyori et al.; "Condensation of 1-Fluorofuranoses and Silylated Nucleobases Catalyzed by Tetrafluorosilane#," Chemistry Letters, 16(1): 57-60 (1987).
Okajchi Tatsuo et al., "Stereoselective Synthesis of β-2-Deoxyribonucleosides from 1-O-Acetyl-3-O-[2-(methylsulfinyl)ethyl]-2-deoxyribose" Chemistry Letters, 18(5): 801-804 (1989).
Parker, W. B., "Enzymology of purine and pyrimidine antimetabolites used in the treatment of cancer," Chem. Rev. 2009, 109, pp. 2880-2893.
Pegram, M. et al., "Enzyme-Catalyzed Therapeutic Activation (ECTA) NB1011 (Thymectacin TM) selectively targets thymidylate synthase (TS)-overexpressing tumor cells: preclinical and phase I, clinical results," Eur. J. Cancer 2002, 38 (Suppl. 7) S34.
Pehlivan M., Pehlivan S., Onay H., Koyuncuoglu M., Kirkali Z, Can Mycoplasma-mediated oncogenesis be responsible for formation of conventional renal cell carcinoma? Urology 2005; 65:411-414.
Pehlivan, M. et al., "Does *Mycoplasma* sp. play role in small cell lung cancer?"; Lung Cancer 2004, 45, pp. 129-130.
Pertusati et al.; "Diastereoselective synthesis of P-chirogenic phosphoramidate prodrugs of nucleoside analogues (ProTides) via copper catalyzed reaction," Chemical Communications, 51(38):8070-8073 (2015).
Peters, G.J. and Kohne C.H., "Resistance to anti metabolites. In: Fluoropyrimidines as Antifolate Drugs in Cancer Therapy," Jackman AL (ed). Humana Press Inc. 20 1999; pp. 101-145.
Quintiliani, et al. "Design, synthesis and biological evaluation of 2'-deoxy-2',2'-difluoro-5-halouridine phosphoramidate ProTides" Bioorg Med Chem, 19(14):4338- 4345 (2011).
Razin S., The mycoplasmas. Microbiol Rev 1978; 42:414-70.
Razin S., Yogev D., Naot Y, Molecular biology and pathogenicity of Mycoplasmas. Microbiol Mol Biol. Rev 1998; 62:1094-1156.
Roman, Cristina Arbelo; et al., "Synthesis of Aryloxy Phosphoramidate Prodrugs of 3'-deoxy-2',3'-didehydrothymidine Monophosphate," J. Med. Chem. 53, 7675-7681, Journal of Medicinal Chemistry Article, American Chemical Society, pubs.acs.org/jmc, 2010.
Saboulard, D. et al.; "Characterization of the activation pathway of phosphoramidate triester prodrugs of Stavudine and Zidovudine," Mol. Pharmacol. 1999, 56, pp. 693-704.
Sasaki H., Igaki H., Ishizuka T., Kogoma Y, Sugimura T., Terada M., Presence of *Streptococcus* DNA sequence in surgical specimens of gastric cancer. Jpn J Cancer Res 1995; 86:791-4.
Seno T., Ayusawa D., Shimizu K., Koyama H., Takeishi K., Hori T., Thymine-less death and genetic events in mammalian cells. Basic Life Sci 1985; 31 :241-63.
Sinigaglia F. and Talmadge K.W., Inhibition of [3H] thymidine incorporation by Mycoplasma arginine-infected cells due to enzymatic cleavage of the nucleoside. Eur J Immunol 1985; 15:692-696, 1985.
Slusarczyk et al., "Application of ProTide Technology to Gemcitabine: A Successful Approach to Overcome the Key Cancer Resistance Mechanisms Leads to a New Agent (NUC-1031) in Clinical Development," J. Med. Chem., 57:1531-1542 (2014).
Sobrero, A. F. et al., "Defective Facilitated Diffusion of Nucleosides, a Primary Mechanism of Resistance to 5-Fluoro-2'-deoxyuridine in HCT-8 Human Carcinoma Line," Cancer Res. 1985, 45, pp. 3155-3160.

(56) References Cited

OTHER PUBLICATIONS

Sotos G.A., Grogan L., Allegra C.J., Preclinical and clinical aspects of biomodulation of 5-fluorouracil. Cancer Treat Rev 1994; 20:11-49.
Tanaka F., et al.; The history, mechanism and clinical use of oral5-fluorouracil derivative chemotherapeutic agents. Curr Phann Biotechnol. 2000; 1: 137-64.
Tham T.N., Ferris S., Kovacic R., Montagnier L., Blanchard A., Identification of Mycoplasma prim genes involved in the salvage pathways for nucleosides. J Bacteriol. 1993; 175(16):5281-5.
Thornton, Peter J. et al., "Nucleoside Phosphate and Phosphonate Prodrug Clinical Candidates" Journal of Medicinal Chemistry 59 (23), pp. 10400-10410.Online Research @ Cardiff, Cardiff University, 35 pages (2016).
UK Search Report issued GB1016855.7 on Jan. 26, 2011.
UK Search Report issued GB1103582.1 dated Jun. 15, 2011.
Vail, D. M. et al., 2007 MCR Annual Meeting Los Angeles CA, "Efficacy and safety profile of GS-9219, a novel guanine nucleotide analog prodrug, for the treatment of lymphoid malignancies using pet dogs with spontaneous non-Hodgkin's lymphoma as a model," Apr. 18, 2007.
Vande Voorde et al.; The Cytostatic Activity of NUC-3073, a Phosphoramidate Prodrug of 5-fluoro-2'-deoxyuridine, is Independent of Activation by Thymidine Kinase and Insensitive to Degradation by Phosphorlytic Enzymes; Biochemical Pharmacology; vol. 82, No. 5; Sep. 1, 2011; pp. 441-452.
Vijver et al.; "Antibacterial 5'-O-(N-dipeptidyl)-sulfamoyladenosines," Bioorganic& Medicinal Chemistry, 17(1):260-269 (2009).
Wagner, C.R. et al., "Pronucleotides: Toward the In Vivo Delivery of Antiviral and Anticancer Nucleotides," Med. Res. Rev. 2000, 20, DD. 417-451.
Walko C.M. and Lindley C., Capecitabine: a review. Clin Ther 2005; 27:23-44.
Walsby, E. et al., "Nucleoside Analogues of Cladribine Produce Enhanced Response in Cell Lines," Blood, 2005, 106(11), pp. 941A-942A and Abstract 3369.
Yagil, E. et al., "Phosphorolysis of 5-Fluoro-2'-deoxyuridine in *Escherichia coli* and its Inhibition by Nucleosides," J. Bacteriol. 1971, 108 (2), pp. 760-764.
Yang H., et al.; Mycoplasma hyorhinis infection in gastric carcinoma and its effects on the malignant phenotypes of gastric cancer cells. BM.C. Gastroenterol. 2010; 10:132.
Zeng, Debin; et al.; "Discovery of 2'-α-C-Methyl-2'-β-C-fluorouridine Phosphoramidate Prodrugs as Inhibitors of Hepatitis C Virus," ACS Medicinal Chemistry Letters; DOI: 10.1021/acsmedchemlett.6b00270 ACS Med. Chem. Lett. 2016, 7, 1197-1201.
Zheng, ZG., "Mechanisms of Resistance to Fluoropyrimidines," Seminars Oncology vol. 19, No. 2 (1992) (2 Suppl. 3) pp. 4-9.
U.S. Pat. No. 9,834,577, B2, U.S. Appl. No. 15/753,237, filed Dec. 5, 2017, Dammalapati.
U.S. Pat. No. 10,005,810, B2, U.S. Appl. No. 16/065,369, filed Jul. 5, 2022, Griffith.
U.S. Pat. No. 10,117,888, B2, U.S. Appl. No. 16/060,681, filed Nov. 6, 2018, Griffith et al.
U.S. Pat. No. 10,662,213, B2, U.S. Appl. No. 15/994,378, filed May 26, 2020, Griffith et al.
U.S. Pat. No. 10,669,300, B2, U.S. Appl. No. 15/514,673, filed Jun. 2, 2020, Griffith.
U.S. Pat. No. 10,660,912, B2, U.S. Appl. No. 15/411,409, filed May 26, 2020, Griffith.
U.S. Pat. No. 10,786,523, B2, U.S. Appl. No. 16/142,948, filed Sep. 29, 2020, Griffith et al.
U.S. Pat. No. 11,040,997, B2, U.S. Appl. No. 15/308,491, filed Jun. 22, 2021, McGuigan et al.
U.S. Pat. No. 10,774,104, B2, U.S. Appl. No. 15/308,475, filed Sep. 15, 2020, Kotala et al.
U.S. Pat. No. 11,377,467, B2, U.S. Appl. No. 14/442,987, filed Jul. 5, 2022, Griffith.
U.S. Pat. No. 11,040,051, B2, U.S. Appl. No. 17/010,338, filed Jun. 22, 2021, Griffith et al.
2019/0022117, A1, U.S. Appl. No. 16/065,498, filed Jan. 24, 2019, Griffith.
2019/0381084, A1, U.S. Appl. No. 16/065,476, filed Dec. 19, 2019, Griffith.
2022/0031727, A1, U.S. Appl. No. 17/324,835, filed Feb. 3, 2022, Griffith et al.
2022/0033433, A1, U.S. Appl. No. 17/323,367, filed Feb. 3, 2022, McGuigan et al.
2021/0100825, A1, U.S. Appl. No. 17/028,314, filed Apr. 8, 2021, Griffith et al.
2021/0009625, A1, U.S. Appl. No. 16/991,765, filed Jan. 14, 2021, Kotala et al.
2020/0268783, A1, U.S. Appl. No. 16/871,140, filed Aug. 27, 2020, Griffith.
2020/0262861, A1, U.S. Appl. No. 16/865,527, filed Aug. 20, 2020, Griffith et al.
2020/0197430, A1, U.S. Appl. No. 16/642,832, filed Jun. 25, 2020, Griffith.
2022/0323475, A1, U.S. Appl. No. 17/844,691, filed Oct. 13, 2022, Griffith.
U.S. Appl. No. 17/532,914, filed Nov. 22, 2021, Griffith et al.
U.S. Appl. No. 17/883,472, filed Aug. 8, 2022, Griffith et al.
U.S. Appl. No. 17/845,878, filed Jun. 21, 2022, Griffith et al.

\* cited by examiner

SYNTHESIS OF PHOSPHATE DERIVATIVES

RELATED APPLICATIONS

This application is a continuation of U.S. patent application Ser. No. 16/623,263, filed on Dec. 16, 2019, which is a § 371 national stage application based on Patent Cooperation Treaty Application serial number PCT/GB2018/051638, filed Jun. 14, 2018; which claims the benefit of priority to GB 1709471.5, filed Jun. 14, 2017.

FIELD OF THE INVENTION

The present invention generally relates to a novel process for the preparation of certain ProTides as particular phosphate diastereoisomers. The certain ProTides include those useful in the treatment of cancer such as NUC-3373 (5-fluoro-2'-deoxyuridine-5'-O-[1-naphthyl(benzyloxy-L-alaninyl)] phosphate), NUC-7738 (3'-deoxyadenosine-5'-O-[phenyl(benzyloxy-L-alaninyl)] phosphate) and NUC-9701 (8-chloroadenosine-5'-O-[naphthyl(benzyloxy-L-alaninyl)] phosphate)

BACKGROUND OF THE INVENTION

ProTides are masked phosphate derivatives of nucleosides. They have been shown to be particularly potent therapeutic agents in the fields of both antivirals and oncology. ProTides, more specifically, are prodrugs of monophosphorylated nucleosides. These compounds appear to avoid many of the inherent and acquired resistance mechanisms which limit the utility of the parent nucleosides (see, for example, '*Application of ProTide Technology to Gemcitabine: A Successful Approach to Overcome the Key Cancer Resistance Mechanisms Leads to a New Agent (NUC-1031) in Clinical Development*'; Slusarczyk et al; *J. Med. Chem.*; 2014, 57, 1531-1542).

NUC-3373 (5-fluoro-2'-deoxyuridine-5'-O-[1-naphthyl(benzoxy-L-alaninyl)] phosphate) is a ProTide adaptation of 5FU/FUDR, the current foundation treatment against colorectal cancer. NUC-3373 and a range of related compounds have shown activity in vitro against a range of cancer models, in many cases and in particular for NUC-3373 that activity was outstanding and far superior to the results obtained with 5-fluorouracil. The addition of the ProTide phosphoramidate moiety to the 5-fluorouracil/FUDR molecule confers the specific advantages of delivering the key activated form of the agent (FdUMP) into the tumour cells. Non clinical studies have demonstrated that NUC-3373 overcomes the key cancer cell resistance mechanisms associated with 5-FU and its oral pro-drug capecitabine, generating high intracellular levels of the active FdUMP metabolite, resulting in a much greater inhibition of tumour cell growth. Furthermore, in formal dog toxicology studies, NUC-3373 is significantly better tolerated than 5-FU (see WO2012/117246; McGuigan et al.; *Phosphoramidate Pro Tides of the anticancer agent FUDR successfully deliver the preformed bioactive monophosphate in cells and confer advantage over the parent nucleoside; J. Med. Chem.*; 2011, 54, 7247-7258; and Vande Voorde et al.; *The cytostatic activity of NUC-3073, a phosphoramidate prodrug of 5-fluoro-2'-deoxyuridine, is independent of activation by thymidine kinase and insensitive to degradation by phosphorolytic enzymes; Biochem. Pharmacol.*; 2011, 82, 441-452).

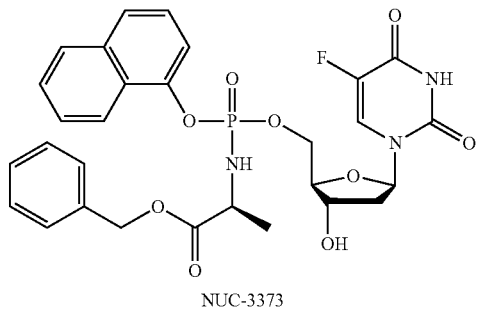

NUC-3373

ProTide derivatives of purine nucleosides such as 8-chloroadenosine and 3'-deoxyadenosine and related compounds have also shown excellent activity in vitro against a range of solid tumours, leukaemias and lymphomas (see WO2016/083830 and GB1609602.6). 3'-Deoxyadenosine itself is not a particularly potent anticancer agent.

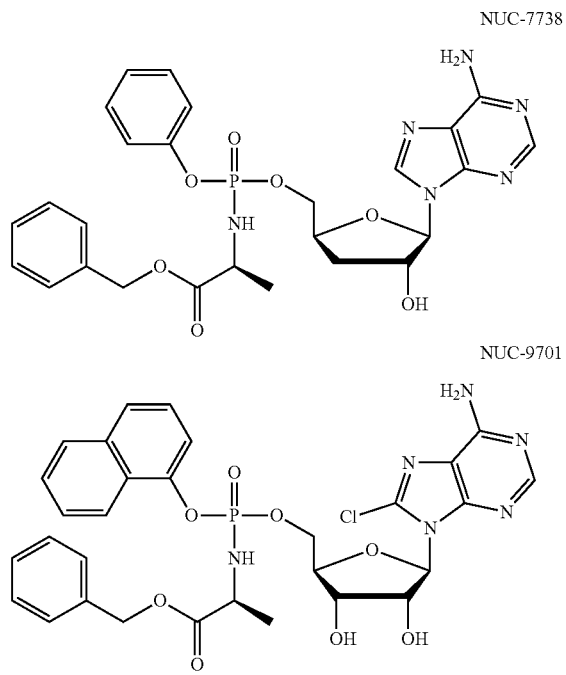

ProTides are typically prepared as a mixture of two diastereoisomers, epimeric at the phosphate centre. The diastereoisomers of NUC-3373, for example, have the following structures (in which Np is a 1-napthyl):

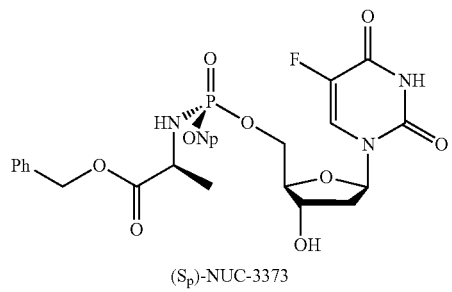

($S_P$)-NUC-3373

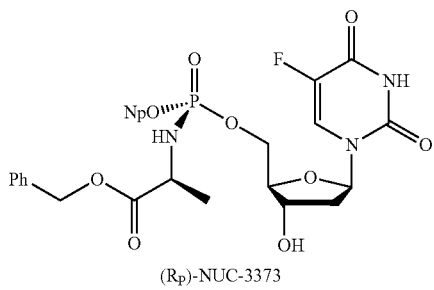

(R$_P$)-NUC-3373

WO 2014/076490 discloses a process for preparation of nucleoside prodrugs such as gemcitabine-[phenyl(benzoxy-L-alaninyl)] phosphate by reacting gemcitabine or its structural variants with a diastereoisomeric mixture of phosphorochloridates in the presence of a catalyst comprising metal salt such as Cu(OTf)$_2$, CuCl, CuBr, CuI, Cu(OAc)$_2$, CuSO$_4$, Cu(OC(O)CF$_3$)$_2$, Cu(OTf)$_2$, Yb(OTf)$_3$, Fe(OTf)$_3$, La(OTf)$_3$ with yield of ~45%.

A method for synthesizing NUC-1031 in diastereoisomerically pure form is described in WO2017/098252 (PCT/GB2016/053875).

It is an aim of certain embodiments of this invention to provide a method of providing NUC-3373, NUC-7738 and/or NUC-9701 in substantially diastereoisomerically pure form.

It is an aim of certain embodiments of this invention to provide a method of providing the (S$_p$) and/or (R$_p$)-epimer(s) of NUC-3373, NUC-7738 and/or NUC-9701 in substantially diastereoisomerically pure form(s) which is scalable, economic and/or efficient, e.g. more scalable, economic and/or efficient than methods using HPLC. Thus, it is an aim of certain embodiments of this invention to provide a method of providing the (S$_p$) and/or (R$_p$)-epimer(s) in substantially diastereoisomerically pure form(s) which is suitable for large scale manufacture.

It is an aim of certain embodiments of this invention to provide a simple method i.e. a method which involves a minimum number of process steps and or reagents of providing the (S$_p$) and/or (R$_p$)-epimer(s) in substantially diastereoisomerically pure form(s).

Another aim of certain embodiments of this invention is to provide a method which ensures the separated (S$_p$)- or (R$_p$)-epimer are provided in substantially diastereoisomerically pure form and at the same time meet or exceed the necessary criteria stipulated by organisations such as the US FDA concerning the amounts and nature of any trace impurities which arise from synthesis and separation.

Certain embodiments of this invention satisfy some or all of the above aims.

SUMMARY OF THE INVENTION

In accordance with a first aspect of the invention there is provided a process for the preparation of NUC-3373 (Formula Ia) in substantially diastereoisomerically pure form:

Formula Ia

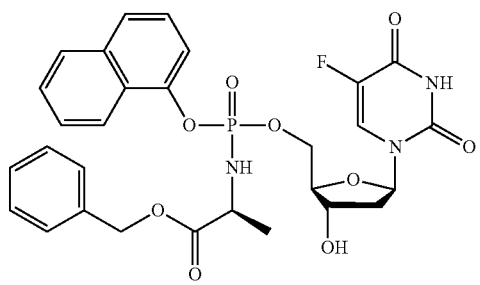

the process comprising step a) and optionally step b):

a) reacting a compound of Formula IIa; wherein R$^1$ represents an electron withdrawing group and a is an integer from 1 to 5, with a compound of Formula IIIa in presence of a base (B1) to provide a compound of Formula IVa in substantially diastereomerically pure form; wherein P$^1$ is independently selected from hydrogen and a protecting group; and wherein the compound of formula IIa is in substantially diastereomerically pure form:

Formula IIa

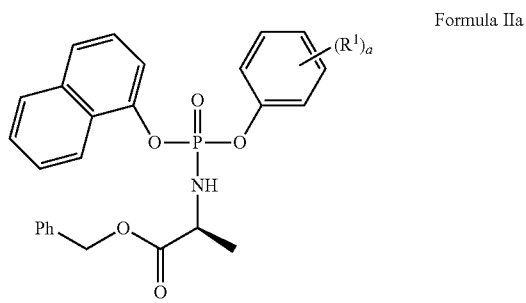

Formula IIIa

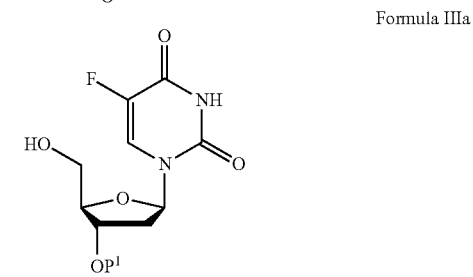

Formula IVa

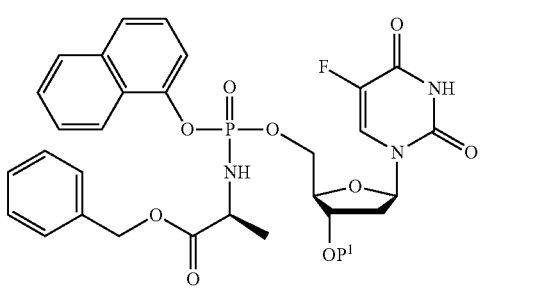

b) where P$^1$ is a protecting group, optionally removing the protecting group P$^1$ from the compound of formula IVa to provide NUC-3373 in substantially diastereomerically pure form.

In accordance with a second aspect of the invention there is provided a process for the preparation of NUC-7738 (Formula Ib) in substantially diastereoisomerically pure form:

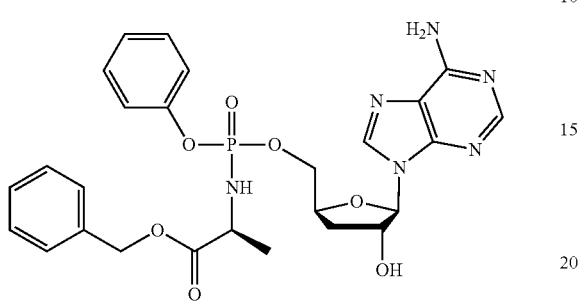

Formula Ib the process comprising step a) and optionally step b):
a) reacting a compound of Formula IIb; wherein R¹ represents an electron withdrawing group and a is an integer from 1 to 5, with a compound of Formula IIIb in presence of a base (B1) to provide a compound of Formula IVb in substantially diastereomerically pure form; wherein P², P³ and P⁴ are each independently selected from hydrogen and a protecting group; and wherein the compound of formula IIb is in substantially diastereomerically pure form:

Formula IIb

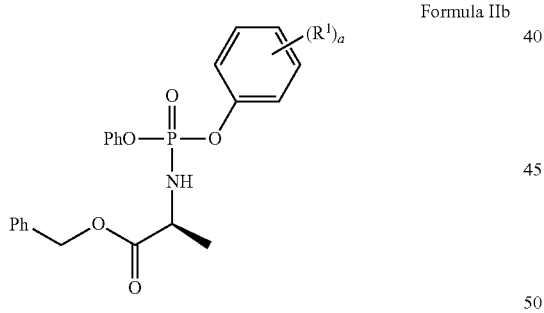

Formula IIIb

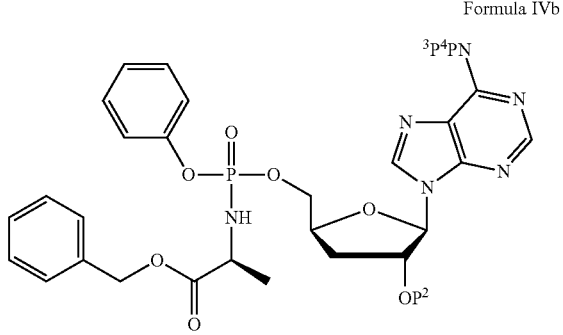

Formula IVb

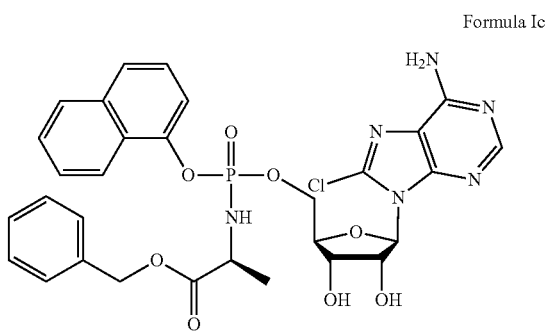

b) where any one or more of P², P³ and P⁴ are protecting groups, optionally removing the protecting groups P², P³ and P⁴ from the compound of formula IVb to provide NUC-7738 in substantially diastereomerically pure form.

In accordance with a third aspect of the invention there is provided a process for the preparation of NUC-9701 (Formula Ic) in substantially diastereoisomerically pure form:

Formula Ic the process comprising step a) and optionally step b):
a) reacting a compound of Formula IIa; wherein R¹ represents an electron withdrawing group and a is an integer from 1 to 5, with a compound of Formula IIIc in presence of a base (B1) to provide a compound of Formula IVc in substantially diastereomerically pure form; wherein P⁵, P⁶, P⁷ and P⁸ are each independently selected from hydrogen and a protecting group; and wherein the compound of formula IIa is in substantially diastereomerically pure form:

Formula IIa

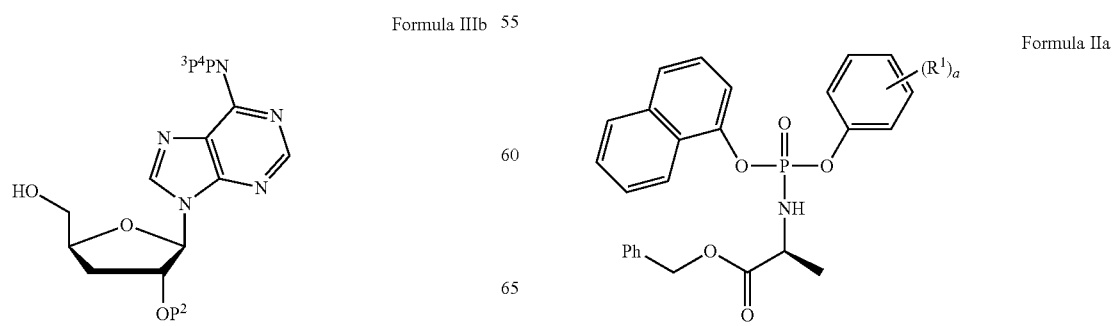

Formula IIIc

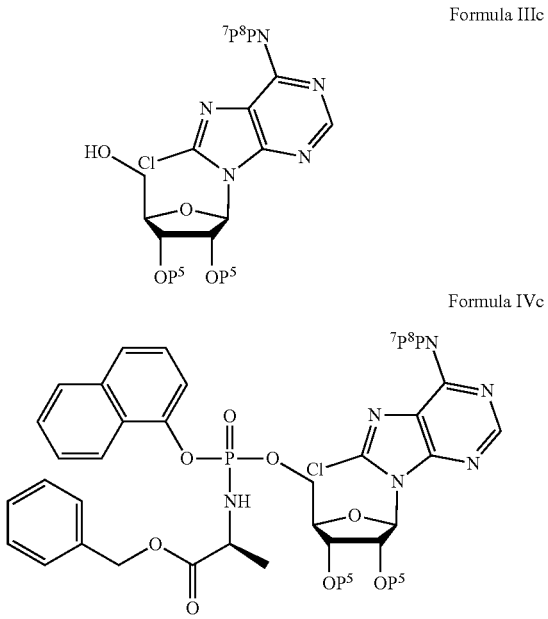

Formula IVc b) where any one or more of $P^5$, $P^6$, $P^7$ and $P^8$ are protecting groups, optionally removing the protecting groups $P^5$, $P^6$, $P^7$ and $P^8$ from the compound of formula IVc to provide NUC-9701 in substantially diastereomerically pure form.

$R^1$ may be selected from the group comprising: halo group (e.g. selected from fluoro, bromo, chloro or iodo); trifluoromethyl, cyano and nitro. a is an integer between 1 and 5. $R^1$ may be at each occurrence halo, e.g. fluoro. a may be 5.

Displacement of the substituted phenoxy group takes place selectively with inversion of phosphate stereocentre.

Typically the $(S_p)$-diastereoisomer of the precursor (the compound of formula IIa or Ib) provides the $(S_p)$-diastereoisomer of the ProTide and the $(R_p)$-diastereoisomer of the precursor provides the $(R_p)$-diastereoisomer of the ProTide. The exception to this is when the $OPh(R^1)_a$ leaving group has lower priority assignment under the Cahn-Ingold-Prelog rules than the naphthyl group (e.g. where $OPh(R^1)_a$ is paranitrophenoxy). In such cases, the $(R_p)$-diastereoisomer of the precursor (the compound of formula IIa) provides the $(S_p)$-diastereoisomer of the ProTide and the $(S_p)$-diastereoisomer of the precursor provides the $(R_p)$-diastereoisomer of the protide. Throughout this specification, the isomer of the compound of formula IIa that provides the $(S_p)$-isomer of the ProTide is referred to as the X-diastereoisomer and the isomer of the compound of formula IIa that provides the $(R_p)$-isomer of the ProTide is referred to as the Y-diastereoisomer. For compound IIb, it is always the case that the $(S_p)$-diastereoisomer of the precursor (the compound of formula IIb) provides the $(S_p)$-diastereoisomer of the ProTide and the $(R_p)$-diastereoisomer of the precursor provides the $(R_p)$-diastereoisomer of the ProTide Thus, it may be that the process of the first, second or third aspect is a method of making the $(S_p)$-diastereoisomer of the ProTide in diastereomerically enriched form and the compound of formula IIa or IIb is in diastereomerically enriched form.

It may be that the process of the first, second or third aspect is a method of making the $(R_p)$-diastereoisomer of the ProTide in diastereomerically enriched form and the compound of formula IIa or IIb is in diastereomerically enriched form.

The base (B1) might be a nitrogen base. Nitrogen bases include N-alkylimidazoles, (e.g. N-methyl imidazole (NMI)), imidazole, optionally substituted pyridines, (e.g. collidine, pyridine, 2,6-lutidine) and trialkylamines (e.g. triethylamine, and diisopropylethylamine). Alternatively, the base (B1) may be an organometallic base or metal hydride base (e.g. NaH). Thus, the base may be a Grignard reagent (i.e. an alkylmagnesium halide). Exemplary Grignard reagents include t-butylmagnesium halides such as tBuMgCl, tBuMgBr. Preferably, the base is tBuMgCl.

Step a) may be carried out in a solvent S1.

In a fourth aspect of the invention, there is provided a process for the diastereoisomeric enrichment of a compound of Formula IIa; the process comprising:
   c) suspending or dissolving the X-diastereoisomer of the compound of Formula IIa or a mixture of the XR- and Y-diastereoisomers of the compound of Formula IIa in a solvent (S2),
   d) treating the solution or suspension with a base (B2) to obtain the X-diastereoisomer in substantially diastereomerically enriched form, and
   e) isolating the X-diastereoisomer of Formula IIa. Typically, the X-diastereoisomer is the (S)-diastereoisomer and the Y-diastereoisomer is the (R)-diastereoisomer.

The inventors have surprisingly found that upon treating compounds of formula IIa with a base, they isomerise, preferentially forming the X-diastereoisomer over the Y-diastereoisomer. Thus, the Y-diastereoisomer can be converted to the X-diastereoisomer or an epimeric mixture of the Y-diastereoisomer and the X-diastereoisomer can be converted to the X-diastereoisomer. This increases the net efficiency of any synthetic sequence for making the X-diastereoisomer of NUC-3373 or NUC-9701 which incorporates the process of the first or third aspect as it means that all of the compound of formula IIa, even a portion of that which originally formed as the Y-diastereoisomer can be used. Typically, the X-diastereoisomer is the (Sp)-diastereoisomer and the Y-diastereoisomer is the (Rp)-diastereoisomer.

It may be that the process comprises:
   forming the compound of Formula IIa as a mixture of the Y- and X-diastereoisomers; and that step c) comprises suspending or dissolving the mixture of the Y- and X-diastereoisomers of the compound of Formula IIa in a solvent (S2). Typically, the X-diastereoisomer is the (Sp)-diastereoisomer and the Y-diastereoisomer is the (Rp)-diastereoisomer.

The compound of formula IIa used in the process of the first or third aspect may be X-diastereoisomer formed according to the process of the fourth aspect. Typically, the X-diastereoisomer is the $(S_p)$-diastereoisomer and the Y-diastereoisomer is the $(R_p)$-diastereoisomer.

The process of the second aspect of the invention may comprise:
   c) suspending or dissolving the $R_p$-diastereoisomer of the compound of Formula IIb or a mixture of the $(R_p)$- and $(S_p)$-diastereoisomers of the compound of Formula IIb in a solvent (S2),
   d) treating the solution or suspension with a base (B2) to obtain $(S_p)$-diastereoisomer in substantially diastereomerically enriched form, and
   e) isolating the $(S_p)$-diastereoisomer of Formula IIb.

Thus, the process of the second aspect of the invention may comprise:

forming the compound of Formula IIb as a mixture of the (R$_p$)- and (S$_p$)-diastereoisomers; and that step c) comprises suspending or dissolving the mixture of the (R$_p$)- and (S$_p$)-diastereoisomers of the compound of Formula IIb in a solvent (S2).

The base (B2) may be selected from the group consisting of organic amine bases (e.g. primary, secondary, tertiary amines, cyclic amine; exemplary organic amine bases include bases include N-alkylimidazoles, [e.g. N-methyl imidazole (NMI), imidazole, optionally substituted pyridines, (e.g. collidine, pyridine, 2,6-lutidine) and trialkylamines (e.g. triethylamine, and diisopropylethylamine)]; or inorganic bases (e.g. alkali metal hydroxide, alkali metal carbonates, alkali metal alkoxides, alkali metal aryloxides). Preferably, B2 is a tertiary amine. Thus, B2 may be a trialkylamine. Most preferably, B2 is triethylamine.

The solvent S2 may be selected from the group consisting of amides, ethers, esters, ketones, aromatic hydrocarbons, halogenated solvents, nitriles, sulfoxides, sulfones and mixtures thereof. S2 may be an organic solvent. Organic solvents include but are not limited to ethers (e.g. tetrahydrofuran, dioxane, diethyl ether, t-butylmethylether); ketones (e.g. acetone and methyl isobutyl ketone); halogenated solvents (e.g. dichloromethane, chloroform and 1,2-dichloroethane); hydrocarbons (e.g. cyclohexane, pentane, hexane, heptane), aromatic solvents (e.g. benzene and toluene), esters (e.g. ethyl acetate) and amides (e.g. DMF, NMP); or mixtures thereof. Preferably, S2 is a hydrocarbon or is a mixture comprising a hydrocarbon. Where S2 is a mixture, it may be a mixture that comprises over 50% (e.g. over 70%) of the hydrocarbon. The hydrocarbon may be hexane. The hydrocarbon may be heptane. S2 may be a mixture of hexane or heptane and a polar organic solvent (e.g. an ether, ester, alcohol or halogenated solvent). S2 may be a mixture of hexane or heptane and a polar organic solvent, the mixture comprising over 50% (e.g. over 70%) by volume hexane or heptane. S2 may be a mixture of hexane or heptane and ethyl acetate. S2 may be a mixture of heptane and ethyl acetate. S2 may be a mixture of hexane or heptane and ethyl acetate, the mixture that comprising over 50% (e.g. over 70%) by volume hexane or heptane. S2 may be a mixture of heptane and ethyl acetate, the mixture comprising over 50% (e.g. over 70%) by volume heptane. S2 may be a mixture of hexane or heptane and methyl-t-butylether. S2 may be a mixture of hexane and methyl-t-butylether. S2 may be a mixture of hexane or heptane and methyl-t-butylether, the mixture that comprising over 50% (e.g. over 70%) by volume hexane or heptane. S2 may be a mixture of hexane and methyl-t-butylether, the mixture comprising over 50% (e.g. over 70%) by volume hexane.

Step d) may involve stirring the mixture of the compound of formula IIa and the base B2 for 24 h or longer. Step d) may involve stirring the mixture of the compound of formula IIa and the base B2 for 48 h or longer. Step b) may involve stirring the mixture of the compound of formula IIa and the base B2 for 60 h or longer. Step d) may involve stirring the mixture of the compound of formula IIa and the base B2 for 72 h or longer. Step d) may involve stirring the mixture of the compound of formula IIa and the base B2 for up to 100 h.

Step d) may involve stirring the mixture of the compound of formula IIa and the base B2 at a temperature from 0 to 60° C. Step d) may involve stirring the mixture of the compound of formula IIa and the base B2 at a temperature from 20 to 40° C.

Step d) may involve stirring the mixture of the compound of formula IIb and the base B2 for 2 h or longer. Step d) may involve stirring the mixture of the compound of formula IIb and the base B2 for 6 h or longer. Step b) may involve stirring the mixture of the compound of formula IIb and the base B2 for 10 h or longer. Step d) may involve stirring the mixture of the compound of formula IIb and the base B2 for 16 h or longer. Step d) may involve stirring the mixture of the compound of formula IIb and the base B2 for up to 36 h.

Step d) may involve stirring the mixture of the compound of formula IIb and the base B2 at a temperature from 0 to 50° C. Step d) may involve stirring the mixture of the compound of formula IIb and the base B2 at a temperature from 10 to 35° C.

In certain specific embodiments of the second aspect of the invention, the compound of Formula IIb is a compound selected from:

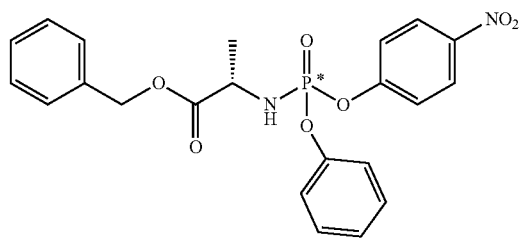

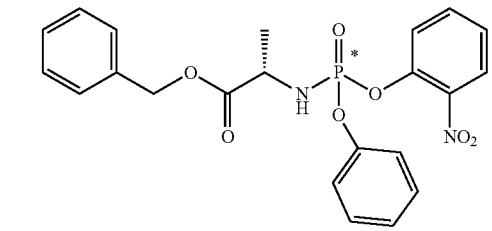

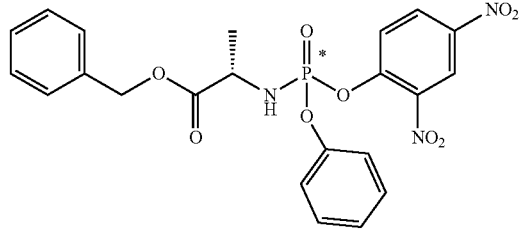

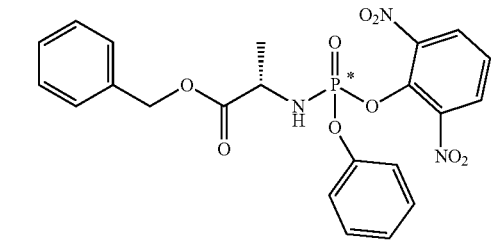

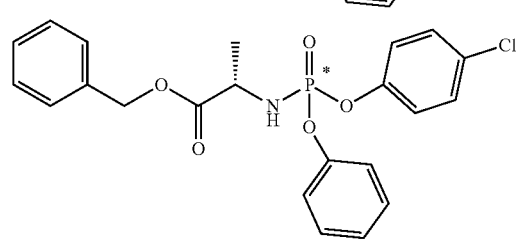

11
-continued
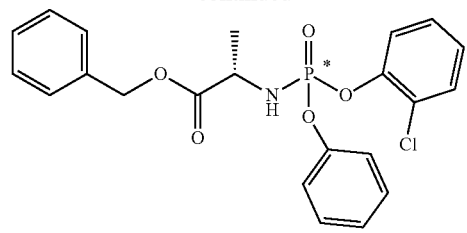
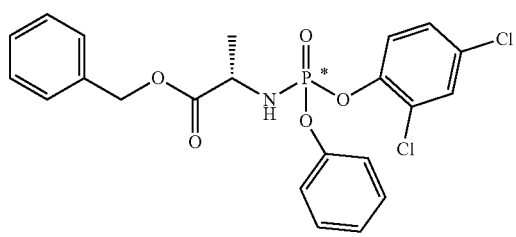
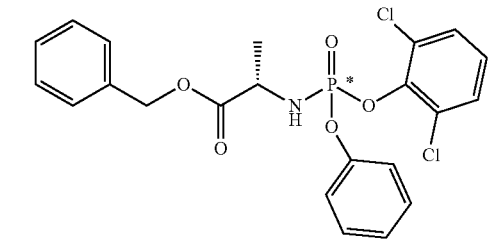
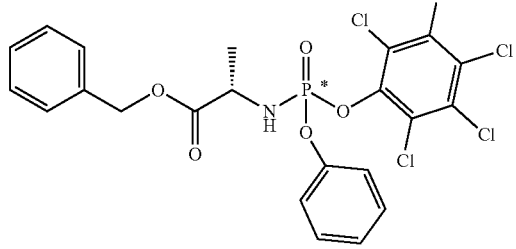
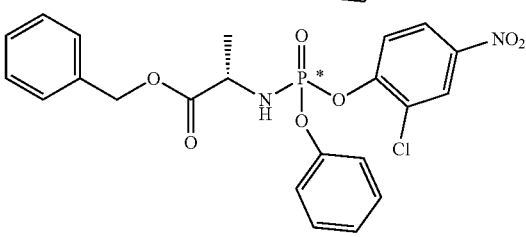
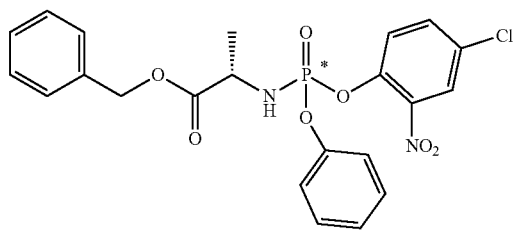
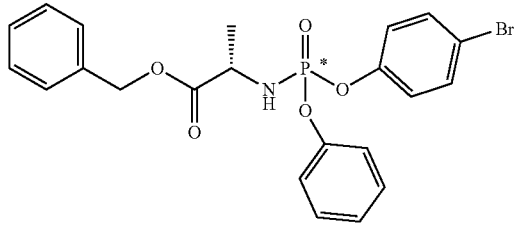
12
-continued
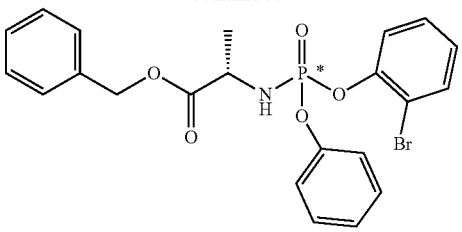
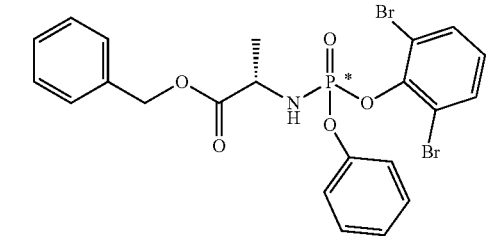
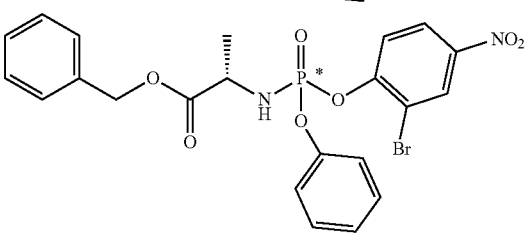
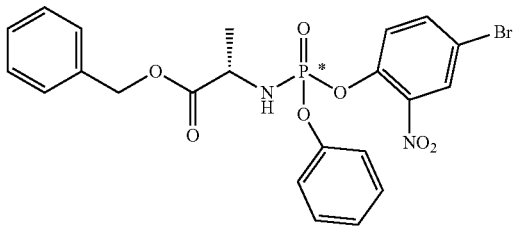
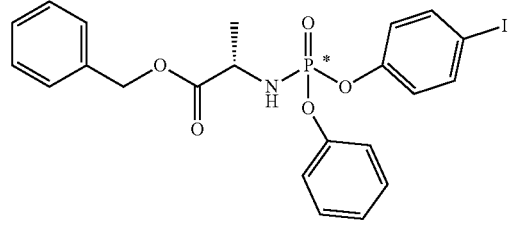
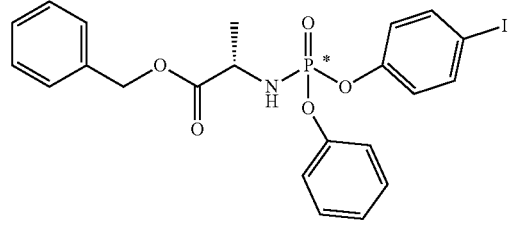

13
-continued
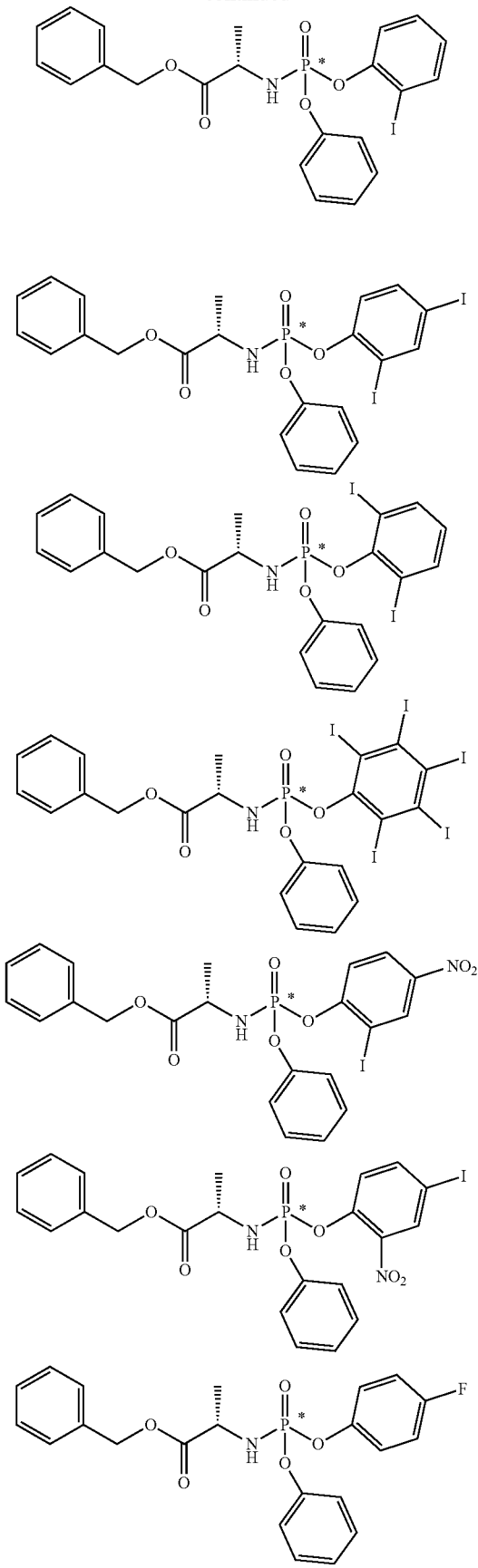
14
-continued
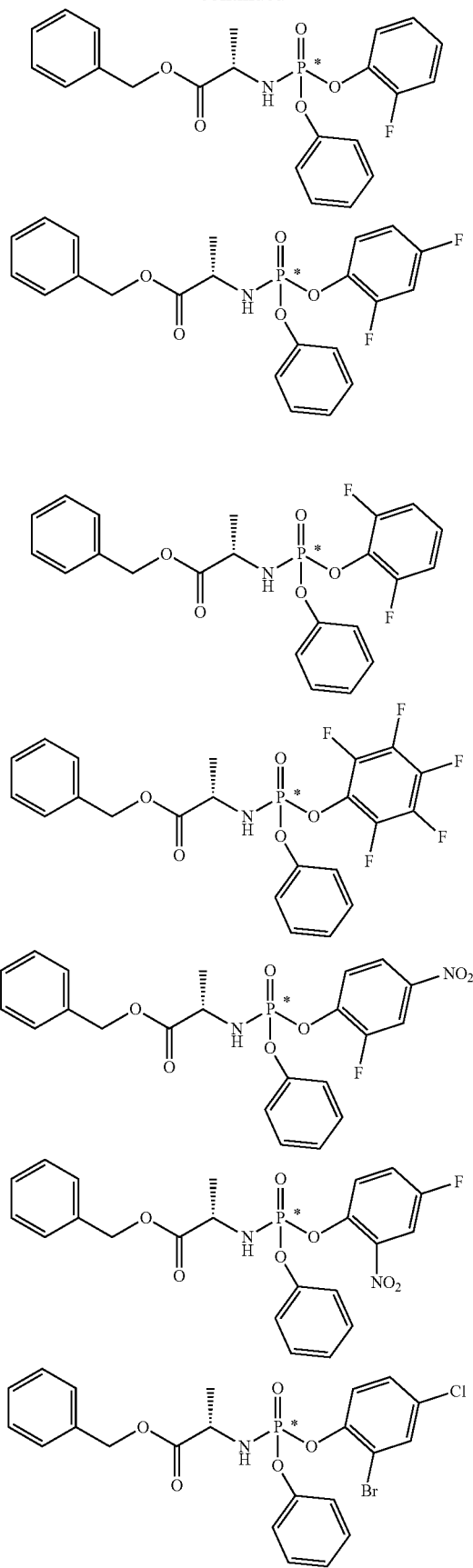

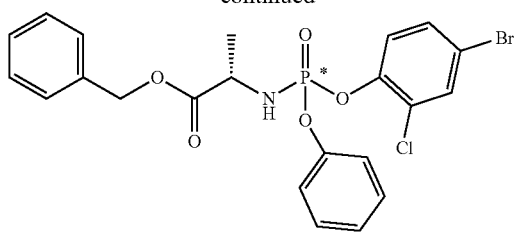
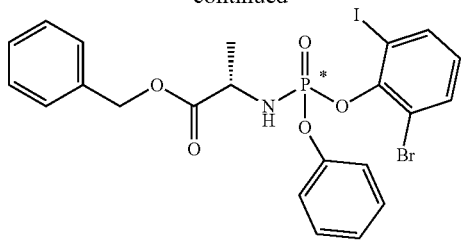
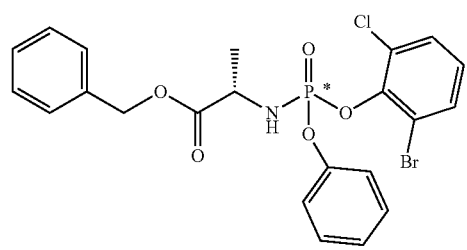
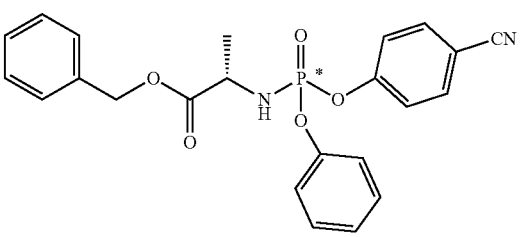
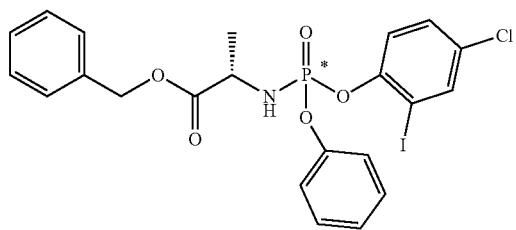
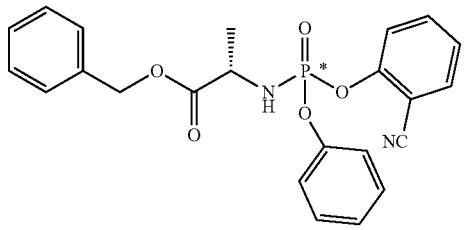
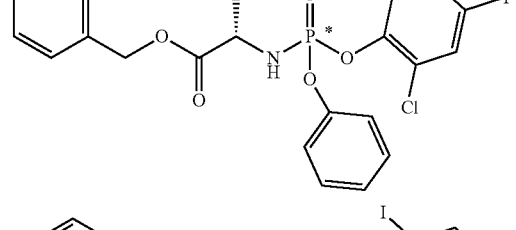
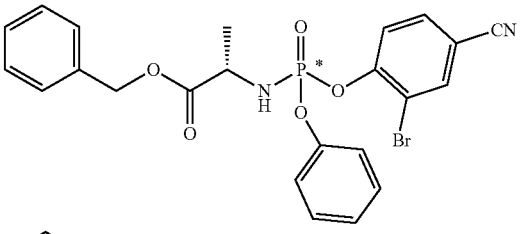
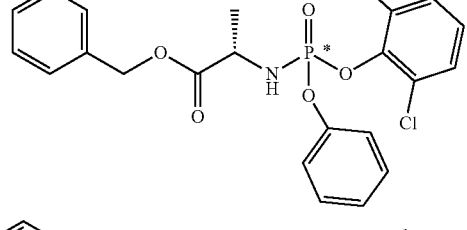
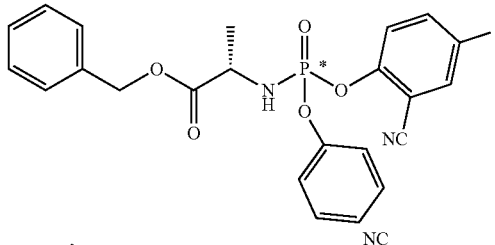
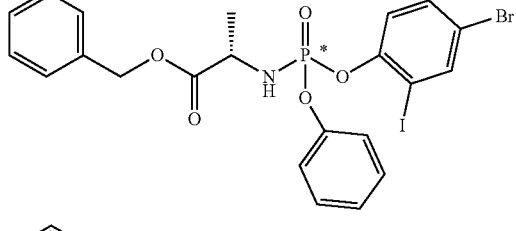
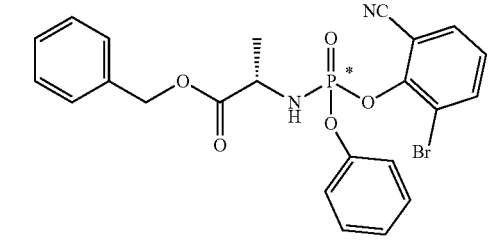
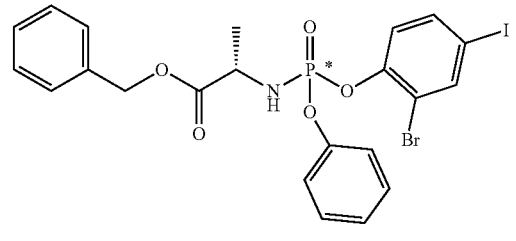
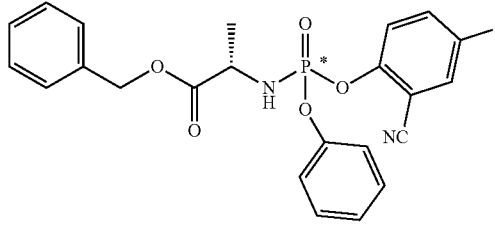

-continued
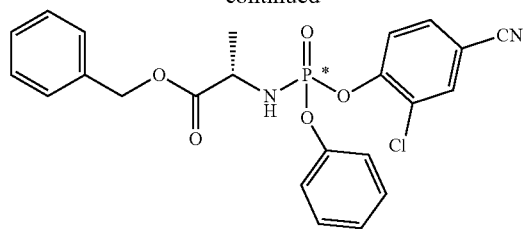
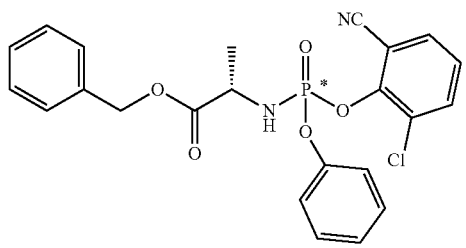
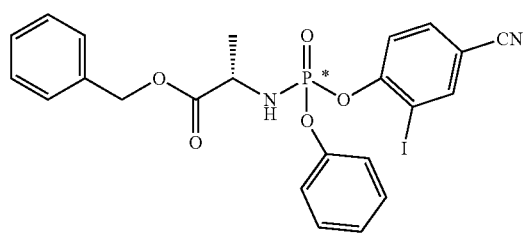
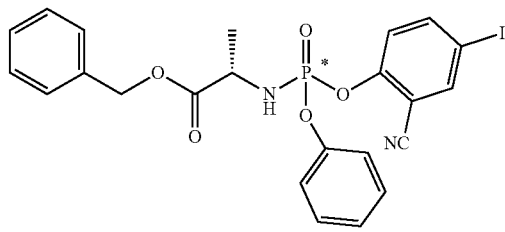
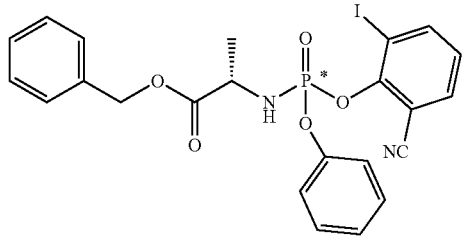
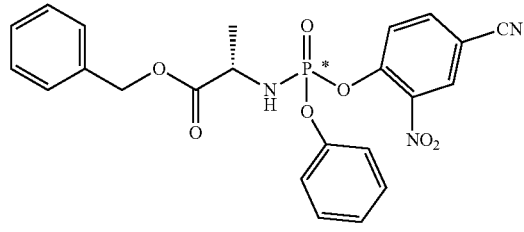
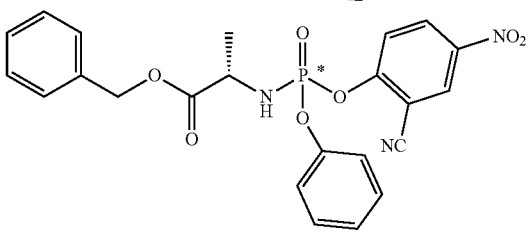
-continued
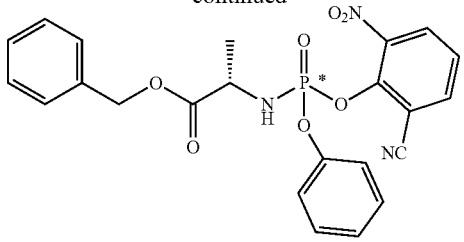
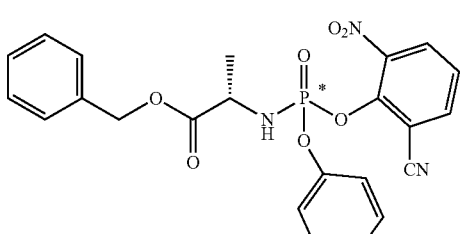
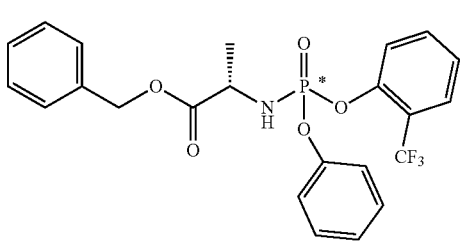
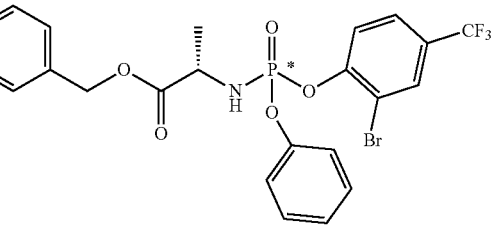
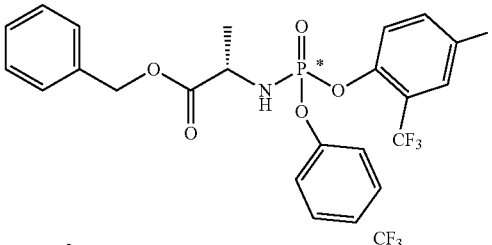
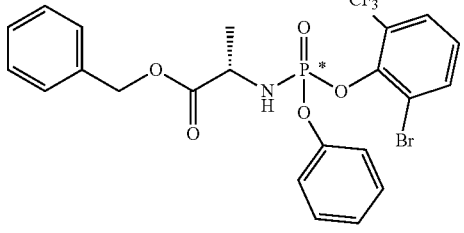
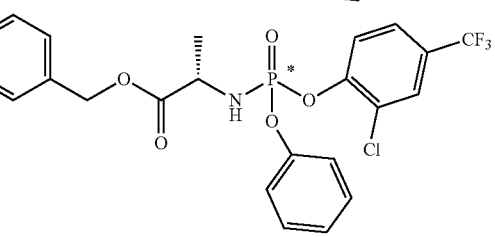

-continued
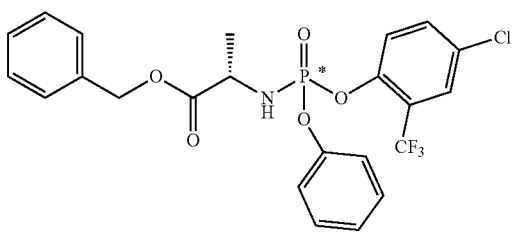
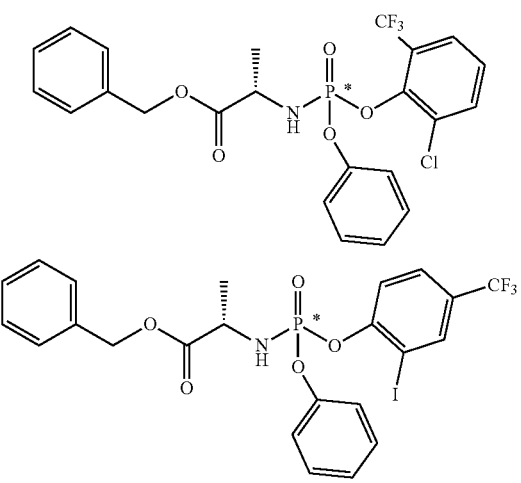
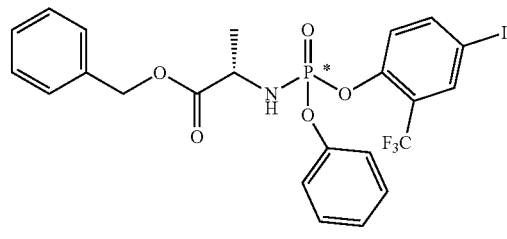
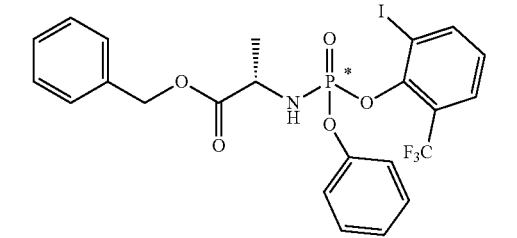
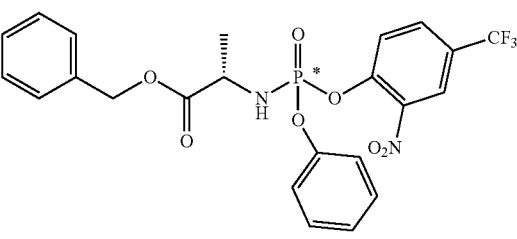
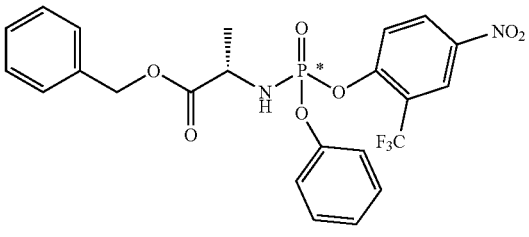
-continued
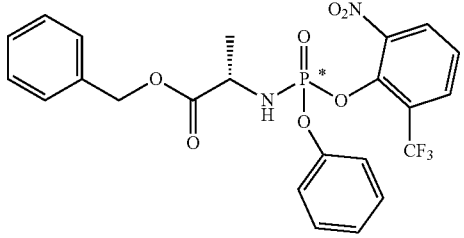
* represents chiral centre at the phosphorous
The compound of formula IIb may be:
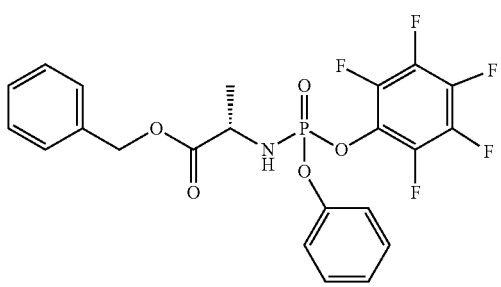 [SMILES: C[C@H](NP(=O)(Oc1ccccc1)Oc1c(F)c(F)c(F)c(F)c1F)C(=O)OCc1ccccc1]
The compound of formula IIb may be:
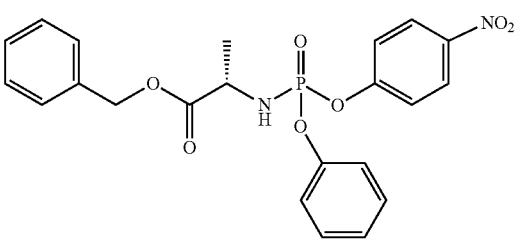 [SMILES: C[C@H](NP(=O)(Oc1ccccc1)Oc1ccc([N+](=O)[O-])cc1)C(=O)OCc1ccccc1]
In certain specific embodiments of the first, third and fourth aspect of the invention, the compound of Formula IIa is a compound selected from:
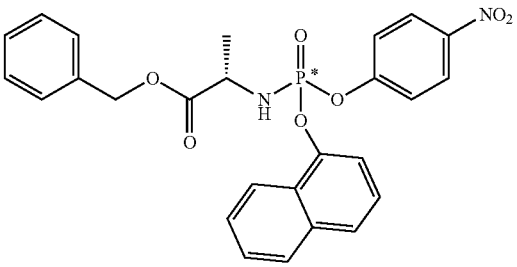
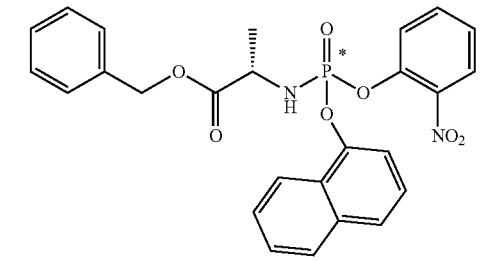

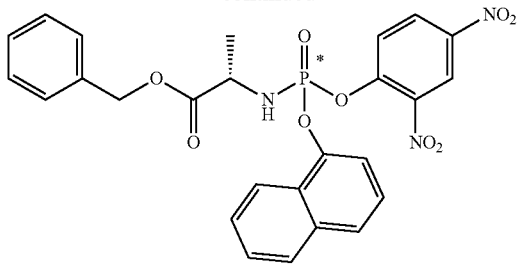
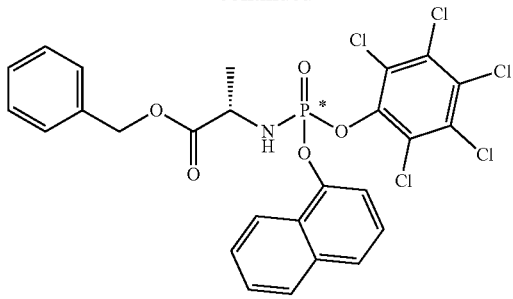
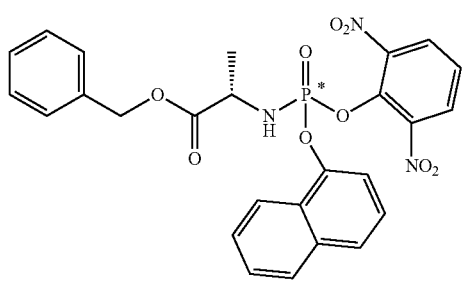
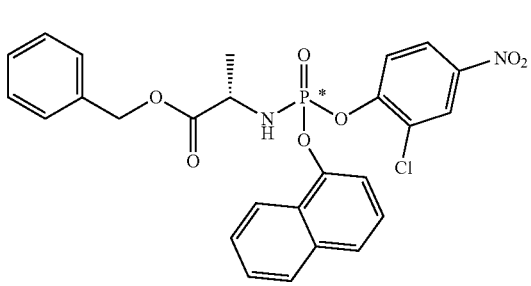
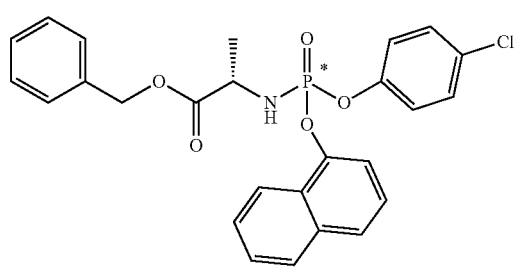
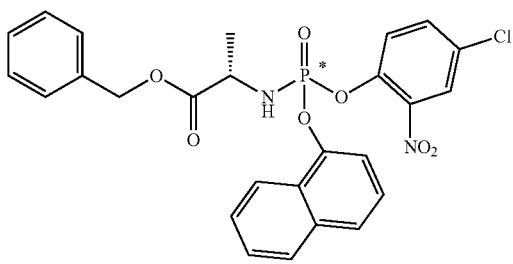
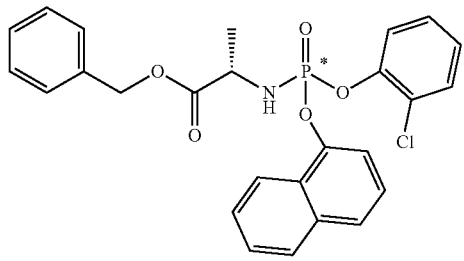
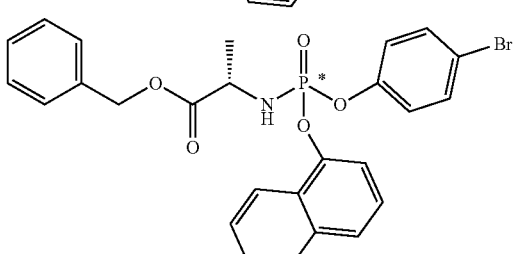
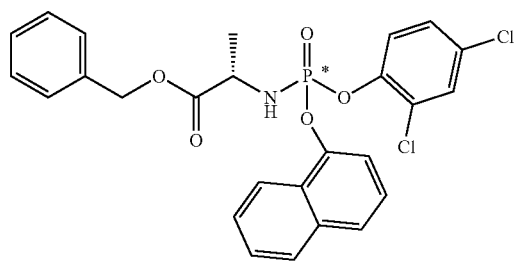
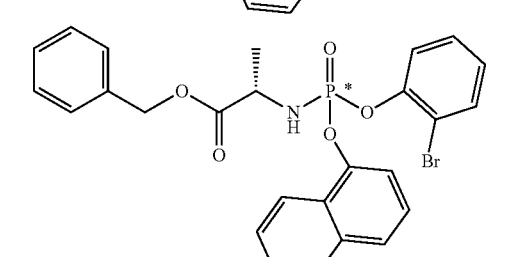
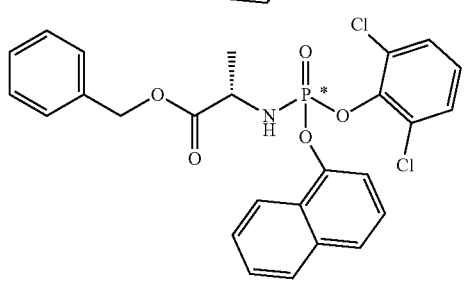
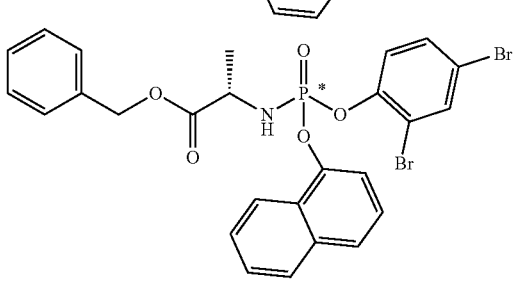

23
-continued
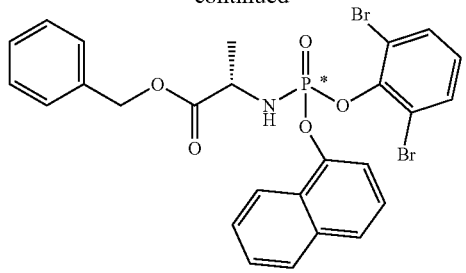
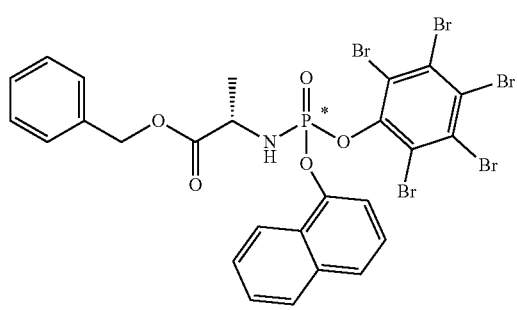
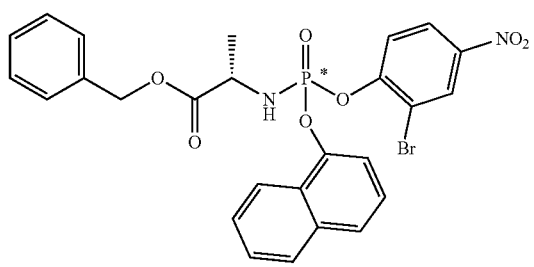
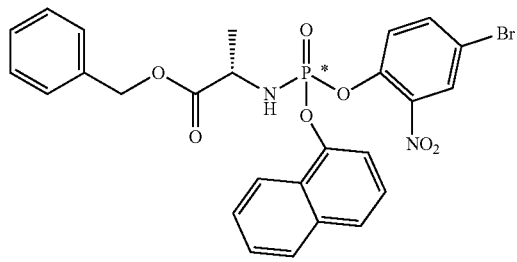
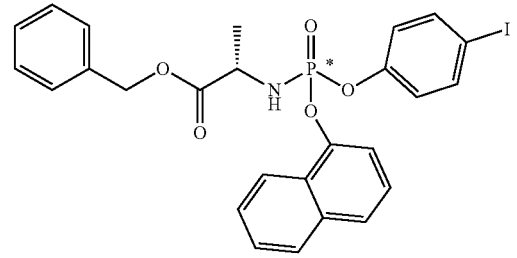
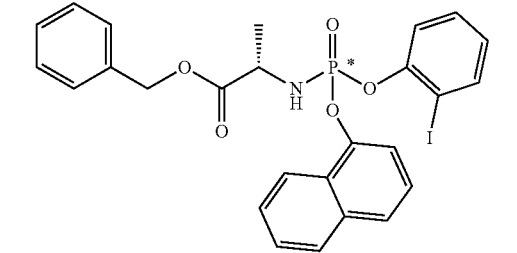
24
-continued
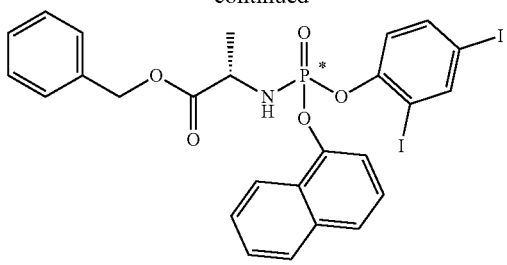
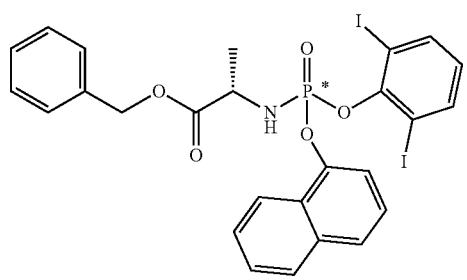
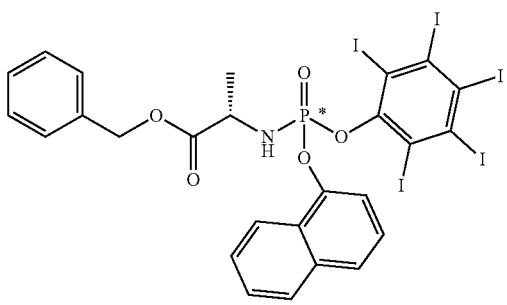
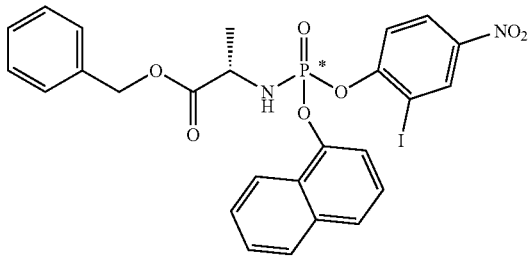
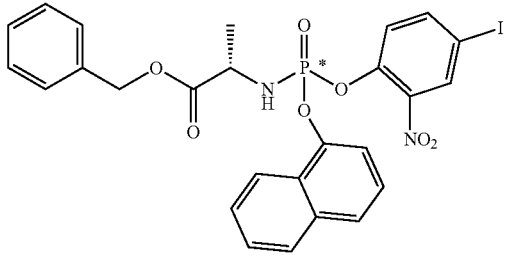
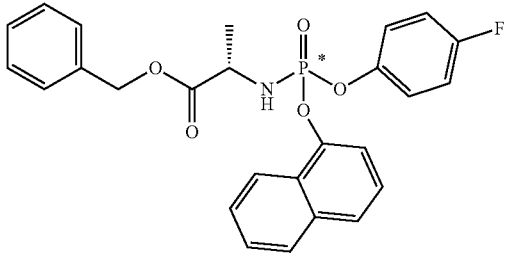

-continued
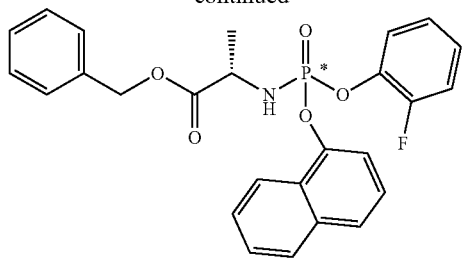
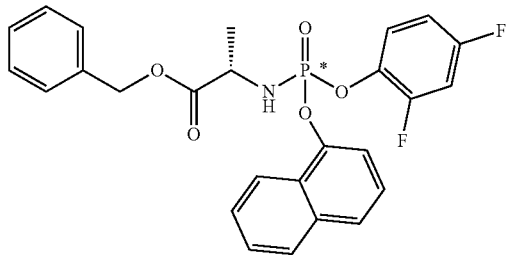
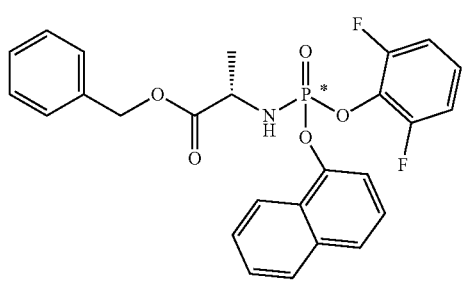
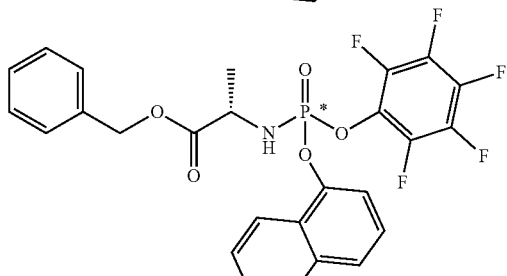
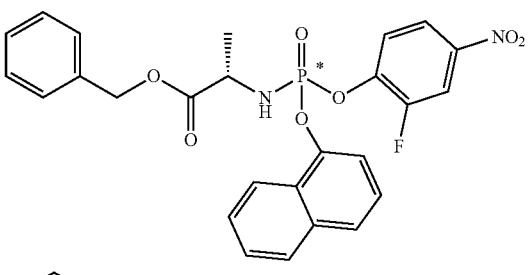
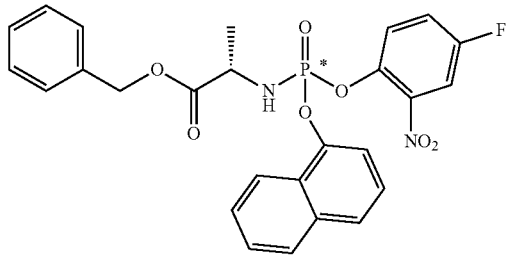
-continued
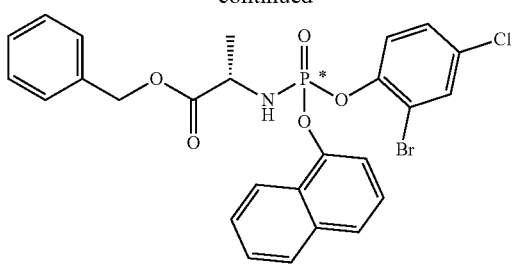
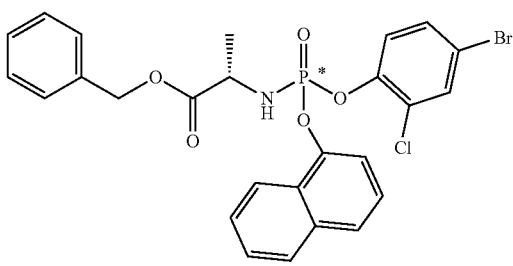
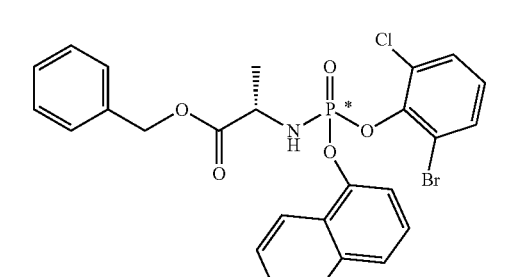
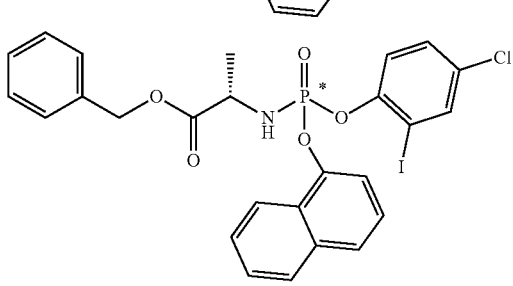
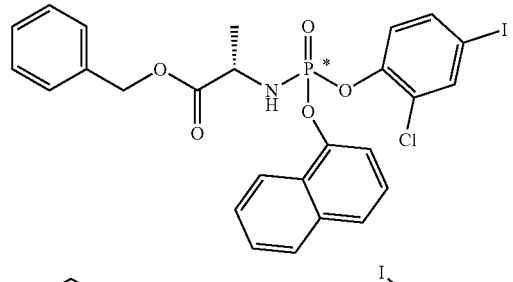
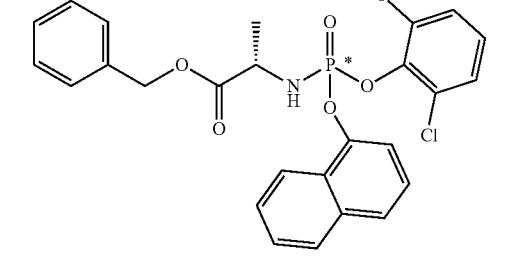

27
-continued
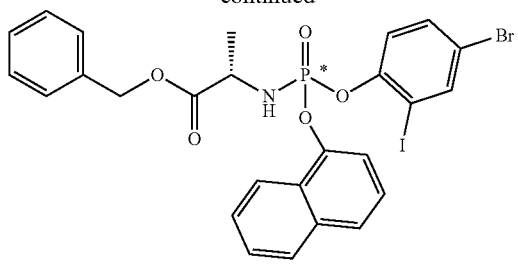
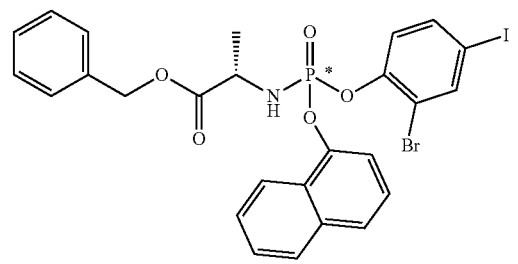
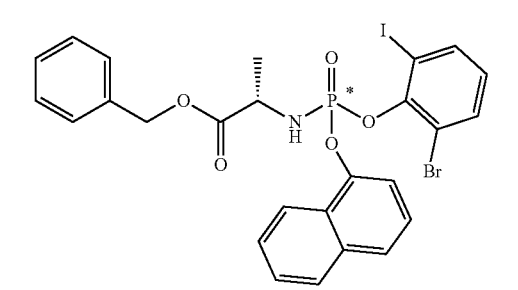
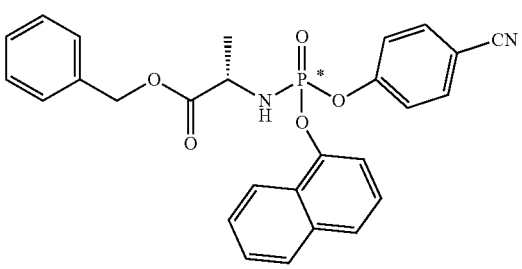
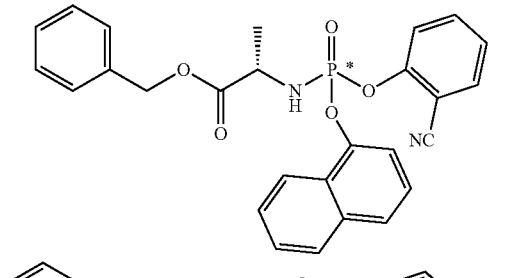
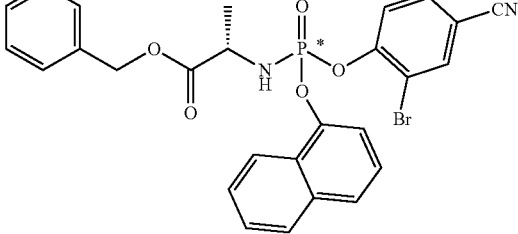
28
-continued
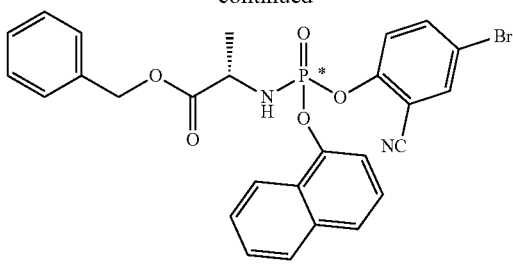
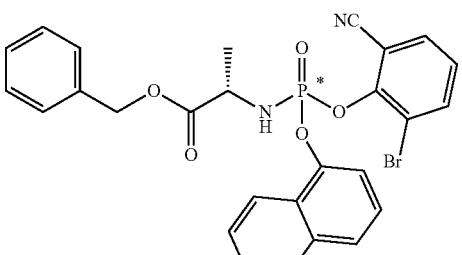
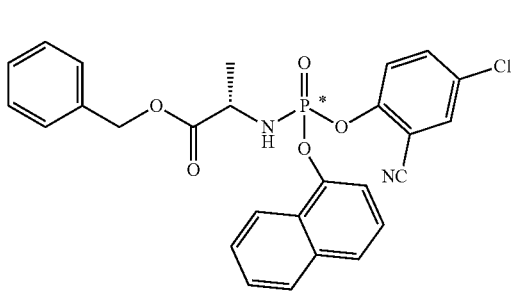
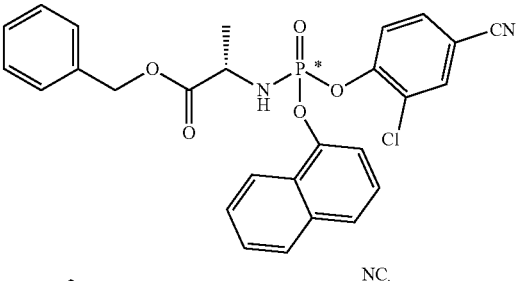
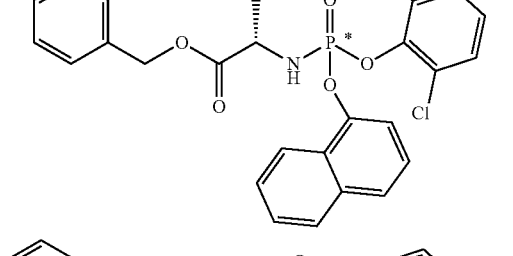
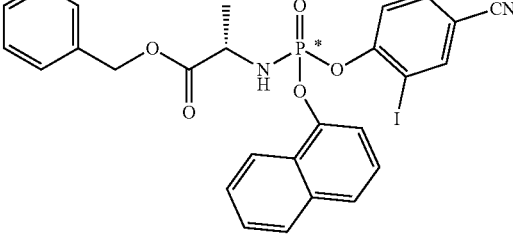

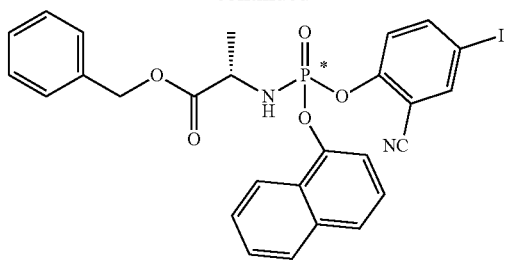
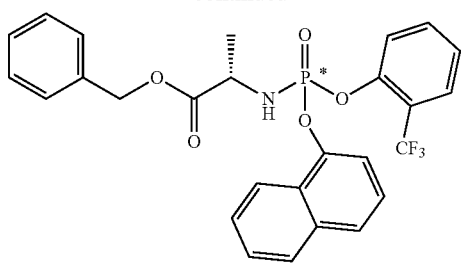
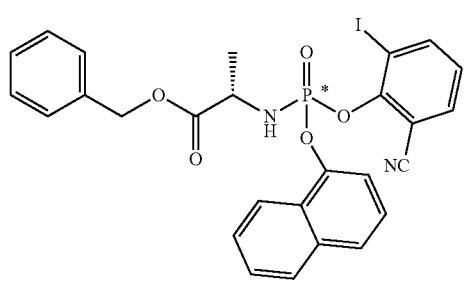
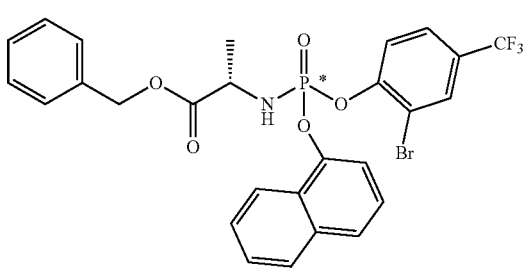
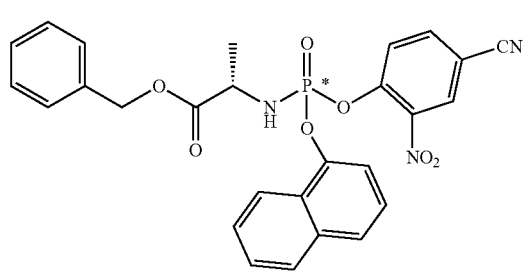
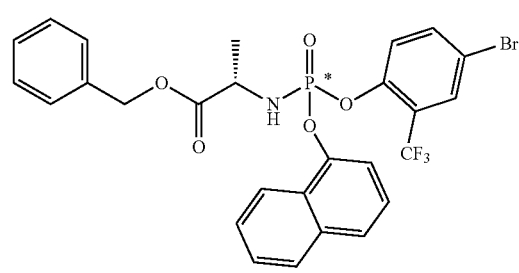
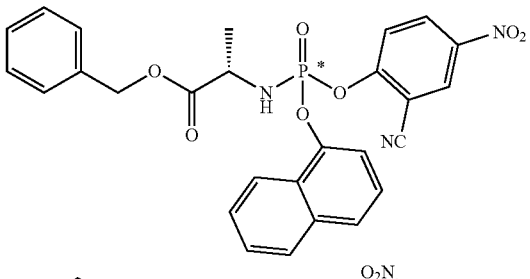
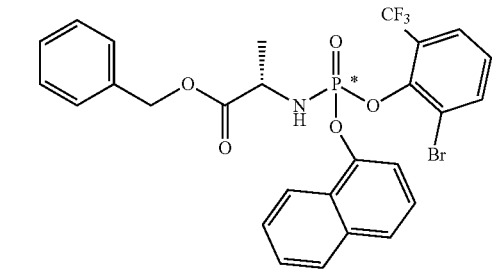
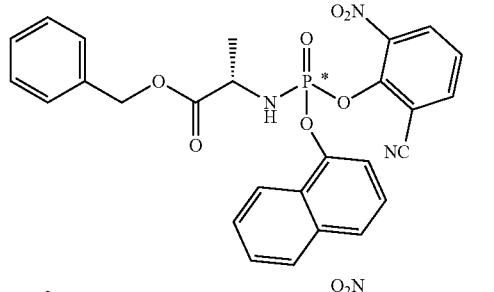
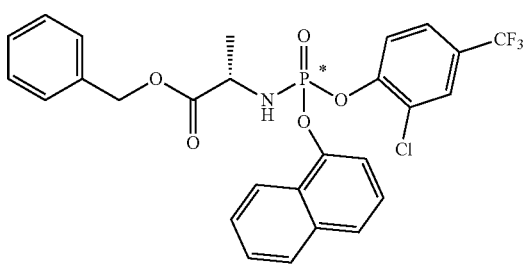
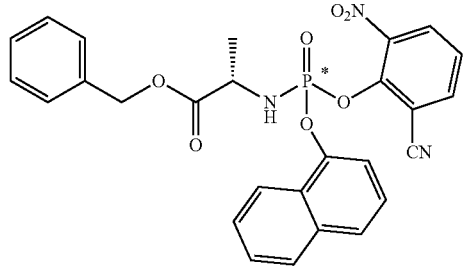
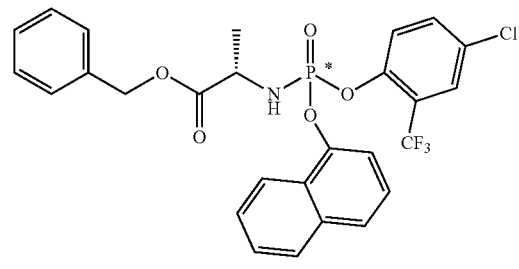

-continued

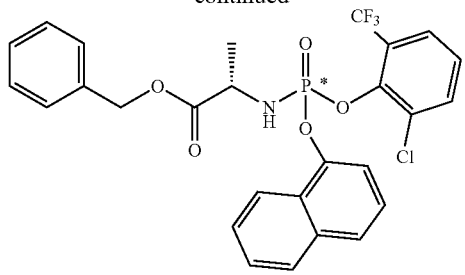

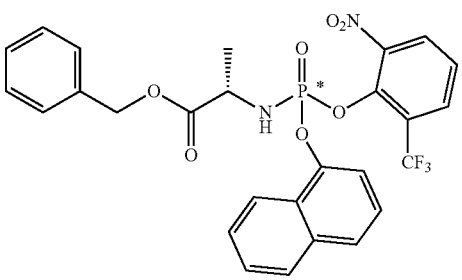

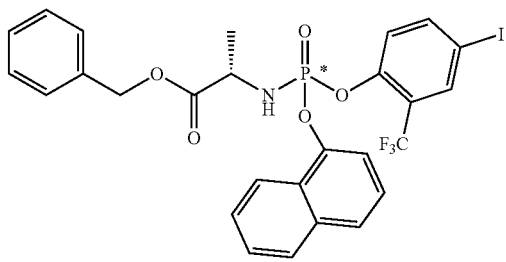

* represents chiral centre at the phosphorous

The compound of formula IIa may be compound 12:

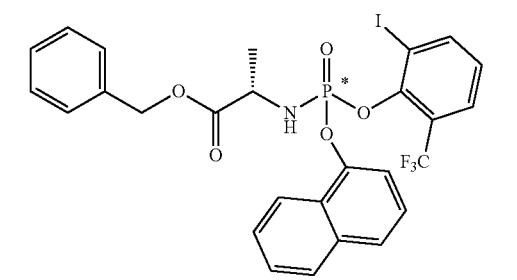

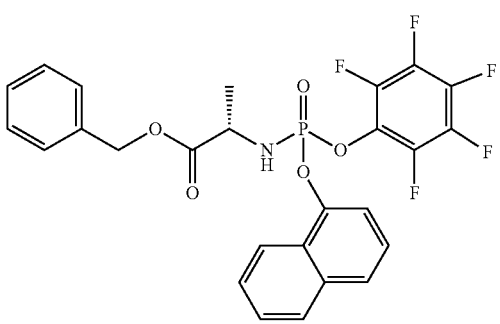

compound 12

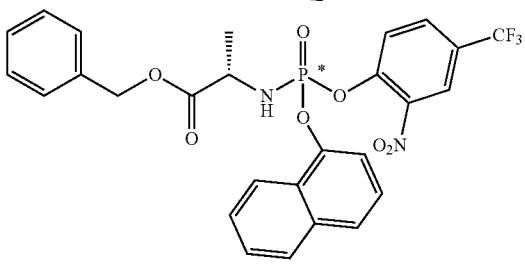

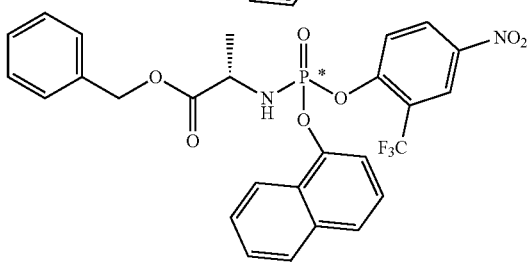

The compound of formula IIa may be ($R_p$)-compound 12 in substantially diastereomerically pure form. The compound may be the fast eluting isomer of compound 12 in substantially diastereoisomerically pure form. Thus, the compound may be the isomer of compound 12 that has a $^{31}$P NMR peak at −1.41±0.02 when the NMR spectrum has been obtained on a 202 MHz NMR machine in CDCl$_3$, said isomer being in substantially diastereoisomerically pure form. The compound may be the isomer of compound 12 that has a retention time of 12.96±0.20 minutes when analytical HPLC is performed on a Varian Pursuit XRs 5 C18, 150×4.6 mm eluting with H$_2$O/MeOH in 20/80 in 35 min at 1 mL/min, said isomer being in substantially diastereoisomerically pure form.

The compound of formula IIa may be ($S_p$)-compound 12 in substantially diastereomerically pure form. The compound may be the slow eluting isomer of compound 12 in substantially diastereoisomerically pure form. Thus, the compound may be the isomer of compound 12 that has a $^{31}$P NMR peak at −1.36±0.02 when the NMR spectrum has been obtained on a 202 MHz NMR machine in CDCl$_3$, said isomer being in substantially diastereoisomerically pure form. The compound may be the isomer of compound 12 that has a retention time of 14.48±0.20 minutes when analytical HPLC is performed on a Varian Pursuit XRs 5 C18, 150×4.6 mm eluting with H$_2$O/MeOH in 20/80 in 35 min at 1 mL/min, said isomer being in substantially diastereoisomerically pure form.

The compound of formula IIa may be:

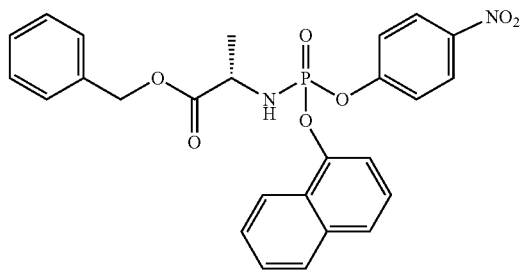 [SMILES: C[C@H](NP(=O)(Oc1ccc([N+](=O)[O-])cc1)Oc1cccc2ccccc12)C(=O)OCc1ccccc1]

The NUC-3373 may be the fast eluting isomer of NUC-3373 in substantially diastereoisomerically pure form. Thus, the NUC-3373 may be the isomer of NUC-3373 that has a $^{31}$P NMR peak at 4.27±0.10 when the NMR spectrum has been obtained on a 202 MHz NMR machine in CD$_3$OD, said isomer being in substantially diastereoisomerically pure form. The NUC-3373 may be the isomer of NUC-3373 that has a retention time of 16.03±0.20 minutes when analytical HPLC is performed on a Varian Pursuit XRs 5 C18, 150×4.6 mm eluting with H$_2$O/CH$_3$CN from 100/10 to 0/100 in 35 min at 1 mL/min, said isomer being in substantially diastereoisomerically pure form.

The NUC-3373 may be the slow eluting isomer of NUC-3373 in substantially diastereoisomerically pure form. Thus, the NUC-3373 may be the isomer of NUC-3373 that has a $^{31}$P NMR peak at 4.62±0.10 when the NMR spectrum has been obtained on a 202 MHz NMR machine in CD$_3$OD, said isomer being in substantially diastereoisomerically pure form. The NUC-3373 may be the isomer of NUC-3373 that has a retention time of 16.61±0.20 minutes when analytical HPLC is performed on a Varian Pursuit XRs 5 C18, 150×4.6 mm eluting with H$_2$O/CH$_3$CN from 90/10 to 0/100 in 35 min at 1 mL/min, said isomer being in substantially diastereoisomerically pure form.

The NUC-9701 may be the fast eluting isomer of NUC-9701 in substantially diastereoisomerically pure form. Thus, the NUC-9701 may be the isomer of NUC-9701 that has a $^{31}$P NMR peak at 3.93±0.04 when the NMR spectrum has been obtained on a 202 MHz NMR machine in CD$_3$OD, said isomer being in substantially diastereoisomerically pure form. The NUC-9701 may be the isomer of NUC-9701 that has a retention time of 16.43±0.10 minutes when analytical HPLC is performed on a Varian Pursuit XRs 5 C18, 150×4.6 mm eluting with H$_2$O/CH$_3$CN from 90/10 to 0/100 in 30 min at 1 mL/min, said isomer being in substantially diastereoisomerically pure form.

The NUC-9701 may be the slow eluting isomer of NUC-9701 in substantially diastereoisomerically pure form. Thus, the NUC-9701 may be the isomer of NUC-9701 that has a $^{31}$P NMR peak at 3.83±0.04 when the NMR spectrum has been obtained on a 202 MHz NMR machine in CD$_3$OD, said isomer being in substantially diastereoisomerically pure form. The NUC-9701 may be the isomer of NUC-9701 that has a retention time of 16.59±0.10 minutes when analytical HPLC is performed on a Varian Pursuit XRs 5 C18, 150×4.6 mm eluting with H$_2$O/CH$_3$CN from 100/10 to 0/100 in 30 min at 1 mL/min, said isomer being in substantially diastereoisomerically pure form.

The compound of formula IIa may be prepared according to the fourth aspect of the invention.

In a fifth aspect of the invention is provided a compound of formula IIa. The compound may be the Sp isomer of a compound of formula IIa. The compound may be the Rp isomer of a compound of formula IIa.

In a sixth aspect of the invention is provided (S$_p$)-NUC-3373:

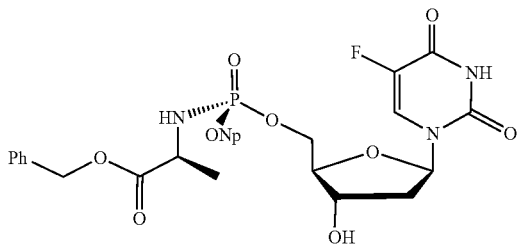

in substantially diastereoisomerically pure form. The preferential isomerization to form the X-diastereoisomer of the compound of formula IIa, means that the S$_p$ isomer of NUC-3373 is easier to produce than the R$_p$ isomer.

In a seventh aspect of the invention is provided (R$_p$)-NUC-3373:

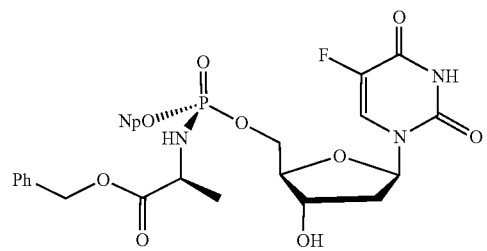

in substantially diastereoisomerically pure form.

In an eighth aspect of the invention is provided (S$_p$)-NUC-7738:

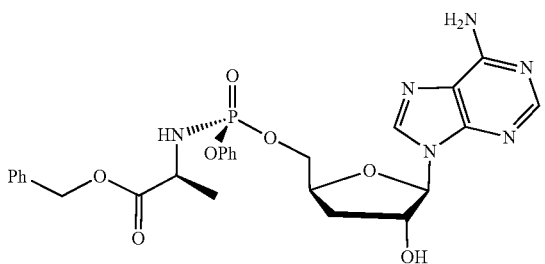

in substantially diastereoisomerically pure form. The preferential isomerization to form the (S)-diastereoisomer of the compound of formula IIb, means that the S$_p$ isomer of NUC-7738 is easier to produce than the R$_p$ isomer.

In an ninth aspect of the invention is provided (R$_p$)-NUC-7738:

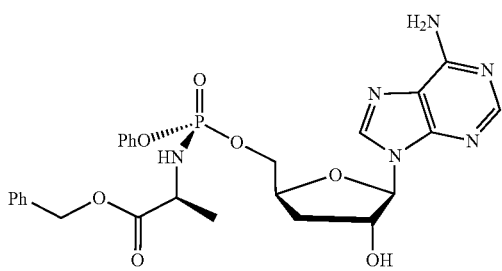

in substantially diastereoisomerically pure form.

In a tenth aspect of the invention is provided (S$_p$)-NUC-9701:

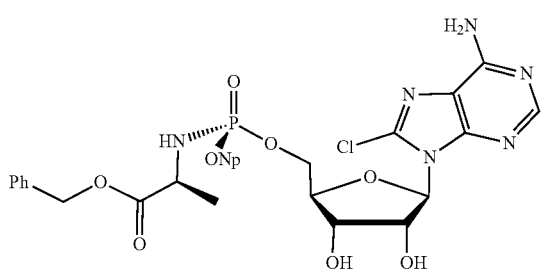

in substantially diastereoisomerically pure form. The preferential isomerization to form the X-diastereoisomer of the compound of formula IIa, means that the S$_p$ isomer of NUC-9701 is easier to produce than the R$_p$ isomer.

In an eleventh aspect of the invention is provided (R$_p$)-NUC-9701:

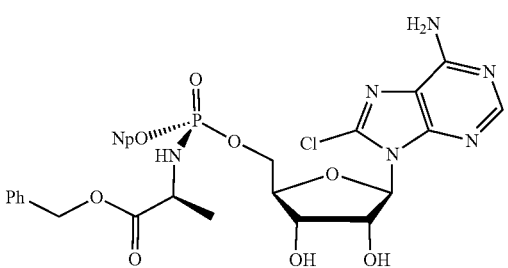

in substantially diastereoisomerically pure form.

The compound of the fifth, sixth, seventh, eighth, ninth, tenth and eleventh aspects of the invention may be a diastereoisomer described above for the first, second and third aspects of the invention.

The invention may also provide a pharmaceutical composition comprising a compound of the sixth, seventh, eighth, ninth, tenth and eleventh aspects of the invention and a pharmaceutically acceptable excipient.

The invention may also provide a method of treating cancer (e.g. a solid tumour or leukaemia), the method comprising administering to a subject in need thereof a therapeutically effective amount of a compound of the sixth, seventh, eighth, ninth, tenth and eleventh aspects of the invention.

The compounds of the sixth, seventh, eighth, ninth, tenth and eleventh aspects of the invention may be for medical use. The compounds of the sixth, seventh, eighth, ninth, tenth and eleventh aspects of the invention may be for use in treating cancer (e.g. a solid tumour or leukaemia).

The products of the sixth, seventh, eighth, ninth, tenth and eleventh aspects of the invention may be obtainable by (or obtained by) the first, second or third aspects of the invention.

A protecting group for a hydroxyl group (e.g. P$^1$, P$^2$, P$^5$ or P$^6$) may be independently selected from optionally substituted —Si(C$_1$-C$_6$-alkyl)$_3$, optionally substituted —C(O)—C$_1$-C$_6$-alkyl, optionally substituted —C(O)-aryl, optionally substituted —C(O)—OC$_1$-C$_6$-alkyl, —C(O)—O-allyl, —C(O)—O—CH$_2$-fluorenyl, optionally substituted —C(aryl)$_3$, optionally substituted —(C$_1$-C$_3$-alkylene)-aryl, optionally substituted —C(O)OCH$_2$-aryl and —C$_1$-C$_4$-alkyl-O—C$_1$-C$_4$-alkyl. Where two hydroxyl groups are attached to neighbouring carbon atoms (e.g. P$^5$ and P$^6$), they may be jointly protected with an optionally substituted —C(C$_1$-C$_4$-alkyl)$_2$-group.

A protecting group for an amino group (e.g. P$^3$, P$^4$, P$^7$ or P$^8$) may at each occurrence be independently selected from —C(O)OC$_1$-C$_6$-alkyl, optionally substituted —C(O)OCH$_2$-aryl, —C(O)—O-allyl, —C(O)—O—CH$_2$-fluorenyl, optionally substituted —C(aryl)$_3$, optionally substituted —(C$_1$-C$_3$-alkylene)-aryl, optionally substituted —C(O)—C$_1$-C$_6$-alkyl, optionally substituted —C(O)-aryl, —S(O)$_2$—C$_1$-C$_6$-alkyl, optionally substituted —S(O)$_2$-aryl and optionally substituted —Si(C$_1$-C$_6$-alkyl)$_3$.

Many of the protected starting compounds of Formula IIIa, IIIb or IIIc are known in the art and/or can be prepared by known methods. For example starting compounds of Formula IIIa, IIIb and IIIc may be synthesized from the parent nucleoside by protecting the hydroxy and/or amino groups with suitable protecting groups. The protecting groups can typically be added and removed using conventional protecting group methodology, for example, as described in "Protective Groups in Organic Chemistry," edited by J W F McOmie (1973); "Protective Groups in Organic Synthesis," 2$^{nd}$ edition, T W Greene (1991); and "Protecting Groups", 3$^{rd}$ addition P. J Koscienski (1995).

It will typically be necessary to prepare the compounds of formulae IIIa, IIIb and IIIc by first protecting the 5'-hydroxy group of the parent nucleoside with a protecting group which is orthogonal to those which will be used to protect the 3' and/or 2'-hydroxy and/or amino group (i.e. a group which can be removed from the 5'-hydroxyl group without also removing the desired 3'-hydroxyl, 2'-hydroxyl and/or amino protecting groups). Simultaneously or subsequently, the 3', 2'-hydroxyl and/or amino groups are protected with the desired protecting group(s) and the 5'-hydroxyl protecting group can be removed to generate the compound of formula IIIa, IIIb or IIIc. Certain protecting groups can be simultaneously introduced onto the 3' and/or 2'-hydroxyl and 5'-hydroxyl and optionally the amino groups and then selectively removed from the 5' hydroxyl group without being removed from the 3' and/or 2'-hydroxyl and optionally the amino groups.

According to some embodiments, P$^1$ is independently selected from optionally substituted —Si(C$_1$-C$_6$-alkyl)$_3$, optionally substituted —C(O)—C$_1$-C$_6$-alkyl, optionally substituted —C(O)-aryl, optionally substituted —C(O)—OC$_1$-C$_6$-alkyl, —C(O)—O-allyl, —C(O)—O—CH$_2$-fluorenyl, optionally substituted —C(aryl)$_3$, optionally substituted —(C$_1$-C$_3$-alkylene)-aryl, optionally substituted —C(O)OCH$_2$-aryl and —C$_1$-C$_4$-alkyl-O—C$_1$-C$_4$-alkyl.

P$^1$ may be independently selected from optionally substituted —Si(C$_1$-C$_6$-alkyl)$_3$, optionally substituted —C(O)—OC$_1$-C$_6$-alkyl and optionally substituted —C(O)OCH$_2$-aryl, —C(O)—O-allyl. Preferably, P$^1$ is selected from —C(O)O-tBu, —C(O)O-benzyl and —C(O)OCH$_2$-allyl. Thus, P$^1$ may be —C(O)OCH$_2$-aryl. P$^1$ may be —C(O)O-tBu.

Alternatively, P$^1$ may be independently selected from optionally substituted —C(O)—C$_1$-C$_6$-alkyl and optionally substituted —C(O)-aryl, e.g. $P^1$ may be independently selected from benzoyl and acetyl.

In a further alternative, $P^1$ may be optionally substituted —Si($C_1$-$C_6$-alkyl)$_3$. $P^1$ may be —Si($C_1$-$C_4$-alkyl)$_3$. The alkyl groups may be unsubstituted. $P^1$ may be t-butyldimethylsilyl.

According to some embodiments, $P^2$ is independently selected from optionally substituted —Si($C_1$-$C_6$-alkyl)$_3$, optionally substituted —C(O)—$C_1$-$C_6$-alkyl, optionally substituted —C(O)-aryl, optionally substituted —C(O)—O$C_1$-$C_6$-alkyl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)O$CH_2$-aryl and —$C_1$-$C_4$-alkyl-O—$C_1$-$C_4$-alkyl.

$P^2$ may be independently selected from optionally substituted —Si($C_1$-$C_6$-alkyl)$_3$, optionally substituted —C(O)—O$C_1$-$C_6$-alkyl and optionally substituted —C(O)O$CH_2$-aryl, —C(O)—O-allyl. Preferably, $P^2$ is selected from —C(O)O-tBu, —C(O)O-benzyl and —C(O)O$CH_2$-allyl. Thus, $P^2$ may be —C(O)O$CH_2$-aryl. $P^2$ may be —C(O)O-tBu.

Alternatively, $P^2$ may be independently selected from optionally substituted —C(O)—$C_1$-$C_6$-alkyl and optionally substituted —C(O)-aryl, e.g. $P^2$ may be independently selected from benzoyl and acetyl.

In a further alternative, $P^2$ may be optionally substituted —Si($C_1$-$C_6$-alkyl)$_3$. $P^2$ may be —Si($C_1$-$C_4$-alkyl)$_3$. The alkyl groups may be unsubstituted. $P^2$ may be t-butyldimethylsilyl.

$P^3$ may be independently selected from —C(O)O$C_1$-$C_6$-alkyl, optionally substituted —C(O)O$CH_2$-aryl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl and optionally substituted —Si($C_1$-$C_6$-alkyl)$_3$.

$P^3$ may be independently selected from —C(O)O$C_1$-$C_6$-alkyl, optionally substituted —C(O)O$CH_2$-aryl, —C(O)—O-allyl, optionally substituted —C(aryl)$_3$, and optionally substituted —Si($C_1$-$C_6$-alkyl)$_3$. Preferably, $P^3$ is selected from —C(O)O-tBu, —C(O)O— benzyl and —C(O)O$CH_2$-allyl. Thus, $P^3$ may be —C(O)O$CH_2$-aryl.

Alternatively, $P^3$ may be independently selected from optionally substituted —C(O)—$C_1$-$C_6$-alkyl and optionally substituted —C(O)-aryl, e.g. $P^3$ may be independently selected from benzoyl and acetyl.

In another alternative, $P^3$ is H.

$P^4$ may be independently selected from H, —C(O)O$C_1$-$C_6$-alkyl, optionally substituted —C(O)O$CH_2$-aryl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl and optionally substituted —Si($C_1$-$C_6$-alkyl)$_3$.

Preferably, $P^4$ is H.

It may be that $P^3$ and $P^4$ are each H. It may be that $P^3$ and $P^4$ are each H and $P^2$ is —C(O)O-tBu. It may be that $P^3$ and $P^4$ are each H and $P^2$ is t-butyldimethylsilyl.

According to some embodiments, $P^5$ and $P^6$ are each independently selected from optionally substituted —Si($C_1$-$C_6$-alkyl)$_3$, optionally substituted —C(O)—$C_1$-$C_6$-alkyl, optionally substituted —C(O)-aryl, optionally substituted —C(O)—O$C_1$-$C_6$-alkyl, —C(O)—O— allyl, —C(O)—O—$CH_2$-fluorenyl, optionally substituted —C(aryl)$_3$, optionally substituted —($C_1$-$C_3$-alkylene)-aryl, optionally substituted —C(O)O$CH_2$-aryl and —$C_1$-$C_4$-alkyl-O—$C_1$-$C_4$-alkyl; or $P^5$ and $P^6$ together form a optionally substituted —C($C_1$-$C_4$-alkyl)$_2$-group. $P^5$ and $P^6$ may be the same.

$P^5$ and $P^6$ may each be selected from optionally substituted —Si($C_1$-$C_6$-alkyl)$_3$, optionally substituted —C(O)—O$C_1$-$C_6$-alkyl and optionally substituted —C(O)O$CH_2$-aryl, —C(O)—O-allyl. Preferably, $P^5$ and $P^6$ are each selected from —C(O)O-tBu, —C(O)O— benzyl and —C(O)O$CH_2$-allyl. Thus, $P^5$ and $P^6$ may each be —C(O)O$CH_2$-aryl. $P^5$ and $P^5$ may each be —C(O)O-tBu.

Alternatively, $P^5$ and $P^6$ may each be selected from optionally substituted —C(O)—$C_1$-$C_6$-alkyl and optionally substituted —C(O)-aryl, e.g. $P^5$ and $P^6$ may each be selected from benzoyl and acetyl.

In a further alternative, $P^5$ and $P^6$ may each be optionally substituted —Si($C_1$-$C_6$-alkyl)$_3$. $P^2$ may be —Si($C_1$-$C_4$-alkyl)$_3$. The alkyl groups may be unsubstituted. $P^5$ and $P^6$ may each be t-butyldimethylsilyl.

Preferably, however, $P^5$ and $P^6$ together form a optionally substituted —C($C_1$-$C_4$-alkyl)$_2$-group. It may be that $P^5$ and $P^6$ together form a —C(Me)$_2$-group.

$P^7$ may be independently selected from —C(O)O$C_1$-$C_6$-alkyl, optionally substituted —C(O)O$CH_2$-aryl, —C(O)—O-allyl, —C(O)—O—$CH_2$-fluorenyl, optionally substituted —C(aryl)$_3$, optionally substituted —($C_1$-$C_3$-alkylene)-aryl, optionally substituted —C(O)—$C_1$-$C_6$-alkyl, optionally substituted —C(O)-aryl, —S(O)$_2$—$C_1$-$C_6$-alkyl, optionally substituted —S(O)$_2$-aryl and optionally substituted —Si($C_1$-$C_6$-alkyl)$_3$.

$P^7$ may be independently selected from —C(O)O$C_1$-$C_6$-alkyl, optionally substituted —C(O)O$CH_2$-aryl, —C(O)—O-allyl, optionally substituted —C(aryl)$_3$, and optionally substituted —Si($C_1$-$C_6$-alkyl)$_3$. Preferably, $P^7$ is selected from —C(O)O-tBu, —C(O)O— benzyl and —C(O)O$CH_2$-allyl. Thus, $P^7$ may be —C(O)O$CH_2$-aryl.

Alternatively, $P^7$ may be independently selected from optionally substituted —C(O)—$C_1$-$C_6$-alkyl and optionally substituted —C(O)-aryl, e.g. $P^7$ may be independently selected from benzoyl and acetyl.

In another alternative, $P^7$ is H.

Likewise, $P^8$ may be independently selected from H, —C(O)O$C_1$-$C_6$-alkyl, optionally substituted —C(O)O$CH_2$-aryl, —C(O)—O-allyl, —C(O)—O—$CH_2$-fluorenyl, optionally substituted —C(aryl)$_3$, optionally substituted —($C_1$-$C_3$-alkylene)aryl, optionally substituted —C(O)—$C_1$-$C_6$-alkyl, optionally substituted —C(O)-aryl, optionally substituted —S(O)$_2$-aryl and optionally substituted —Si($C_1$-$C_6$-alkyl)$_3$.

Preferably, $P^8$ is H.

It may be that $P^7$ and $P^8$ are each H. It may be that $P^7$ and $P^8$ are H and $P^5$ and $P^6$ together form a —C(Me)$_2$-group.

The group optionally substituted —Si($C_1$-$C_6$-alkyl)$_3$ may be a —Si($C_1$-$C_4$-alkyl)$_3$ group. The group is (i.e. the alkyl groups are) preferably unsubstituted. Illustrative examples include triethylsilyl and t-butyl-dimethylsilyl.

The group optionally substituted —C(O)—$C_1$-$C_6$-alkyl may be a —C(O)—$C_1$-$C_6$-alkyl group. The group (i.e. the alkyl group) is preferably unsubstituted. Illustrative examples include acetyl and propionyl.

The group optionally substituted —C(O)-aryl may be a —C(O)-phenyl group. The group (i.e. the phenyl group) is preferably unsubstituted. Illustrative examples include benzoyl.

The group optionally substituted —C(O)—O$C_1$-$C_6$-alkyl may be a —C(O)—O$C_1$-$C_4$-alkyl group. The group (i.e. the alkyl group) is preferably unsubstituted. Illustrative examples include —C(O)—O-methyl and —C(O)—O-ethyl. A particularly preferred example is C(O)OtBu.

The group optionally substituted —($C_1$-$C_3$-alkylene)-aryl is preferably an optionally substituted benzyl group. Illustrative examples include benzyl, phenethyl, 4-methoxy benzyl, 4-nitrobenzyl, 4-bromobenzyl, 2,3-dimethoxybenzyl and 2,4-dimethoxybenzyl.

The group optionally substituted —C(O)OCH$_2$-aryl is preferably an optionally substituted —C(O)Obenzyl group. Illustrative examples include —C(O)Obenzyl and —C(O)O-(4-methoxybenzyl).

The group optionally substituted —C$_1$-C$_4$-alkyl-O—C$_1$-C$_4$-alkyl may be a —C$_1$-C$_2$-alkyl-O—C$_1$-C$_2$-alkyl group. The group is (i.e. the alkyl groups are) preferably unsubstituted. Illustrative examples include methoxy-methyl (MOM) and 2-methoxy-ethoxy-methyl (MEM).

The group optionally substituted —S(O)$_2$—C$_1$-C$_6$-alkyl may be a —S(O)$_2$—C$_1$-C$_4$-alkyl group. The group (i.e. the alkyl group) is preferably unsubstituted. Illustrative examples include methanesulfonate.

The group optionally substituted —S(O)$_2$-aryl may be a —S(O)$_2$-phenyl group. Illustrative examples include phenylsulfonate, 4-methylphenylsulfonate and 4-nitro phenylsulfonate.

The group optionally substituted —C(aryl)$_3$ may be a —C(phenyl)$_3$ group. Illustrative examples include trityl.

Where two or more of P$^2$, P$^3$ and P$^4$ or P$^5$, P$^6$, P$^7$ and P$^8$ are protecting groups, the deprotection step may comprise two or three individual deprotection reactions. This is the case where two or three different protecting groups are used and where those two or three protecting groups cannot be removed under the same conditions.

It may be, however, that the deprotection step comprises a single deprotection reaction in which all protecting groups are removed. Thus, it may be that P$^2$ and P$^3$ are protecting groups which can be removed under the same conditions. It may be that P$^2$ and P$^3$ are the same. Likewise, it may be that P$^5$ and P$^6$ are protecting groups which can be removed under the same conditions. It may be that P$^5$ and P$^6$ are the same.

Throughout this specification, 'diastereomerically enriched form' and 'substantially diastereomerically pure form' means a diastereoisomeric purity of greater than 95%. 'Diastereomerically enriched form' and 'substantially diastereomerically pure form' may mean a diastereoisomeric purity of greater than 98%, greater than 99% or greater than 99.5%.

Any of the aforementioned alkyl and aryl (e.g. phenyl, including the phenyl groups in benzyl groups) groups, are optionally substituted, where chemically possible, by 1 to 3 substituents which are each independently at each occurrence selected from the group consisting of: oxo, =NR$^a$, =NOR$^a$, halo, nitro, cyano, NR$^a$R$^a$, NR$^a$S(O)$_2$R$^a$, NR$^a$CONR$^a$R$^a$, NR$^a$CO$_2$R$_a$, OR$^a$; SR$^a$, SOR$^a$, SO$_3$R$^a$, SO$_2$R$^a$, SO$_2$NR$^a$R$^a$, CO$_2$R$_a$ C(O)R$_a$, CONR$^a$R$^a$, C$_2$-C$_4$-alkenyl, C$_2$-C$_4$-alkenyl, and C$_1$-C$_4$ haloalkyl; wherein R$^a$ is independently at each occurrence selected from H, C$_1$-C$_4$ alkyl and C$_1$-C$_4$ haloalkyl.

It may be that any of the aforementioned alkyl groups is unsubstituted.

It may be that any of the aforementioned aryl groups (e.g. phenyl, including the phenyl groups in benzyl groups) are optionally substituted, where chemically possible, by 1 to 3 substituents which are each independently at each occurrence selected from the group consisting of: halo, nitro, cyano, NR$^a$R$^a$, NR$^a$S(O)$_2$R$^a$, NR$^a$CONR$^a$R$^a$, NR$^a$CO$_2$R$^a$, OR$^a$; SR$^a$, SOR$^a$, SO$_3$R$^a$, SO$_2$R$^a$, SO$_2$NR$^a$R$^a$, CO$_2$R$^a$ C(O)R$^a$, CONR$^a$R$^a$, C$_2$-C$_4$-alkenyl, C$_2$-C$_4$-alkenyl, and C$_1$-C$_4$ haloalkyl; wherein R$^a$ is independently at each occurrence selected from H, C$_1$-C$_4$ alkyl and C$_1$-C$_4$ haloalkyl.

It may be that any of the aforementioned aryl (e.g. phenyl, including the phenyl groups in benzyl groups) groups are optionally substituted by 1 to 3 substituents which are each independently at each occurrence selected from the group consisting of: halo, nitro, OR$^a$; C$_1$-C$_4$-alkyl, C$_1$-C$_4$ haloalkyl; wherein R$^a$ is independently at each occurrence selected from H, C$_1$-C$_4$ alkyl and C$_1$-C$_4$ haloalkyl.

Aryl groups have from 6 to 20 carbon atoms as appropriate to satisfy valency requirements. Aryl groups are carbocyclic groups which satisfy the Huckel rule (i.e. they contain a carbocyclic ring system containing 2(2n+1)π electrons). Aryl groups may be optionally substituted phenyl groups, optionally substituted biphenyl groups, optionally substituted naphthalenyl groups or optionally substituted anthracenyl groups. Equally, aryl groups may include non-aromatic carbocyclic portions. Preferably an aryl group is an optionally substituted phenyl group.

Alkyl groups may be straight chain or branched. Thus, for example, a C4 alkyl group could be n-butyl, i-butyl or t-butyl.

Step a) of the first, second and third aspects may be conducted in an organic solvent (S1). Organic solvents include but are not limited to ethers (e.g. tetrahydrofuran, dioxane, diethyl ether, methyl-t-butylether); ketones (e.g. acetone and methyl isobutyl ketone); halogenated solvents (e.g. dichloromethane, chloroform and 1,2-dichloroethane); and amides (e.g. DMF, NMP); or mixtures thereof. Where step a) is conducted in the presence of a Grignard reagent, the organic solvent is preferably an ether. Most preferably, the solvent is tetrahydrofuran.

Where step a) of the first aspect is conducted in the present of a nitrogen base, the organic solvent is most preferably a halogenated solvent or an amide.

The reaction is typically conducted at a suitable temperature, e.g from about −5° C. to about 40° C. Preferably, the reaction temperature is about 25° C. to about 30° C. The reaction may be allowed to stir for a period of time from about 15 mins to about 16 h and preferably from about 30 mins to about 60 mins.

The processes of the invention may also involve deprotection of the hydroxy and amino protecting groups.

It may be that the deprotection step (step b) is carried out without purifying the product of step a).

Where a protecting group is acid sensitive (e.g. trityl, C(O)OtBu, MOM, MEM, 2,4-dimethoxybenzyl, 2,3-dimethoxybenzyl, —C(Me)$_2$-) the deprotection step can be conducted using a suitable acid. The acid may be a Bronsted acid (e.g. TFA, phosphoric acid, HCl, or formic acid) or a Lewis acid (e.g. ZnBr$_2$, CeCl$_3$). Lewis acids (e.g. ZnBr$_2$) are less preferred. HCl is likewise less preferred. Preferably, the acid is TFA.

Where a protecting group is base sensitive, e.g. acetyl, benzoyl, the deprotection step can be conducted using a suitable base, e.g. aqueous NH$_3$ or aqueous NaOH. Base sensitive groups may be less preferred.

Where a protecting group is a silyl group (e.g. triethylsilyl or t-butyldimethylsilyl, the deprotection step can be conducted using a suitable acid (e.g. TFA) or using a suitable fluorine source (e.g. tetrabutylammonium fluoride, fluorosilicic acid, HF).

Where a protecting group is a benzyl group or a C(O)Obenzyl group, the deprotection step can be conducted using H2 and a suitable catalyst (e.g. Pd/C). Such protecting groups may be less preferred.

Where a protecting group is a 4-methoxy-benzyl, 2,3-dimethoxybenzyl, 2,4-dimethoxybenzyl or C(O)O-(4-methoxybenzyl) the deprotection step can be performed using a suitable oxidizing agent (e.g. meta-chloroperbenzoic acid).

Where a protecting group is —C(O)—O-allyl, the deprotection step can be performed using (PPh$_3$)$_4$Pd.

Where a protecting group is —C(O)—O—CH$_2$-fluorenyl, the deprotection step can be performed using piperidine.

The deprotection step may be conducted in an organic solvent or a mixture thereof. Exemplary organic solvents include, but are not limited to halogenated solvents (e.g.

dichloromethane, chloroform, dichloroethane); alcohols (e.g. methanol, ethanol, isopropanol) and ethers (e.g. tetrahydrofuran, diethyl ether).

Where the deprotection step is carried out in the presence of an acid (e.g. TFA, the organic solvent is preferably a halogenated solvent, e.g. dichloromethane.

The deprotection reaction may be carried out at a temperature in the range of, for example −10° C. to about 30° C., e.g. to about 10° C. A convenient temperature to carry out the reaction is −5° C. to 5° C. The reaction may be allowed to stir for a period of time from about 15 mins to about 16 hours and preferably from about 1 hour to about 4 hours, and more preferably from about 2 hours to about 3 hours.

Where step b) is achieved using a $C_1$-$C_4$-alcohol and/or water (e.g. a mixture of isopropyl alcohol (IPA) and water), the reaction mixture may be heated, e.g. to a temperature from 30° C. to 90° C. or to a temperature from 60° C. to 85° C.

Where, the deprotection is performed in the presence of an acid (e.g. TFA), isolation of the product obtained after the deprotection is typically done by quenching the excess acid used in deprotection step and extracting the product with a water immiscible organic solvent and recovering the product by evaporation of the organic solvent.

Examples of water immiscible organic solvents useful in extraction include esters such as ethyl acetate, methyl acetate, isopropyl acetate and the like; chlorinated solvents such as dichloromethane, chloroform and the like; aromatic hydrocarbon solvents such as toluene, xylene and the like; preferably ethyl acetate.

In certain embodiments, it may still be desirable to purify the ProTide obtained from the process of the first aspect of the invention. Likewise, it may still be desirable to purify the compound of formula IIa obtained from the process of the fourth aspect of the invention. Methods of purification are well known to those skilled in the art and include chromatography (e.g. column chromatography), recrystallisation and distillation. In other embodiments, no purification is necessary.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

The following abbreviations are used throughout this specification:

ACN—acetonitrile AlBBr—acetoxy isobutyryl bromide
BOC—t-butylcarbonate DCM—dichloromethane
DMAP—N,N-dimethyl-4-aminopyridine DMF—N,N-dimethylformamide
eq.—molar equivalents FUDR—5-fluoro-2'-deoxyuridine
IPA—isopropyl alcohol MEM—2-methoxyethoxymethyl
MOM—methoxymethyl MTBE—methyl-t-butylether
NMP—N-methyl-2-pyrrolidone Np—1-naphthyl
PTSA—para-toluene sulfonic (tosic) acid RT—room temperature
TBAF—tetrabutylammonium fluoride TBDMS—tert-butyldimethylsilyl
TEA—triethylamine Tf—trifluoromethylsulfonate (triflate)
TFA—trifluoroacetic acid THF—tetrahydrofuran V is used to denote volume (in mL) per weight (in g) starting material. So if there was 1 g of starting material, 10 V would mean 10 mL of the indicated liquid.

EXAMPLES

The present invention is further illustrated by the following examples, which are provided by way of illustration only and should not be construed to limit the scope of the invention.

Example 1: Preparation of Diastereoisomeric Mixture of 2-[(2,3,4,5,6-pentafluorophenoxy)-phenoxyphosphoryl amino] propionic Acid Benzyl Ester 5 (an Illustrative Example of a Compound of Formula IIb)

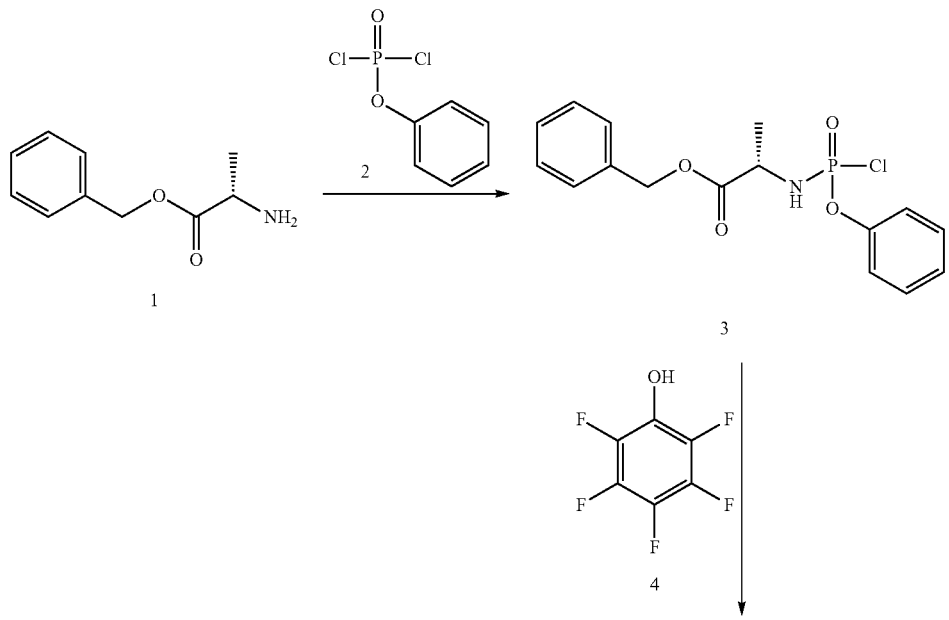

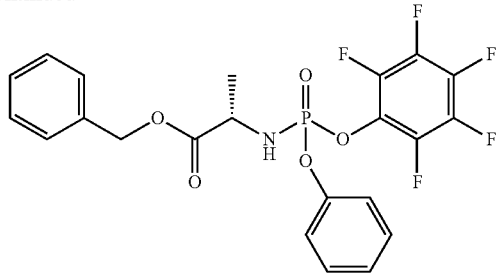

5

To a stirred mixture of L-alanine benzyl ester hydrochloride 1 (100 g) in methylene chloride (1 L) was added phenyl dichlorophosphate 2 (77 mL) at 25-35° C. and the resulting mixture was cooled to −70° C. to −78° C., triethylamine (130.5 mL) was added and the mixture was stirred for 1 hour at same temperature. Reaction mass temperature was raised to 25-35° C. and allowed to stir for 2 hours. After reaction completion, concentrated the reaction mass under vacuum at below 35° C. to obtain residue. To the obtained residue was added diisopropyl ether (2 L) at 25-35° C. and stirred for 30 min at same temperature. Filtered the reaction mass and washed with diisopropyl ether (500 mL) followed by concentrating the filtrate under vacuum at below 35° C. to obtain phenyl-(benzoxy-L-alaninyl)-phosphorochloridate 3. The obtained compound was dissolved in methylene chloride (1 L) at 25-35° C. and cooled to −5° C. to −10° C. To the reaction mass pentafluorophenol 4 (85.5 g), triethylamine (65.2 mL) were added at same temperature and stirred for 2 hrs. After reaction completion, concentrated the reaction mass under vacuum at below 35° C. and charged ethyl acetate (1 L) at 25-35° C. and stirred for 30 min at same temperature. Filtered the solids and washed with ethyl acetate (1 L). To the filtrate was given water (1 L), 10% sodium carbonate (2×1 L), brine (1 L) washings and dried the organic layer with anhydrous sodium sulphate, concentrated under vacuum at 35-45° C. to obtain diastereoisomeric mixture of title compound 5 as a white colored semi solid.

Yield: 210 g

Chiral Purity by HPLC (% area): 33.74:66.26% ($R_P:S_P$)

Example 2: Separation of $S_P$-Diastereoisomer of 2-[(2,3,4,5,6-pentafluorophenoxy)-phenoxy-phosphoryl amino] propionic Acid Benzyl Ester 5 (an Illustrative Example of a Compound of Formula IIb)

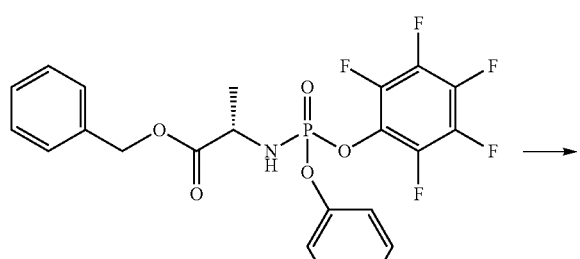

5 (Sp and Rp mixture)

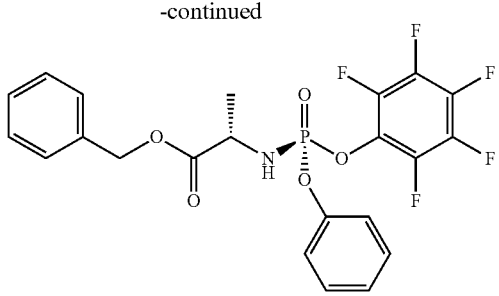

5 (Sp-diastereomer)

+

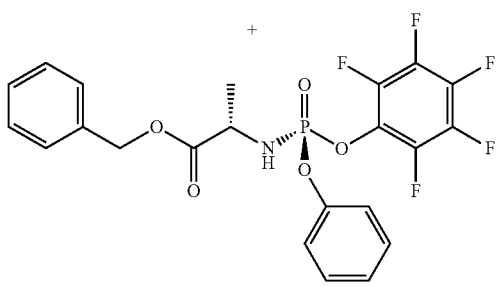

5 (Rp-diastereomer)

To a diastereoisomeric mixture of compound 5 (210 g; $R_P:S_P$—33.74:66.26%) was charged 20% ethyl acetate in hexane (1.2 L) at 25-35° C. and stirred for 1 hrs. Filtered the solids and washed with 20% ethyl acetate in hexane (300 mL) to obtain a mixture of diastereoisomeric mixture of compound 5.

Yield: 112 g

Chiral Purity by HPLC (% area): 22.13:77.87% ($R_P:S_P$)

Filtrate was concentrated under vacuum to obtain a diastereoisomeric mixture of compound of 5 (75 g; $R_P:S_P$—65.43:34.57%).

To a diastereoisomeric mixture of the compound of formula IIb (112 g; $R_P:S_P$—22.13:77.87%) was charged 20% ethyl acetate in hexane (1.2 lit) at 25-35° C. and stirred for 1 hrs. Filtered the solids and washed with 20% ethyl acetate in hexane (300 ml) to obtain substantially pure $S_P$-diastereoisomer of compound 5.

Yield: 80 g

Chiral Purity by HPLC (% area): 0.20:99.80% ($R_P:S_P$)

$^1$H NMR (300 MHz, DMSO-$d_6$): 7.18-7.41 (m, 10H), 6.91-6.99 (d, 1H), 5.10 (s, 2H), 4.01-4.11 (m, 1H), 1.30-1.32 (d, 3H)

ESI-MS (m/z): 524 (M+1)

Filtrate was concentrated under vacuum to obtain a diastereoisomeric mixture of compound 5 (28 g; $R_P:S_P$—80.77:19.23%).

Example 3: Enrichment of 2-[(2,3,4,5,6-pentafluorophenoxy)-phenoxy-phosphoryl amino] propionic Acid Benzyl Ester 5 S-Isomer (an Illustrative Example of a Compound of Formula IIb)

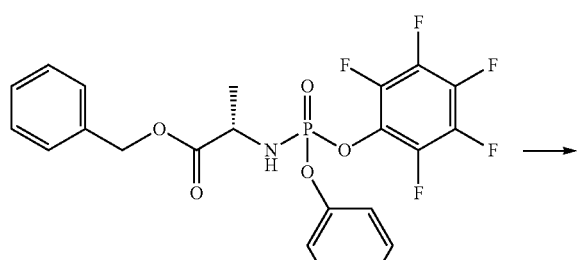

5 (Sp and Rp mixture)

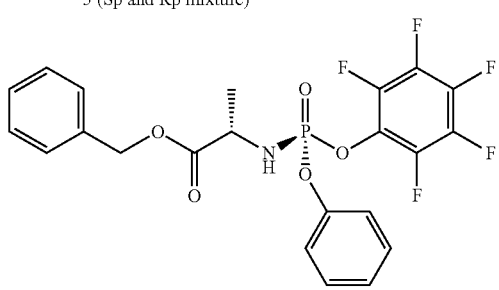

5 (Sp-diastereomer)

To a stirred solution of 2-[(2,3,4,5,6-pentafluorophenoxy)-phenoxy-phosphoryl amino] propionic acid benzyl ester 5 (75 g; $R_P$:$S_P$—65.43:34.57%) in 20% ethyl acetate in hexane (1.1 L), triethyl amine (7.5 mL) was added at 25-35° C. and stirred for 6 hrs at same temperature. After reaction completion, reaction mass was quenched in to a water (750 mL) and extracted with ethyl acetate (750 mL). Organic layer was dried with anhydrous sodium sulphate and concentrated under vacuum to afford title compound as a solid.

Yield: 45 g

Chiral Purity by HPLC (% area): 91.29:8.71% ($S_P$:$R_P$)

To the above obtained $R_p$ and $S_p$-diastereoisomeric mixture of 2-[(2,3,4,5,6-pentafluorophenoxy)-phenoxy-phosphoryl amino] propionic acid benzyl ester 5 (45 g; $R_P$:$S_P$—8.71:91.29%) was slurred in 20% ethyl acetate in hexane (1.1 L) at 25-30° C. and stirred for 1 hr at same temperature. Filtered the solid and washed with 20% ethyl acetate in hexane (225 ml) to obtain $S_p$-diastereoisomer of the title compound as a solid.

Yield: 19 g

Chiral Purity by HPLC (% area): 99.92:0.08% ($S_P$:$R_p$)

Example 4: Preparation of Diastereoisomeric Mixture of 2-[(4-nitrophenoxy)-phenoxy-phosphorylamino] propionic Acid Benzyl Ester 7 (an Illustrative Example of a Compound of Formula IIb

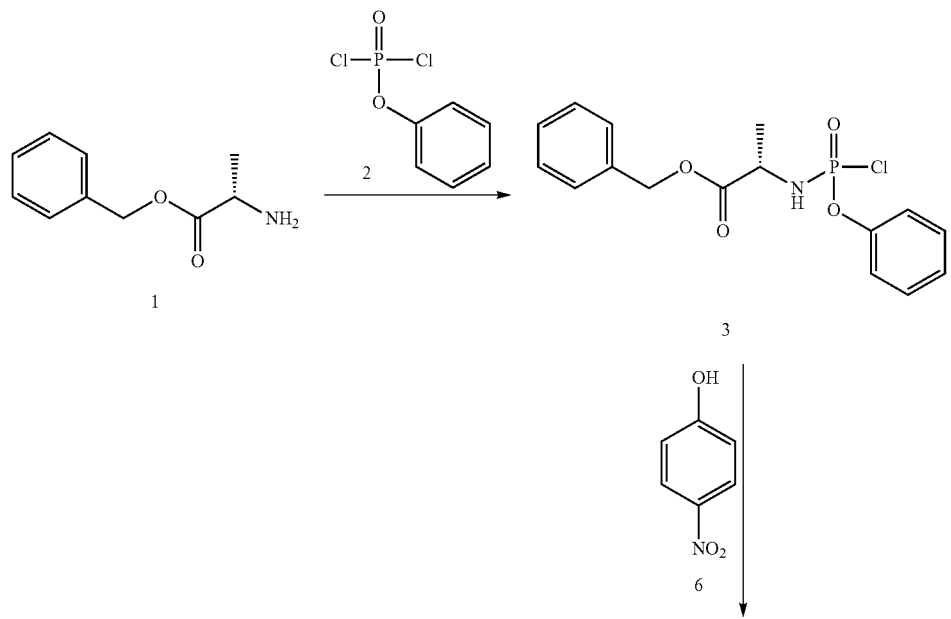

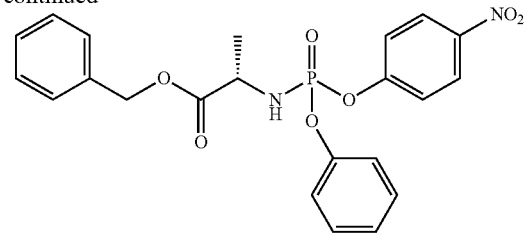

7 (Sp and Rp mixture)

To a stirred mixture of L-alanine benzyl ester hydrochloride 1 (50 g) in methylene chloride (500 mL) was added phenyl dichlorophosphate 2 (54 g) at 25-35° C. and the resulting mixture was cooled to −70° C. to −78° C., added triethyl amine (65.2 mL) and stirred for 1 hour at same temperature. Reaction mass temperature was raised to 25-35° C. and allowed to stir for 2 hrs. After reaction completion, concentrated the reaction mass under vacuum at below 35° C. to obtain residue. To the obtained residue was added diisopropyl ether (1 L) at 25-35° C. and stirred for 30 min at same temperature. Filtered the reaction mass and washed with diisopropyl ether (250 mL) followed by concentrating the filtrate under vacuum at below 35° C. to obtain phenyl-(benzoxy-L-alaninyl)-phosphorochloridate 3. The obtained compound was dissolved in methylene chloride (500 mL) at 25-35° C. and cooled to −5° C. to −10° C. To the reaction mass 4-nitrophenol 6 (27.5 g), triethyl amine (65.2 mL) was added at same temperature and stirred for 2 hrs. After reaction completion, concentrated the reaction mass under vacuum at below 35° C. and charged ethyl acetate (500 mL) at 25-35° C. and stirred for 30 min at same temperature. Filtered the solids and washed with ethyl acetate (500 mL). To the filtrate was given water (500 mL), 10% sodium carbonate (2×500 mL), brine (500 mL) washings and dried the organic layer with anhydrous sodium sulphate, concentrated under vacuum at 35-40° C. to obtain diastereoisomeric mixture of title compound 7 as a thick oily liquid.

Yield: 90 g

Chiral Purity by HPLC (% area): 45.6:54.94% ($R_P$:$S_P$)

The above obtained diastereoisomeric mixture of 2-[(4-nitrophenoxy)-phenoxy-phosphorylamino] propionic acid benzyl ester 7 (40 g; $R_p$:$S_p$—45.6:54.94%) was separated in to pure $S_p$ and $R_p$ diastereoisomers by preparative HPLC and concentrated the pure fractions under vacuum to obtain $S_p$ and $R_p$ diastereoisomers separately.

Yield: $S_p$-diastereoisomer: 8 g, $^1$H NMR (300 MHz, CDCl$_3$): 8.15-8.19 (d, 2H), 7.15-7.37 (m, 12H), 5.12 (s, 2H), 4.02-4.24 (m, 2H), 1.39-1.42 (d, 3H)

ESI-MS (m/z): 479 (M+Na)

$R_p$-diastereoisomer: 6 g, $^1$H NMR (300 MHz, CDCl$_3$): 8.08-8.13 (d, 2H), 7.15-7.34 (m, 12H), 5.10 (s, 2H), 4.48-4.56 (m, 1H), 4.11-4.20 (m, 1H), 1.39-1.41 (d, 3H)

ESI-MS (m/z): 457 (M+1)

$S_p$ and $R_p$-diastereoisomers mixture: 20 g

Example 5—Preparation of (Sp)-2-[(2,3,4,5,6-pentafluorophenoxy)-phenoxy-phosphoryl amino] propionic Acid Benzyl Ester 5 (an Illustrative Example of a Compound of Formula IIb)

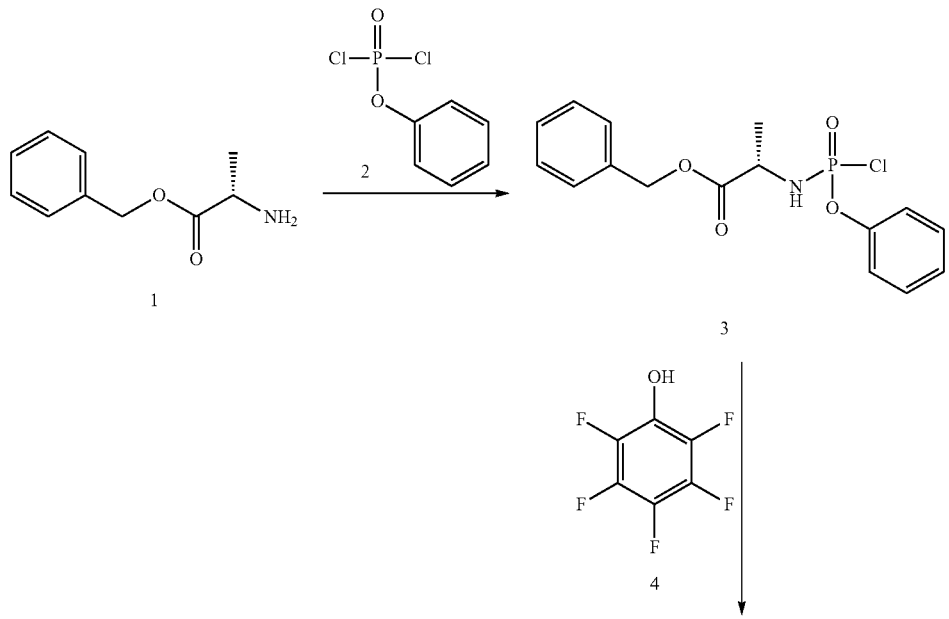

5 (Sp) ← 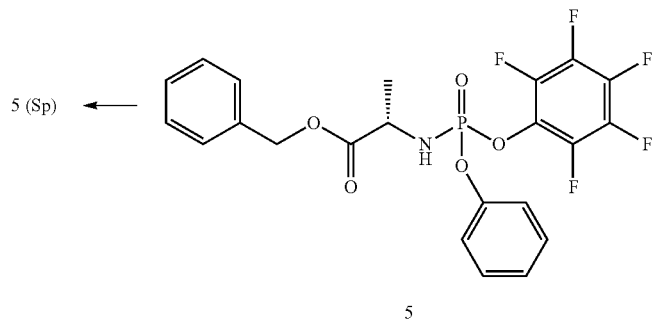

5

To a stirred mixture of L-Alanine Benzyl ester. HCl 1 (100 g) in 1000 mL of methylene dichloride was added phenyl dichlorophosphate 2 (97.8 g) into reaction mass at 30° C. The mixture was cooled to −20° C. and triethylamine (93.8 g) was added slowly, maintaining the temperature at −20° C. The reaction was stirred for 1 h at −20° C., then warmed to 10° C. (10±5) and stirred for a further 1.5 h.

A solution of pentafluorophenol 4 (85.3 g) in 100 mL of methylene dichloride was slowly added at 10° C. followed by trimethylamine (46.8 g) which is added slowly, maintaining the temperature at 10° C. Slowly add 46.9 g of triethylamine into reaction mass at 10° C. (10±5) under nitrogen atmosphere. The mixture was stirred for 2 h at 10° C. before being quenched by slow addition of 0.5 N HCl solution, maintaining the temperature at 10° C. After warming to room temperature the mixture was separated and the organics was washed with a saturated bicarbonate solution, distilled water and brine before being concentrated in vacuo.

The crude mixture was suspended in 1500 mL of 20% ethyl acetate in n-heptane at 25° C. Triethylamine (12.2 g) was added and the mixture was stirred at 25° C. The mixture was filtered and the solid dissolved in 2500 mL ethyl acetate which was washed with water and brine and concentrated in vacuo. The solid was suspended in 1200 mL of 20% ethyl acetate in n-heptane, stirred for 45-60 min and filtered. The material was dried under vacuum to provide the desired product 5-(Sp). Yields are in the range 40 to 80% and the diastereoisomeric purity is over 99%.

Example 6: Preparation of Diastereoisomeric Mixture of 2-[(2,3,4,5,6-pentafluorophenoxy)-naphth-1-oxy-phosphoryl amino] propionic Acid Benzyl Ester 12 (an Illustrative Example of a Compound of Formula IIa)

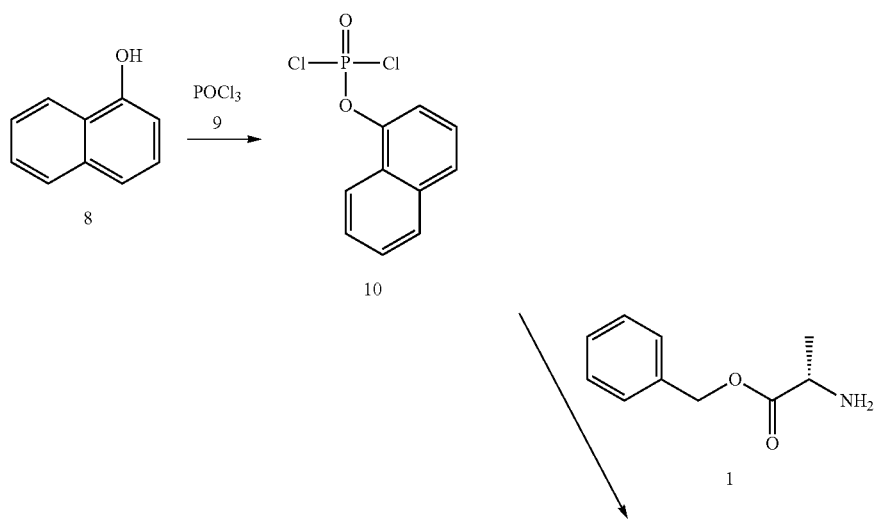

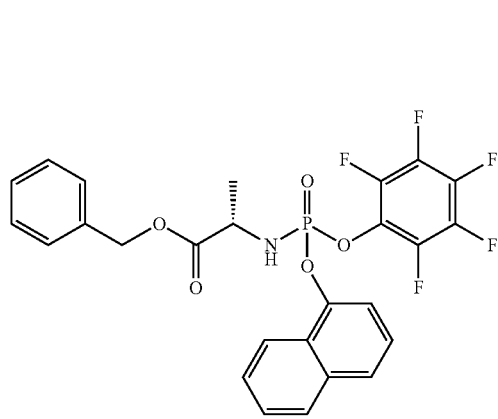

12

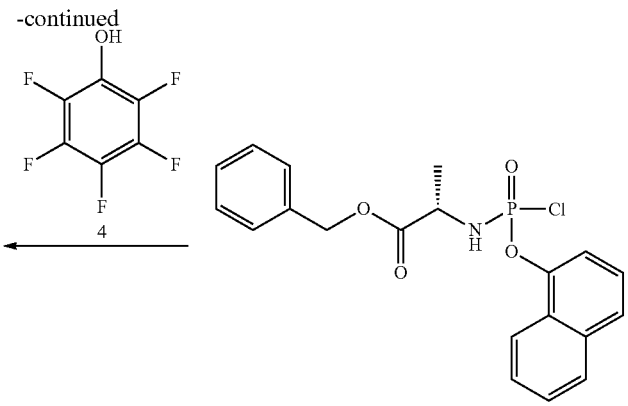

11

Alpha-naphthol 8 (100 g) was dissolved in DCM (1 L) at 25° C. and POCl₃ 9 (1.1 eq) was added at 25° C. and stirred for 10 min before the mixture was cooled to −70° C. and stirred for 10 min. Triethylamine (1.1 eq.) was added slowly maintaining the temperature at below −70° C. and the mixture was stirred for 1 h at −70° C. The mixture was warmed to 25° C. and stirred for 1 h before being cooled to −50° C. L-alanine benzyl ester 1 (HCl salt; 1 eq.) was added to the mixture which stirred for 10 min before triethylamine (2.2 eq) in DCM (200 mL) was added at −50° C. over 30 minutes. The mixture was stirred for 1 h at −50° C. before being warmed to 25° C. and stirred for a further 1 h. The mixture was cooled to −10° C. and stirred for 10 min before pentafluorophenol 4 in DCM (200 mL) was added to the reaction mass slowly at below −10° C. The mixture was stirred at −10° C. for 10 min before triethylamine (1.1 eq.) was added over 30 min at −10° C. The mixture was stirred at −10° C. for 1 h before the mixture was warmed to 0° C. Water (1 L) was added and the mixture was stirred for 30 min at 0° C. The mixture was warmed to 25° C. and stirred for 5-10 min before the organic layer was separated. The aqueous layer was extracted with DCM (500 mL). The combined organic layers were washed with 7% sodium bicarbonate solution (2×1 L) and the organic layer was dried over anhydrous sodium sulphate before being concentrated in vacuo. 50% IPA/water (2.4 L) was added to the crude compound and stirred for 1 h at 25° C. The solid compound was filtered and the wet cake was washed with 50% IPA/water (500 mL) before being dried in vacuo. Again 50% IPA/water (2.4 L) was added to the crude compound and stirred for 1 h at 25° C. before being filtered and the wet cake was again washed with 50% IPA/water (500 mL) before being dried in vacuo. The semi-dried compound was washed with cyclohexane (10 v/w) at 25-30° C. for 1 h before the solid compound was washed with cyclohexane (2 L) and the wet compound 12 was dried under vacuum at 55-60° C. ° C. for 12 h Results:
Weight of the compound: 252 g
Overall yield: 66%
HPLC purity: 98.31% (diastereoisomeric ratio is 1:1)
$^{31}$P NMR (202 MHz, CDCl₃): $\delta_P$-1.35, -1.41; $^1$H NMR (500 MHz, CDCl₃): $\delta_H$ 8.13-8.10 (1H, m, H—Ar), 7.90-7.88 (1H, m, H—Ar), 7.73 (1H, apparent d, J=8.5 Hz, H—Ar), 7.62-7.55 (3H, m, H—Ar), 7.45-7.41 (1H, m, H—Ar), 7.36-7.28 (5H, m, H—Ar), 5.01 (1H, apparent s, CH₂Ph), 5.12 (1H, q, J=12.5 Hz, CH₂Ph), 4.38-4.31 (1H, m, NHCHCH3), 4.17-4.08 (1H, m, NHCHCH₃), 1.49, 1.47 (3H, 2×d, J=3.5 Hz, NHCHCH₃); MS (ES+) m/z: 574 (M+Na⁺, 100%), Accurate mass: C₂₆H₁₉F₅NO₅P required 551.40 found 574.05 (M+Na⁺); Reverse-phase HPLC, eluting with H₂O/MeOH in 20/80 in 35 min, F=1 mL/min, λ=254, two peaks for two diastereoisomers with $t_R$=12.96, 14.48 min.

The diastereoisomers of compound 12 were separated by HPLC with Biotage Isolera using C18 SNAP Ultra (30 g) cartridge with a mixture of MeOH/H₂O (70%/30%) as an eluent to give: the fast eluting isomer (believed to be the Rp diastereoisomer) and the slow eluting isomer (believed to be the Sp diastereoisomer)

Note: Isomers are named as fast eluting (FE) and slow eluting (SE) based on retention time on C18 (reversed phase) cartridge and HPLC analytical column.

Fast eluting isomer (believed to be the Rp diastereoisomer): $^{31}$P NMR (202 MHz, CDCl₃): $\delta_P$-1.41; $^1$H NMR (500 MHz, CDCl₃): $\delta_H$ 8.02 (1H, dd, J=7.0, 2.0 Hz, H—Ar), 7.79 (1H, dd, J=6.5, 3.0 Hz, H—Ar), 7.64 (1H, d, J=8.5 Hz, H—Ar), 7.53-7.45 (3H, m, H—Ar), 7.33 (1H, t, J=8.0 Hz, H—Ar), 7.28-7.23 (5H, m, H—Ar), 5.09 (s, 2H, CH₂Ph), 4.29-4.21 (1H, m, NHCHCH₃), 4.02-3.97 (1H, m, NHCHCH₃), 1.38 (3H, d, J=7.0 Hz, NHCHCH₃); MS (ES+) m/z: MS (ES+) m/z: 574 (M+Na⁺, 100%), Accurate mass: C₂₆H₁₉F₅NO₅P required 551.40 found 574.05 (M+Na⁺); Reverse-phase HPLC, eluting with H₂O/MeOH in 20/80 in 35 min, F=1 mL/min, λ=254, $t_R$=12.96.

Slow eluting isomer (believed to be the Sp diastereoisomer): $^{31}$P NMR (202 MHz, CDCl₃): $\delta_P$-1.36; $^1$H NMR (500 MHz, CDCl₃): $\delta_H$ 8.14-8.11 (1H, m, H—Ar), 7.90-7.87 (1H, m, H—Ar), 7.74 (1H, d, J=8.0 Hz, H—Ar), 7.60 (1H, d, J=8.0 Hz, H—Ar), 7.58-7.55 (2H, m, H—Ar), 7.44 (1H, t, J=8.0 Hz, H—Ar), 7.34-7.30 (5H, m, H—Ar), 5.12 (2H, q, J=12.5 Hz, CH₂Ph), 4.35-4.29 (1H, m, NHCHCH₃), 4.04-4.00 (1H, m, NHCHCH3), 1.48 (3H, d, J=7.0 Hz, NHCHCH3); MS (ES+) m/z: MS (ES+) m/z: 574 (M+Na⁺, 100%), Accurate mass: C₂₆H₁₉F₅NO₅P required 551.40 found 574.05 (M+Na⁺); Reverse-phase HPLC, eluting with H₂O/MeOH in 20/80 in 35 min, F=1 mL/min, λ=254, $t_R$=14.48.

Example 7: Enrichment of $S_p$-Diastereoisomer of 2-[(2,3,4,5,6-pentafluorophenoxy)-naphth-1-oxy-phosphoryl amino] propionic Acid Benzyl Ester 12 Sp Isomer (an Illustrative Example of a Compound of Formula IIb)

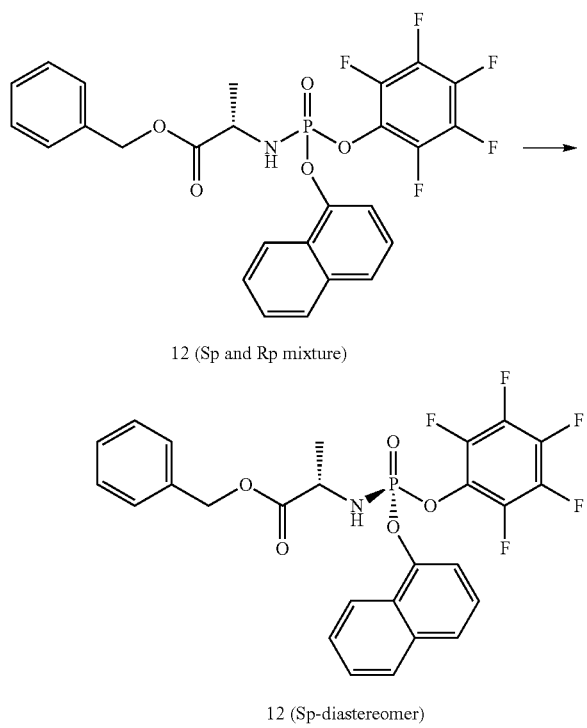

12 (Sp and Rp mixture)

12 (Sp-diastereomer)

A 1:1 diastereoisomeric mixture of compound 12 (25 g) was dissolved in 10% MTBE/n-Hexane (500 mL) and triethylamine (2.5 mL) was added to the reaction mass at 25° C. The mixture was stirred for 80 h at 30° C. The mixture was filtered and the wet cake was washed with 10% MTBE/n-hexane (75 mL) before being dried in vacuo 30 min. 50% IPA/water (200 mL) was added to above crude compound and stirred for 1 h at 25-35° C. before being filtered. The wet cake was washed with 50% IPA/water (100 mL) before being dried in vacuo at 55-60° C. ° C. for 12 h Result:
Wt. of the compound: 17 g
Yield: 68%
HPLC purity: 97.66%
Slow eluting isomer (believed to be Sp-diastereoisomer): $^{31}$P NMR (202 MHz, CDCl$_3$): $\delta_P$ −1.36; $^1$H NMR (500 MHz, CDCl$_3$): $\delta_H$ 8.14-8.11 (1H, m, H—Ar), 7.90-7.87 (1H, m, H—Ar), 7.74 (1H, d, J=8.0 Hz, H—Ar), 7.60 (1H, d, J=8.0 Hz, H—Ar), 7.58-7.55 (2H, m, H—Ar), 7.44 (1H, t, J=8.0 Hz, H—Ar), 7.34-7.30 (5H, m, H—Ar), 5.12 (2H, q, J=12.5 Hz, CH$_2$Ph), 4.35-4.29 (1H, m, NHCHCH$_3$), 4.04-4.00 (1H, m, NHCHCH$_3$), 1.48 (3H, d, J=7.0 Hz, NHCHCH$_3$); MS (ES+) m/z: MS (ES+) m/z: 574 (M+Na$^+$, 100%), Accurate mass: C$_{26}$H$_{19}$F$_5$NO$_5$P required 551.40 found 574.05 (M+Na$^+$); Reverse-phase HPLC, eluting with H$_2$O/MeOH in 20/80 in 35 min, F=1 mL/min, λ=254, $t_R$=14.48.

The stereochemistry (Rp vs Sp) of the two compound 12 isomers described above has been assigned tentatively on the basis of comparison of $^{31}$P chemical shift, 1H NMR spectra, and HPLC retention times of the NUC-3373 isomers made using the compound 12 isomers with those of other ProTides known in the literature. As mentioned above, the stereochemistry of phosphate stereocentre is inverted during the process of the invention so the (Sp)-diastereoisomer of the compound of formula 12 will form the (Sp)-diastereoisomer of NUC-3373 and likewise the (R)-diastereoisomer of the compound of formula 12 will form the (R)-diastereoisomer of NUC-3373. The stereochemical assignment is supported by powder X-ray diffraction and differential scanning calorimetry that has been carried out on the two compound 12 isomers, but this is not in itself definitive.

Example 8—Formation of Sp and Rp Isomers of NUC-3373

3'-BOC protected FUDR 16 can be made according to the following scheme.

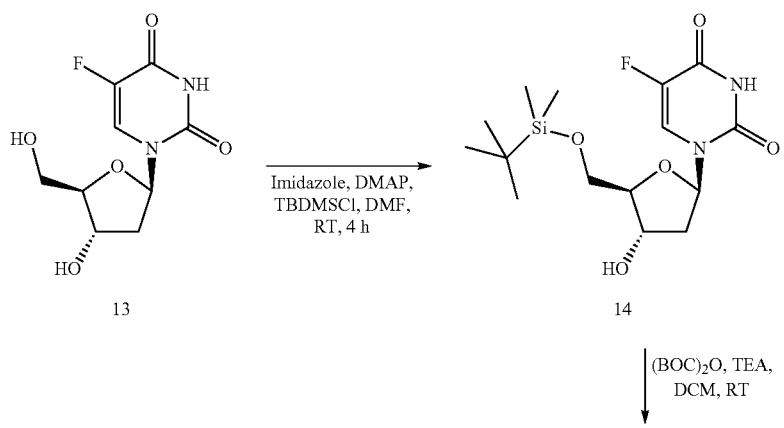

-continued

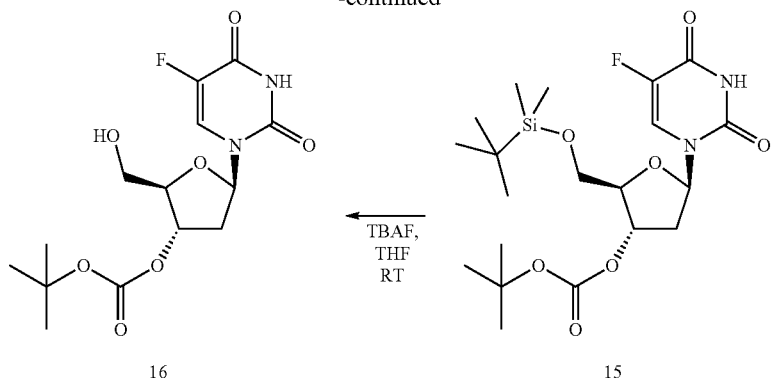

Compound 16 can then be coupled with a compound of formula IIa.

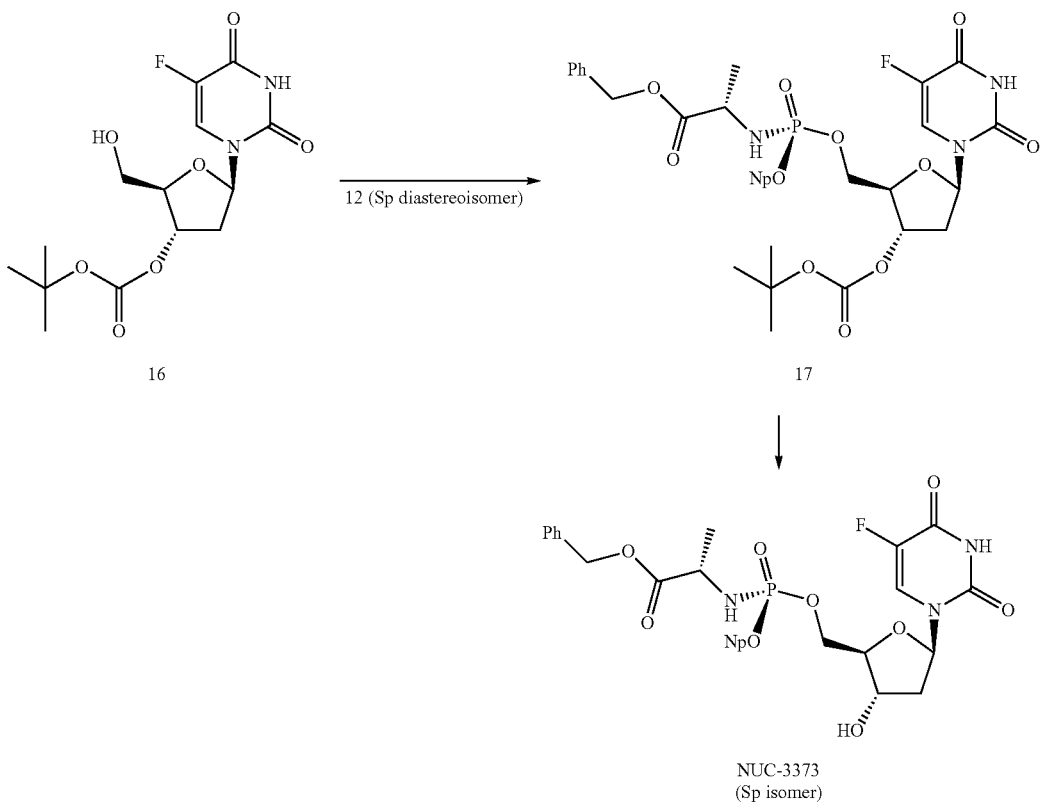

Compound 16 (1 g) and the Sp isomer of compound 12 (1.2 eq) were dissolved in THF (10 mL) and the mixture was cooled to 0° C. t-Butyl magnesium chloride (2.5 eq, 2.0 M in THF) was added to the mixture over 15 min. The mixture was warmed and stirred at 25° C. for 4 h. The mixture was cooled to 10° C. and sat. ammonium chloride solution (10 mL) was added. Ethyl acetate (10 mL) was added to the mixture and the organic layer was separated. The aqueous layer was extracted with ethyl acetate (5 mL). The combined organic layers were washed with deionised water (5 mL) followed by 20% sodium chloride solution (5 mL). The organic layers were dried over anhydrous sodium sulphate before being concentrated in vacuo to provide 2.16 g of compound 17 (100% crude yield).

Crude compound 17 (1 g) was dissolved in DCM (5 mL) and cooled to 10° C. TFA (2 mL) was added slowly to the mixture, maintaining the temperature at below 20° C. The mixture was warmed to 30° C. and the stirred for 6 h. The mixture was cooled to 10° C. and deionized water (5 mL) was added slowly, maintaining the temperature at below 20° C. After stirring for 10 min the organic layer was separated and the aqueous layer was extracted with DCM (5 mL). The combined organic layers were washed with deionised water (2×5 mL), 7% sodium bicarbonate solution (2×5 mL) and 20% sodium chloride solution (5 mL) before being dried with anhydrous sodium sulphate (1 w/w) and concentrated in vacuo. Crude compound was purified with column chromatography in ethyl acetate/DCM using silica gel (100-200 mesh). Pure compound was eluted in 50% Ethyl acetate/

DCM to 100% ethyl acetate. The combined pure fractions were concentrated in vacuo before the compound slurry was washed with cyclohexane (5 mL).

Results:
Weight of NUC-3373 (Sp isomer): 9.3 g
Overall yield: 70%
HPLC purity: 96.86%

$^1$H-NMR (500 MHz, MeOD): $\delta_H$ 8.16-8.14 (m, 1H, H—Ar), 7.90-7.80 (m, 1H, H—Ar), 7.72-7.70 (m, 2H, H—Ar), 7.54-7.49 (m, 3H, H—Ar, H-6), 7.43 (apparent t, 1H, J=8.0 Hz, H—Ar), 7.35-7.27 (m, 5H, H—Ar), 6.16-6.13 (m, 1H, H-1'), 5.11 (AB system, J=12.0 Hz, 2H, OCH$_2$Ph), 4.35-4.33 (m, 2H, 2×H-5'), 4.30-4.28 (m, 1H, H-3'), 4.14-4.08 (m, H, CHCH$_3$), 4.07-4.04 (m, 1H, H-4'), 2.14-2.09 (m, 1H, H-2'), 1.74-1.68 (m, 1H, H-2'), 1.35 (d, J=7.0 Hz, 3H, CHCH$_3$);

$^{13}$C-NMR (125 MHz, MeOD): $\delta_C$ 174.92 (d, $^3J_{C-P}$=3.75 Hz, C=O, ester), 159.37 (d, $^2J_{C-F}$=25.9 Hz, C=O, base), 150.54 (d, $^4J_{C-F}$=4.0 Hz, C=O, base), 147.99 (d, $^2J_{C-P}$=7.1 Hz, C—Ar, Naph), 141.75 (d, $^1J_{C-F}$=232.1 Hz, CF-base), 137.18, 136.29 (C—Ar), 129.59, 129.36, 128.90, 127.91 (CH—Ar), 127.83 (d, $^3J_{C-P}$=5.4 Hz, C—Ar, Naph), 127.59, 126.52, 126.50, 126.18 (CH—Ar), 125.54 (d, $^2J_{C-F}$=34.1 Hz, CH-base), 122.64 (CH—Ar), 116.29 (d, $^3J_{C-P}$=2.75 Hz, CH—Ar, Naph), 86.95 (C-1'), 86.67 (d, $^3J_{C-P}$=8.1 Hz, C-4'), 72.12 (C-3'), 68.05 (OCH$_2$Ph), 67.85 (d, $^2J_{C-P}$=5.3 Hz, C-5'), 51.96 (CHCH$_3$), 40.84 (C-2'), 20.52 (d, $^3J_{C-P}$=7.5 Hz, CHCH$_3$).

$^{31}$P-NMR (202 MHz, MeOD): $\delta_P$ 4.62;
$^{19}$F NMR (470 MHz, MeOD): $\delta_F$ –167.19;
(ES+) m/z: Found: (M+Na$^+$) 636.1520. C$_{29}$H$_{29}$N$_3$O$_9$FNaP required: (M$^+$), 613.15.

Reverse HPLC (Varian Pursuit XRs 5 C18, 150×4.6 mm) eluting with (H$_2$O/AcCN from 90/10 to 0/100) in 35 min., $t_R$ 16.61 min.

The Rp isomer of NUC-3373 can be accessed by performing the above process but starting with the Rp diastereomer of compound 12:

$^1$H-NMR (500 MHz, MeOD): $\delta_H$ 8.17-8.15 (m, 1H, H—Ar), 7.91-7.88 (m, 1H, H—Ar), 7.72-7.69 (m, 2H, H—Ar), 7.56-7.52 (m, 2H, H—Ar, H-6), 7.50-7.48 (m, 1H, H—Ar), 7.39 (apparent t, J=8.0 Hz, 1H, H—Ar), 7.35-7.28 (m, 5H, H—Ar), 6.16-6.09 (m, 1H, H-1'), 5.13 (s, 2H, OCH$_2$Ph), 4.35-4.25 (m, 3H, 2×H-5', H-3'), 4.14-4.08 (m, 1H, CHCH$_3$), 4.05-4.03 (m, 1H, H-4'), 2.15-2.10 (m, 1H, H-2'), 1.74-1.68 (m, 1H, H-2'), 1.36 (d, J=7.0 Hz, 3H, CHCH$_3$);

$^{13}$C-NMR (125 MHz, MeOD): $\delta_C$ 174.58 (d, $^3J_{C-P}$=5.0 Hz, C=O, ester), 159.38 (d, $^2J_{C-F}$=26.3 Hz, C=O), 150.48 (C=O base), 147.80 (d, $^2J_{C-P}$=6.5 Hz, C—Ar, Naph), 141.67 (d, $^1J_{C-F}$=232.5 Hz, CF-base), 137.15, 136.26 (C—Ar), 129.62, 129.40, 129.36, 128.96, 127.89 (CH—Ar), 127.84 (d, $^3J_{C-P}$=5.5 Hz, C—Ar, Naph), 127.59, 126.57, 126.55, 126.21 (CH—Ar), 125.61 (d, $^2J_{C-F}$=34.0 Hz, CH-base), 122.62 (CH—Ar), 116.55 (d, $^3J_{C-P}$=3.75 Hz, CH—Ar, Naph), 86.97 (C-1'), 86.66 (d, $^3J_{C-P}$=7.5 Hz, C-4'), 72.01 (C-3'), 68.07 (OCH$_2$Ph), 67.84 (d, $^2J_{C-P}$=5.0 Hz, C-5'), 51.83 (CHCH$_3$), 40.89 (C-2'), 20.42 (d, $^3J_{C-P}$=7.5 Hz, CHCH$_3$).

$^{31}$P-NMR (202 MHz, MeOD): $\delta_P$ 4.27;
$^{19}$F NMR (470 MHz, MeOD): $O_F$ –167.27;
(ES+) m/z: Found: (M+Na$^+$) 636.1520. C$_{29}$H$_{29}$N$_3$O$_9$FNaP required: (M$^+$), 613.15.

Reverse HPLC (Varian Pursuit XRs 5 C18, 150×4.6 mm) eluting with (H$_2$O/MeOH from 90/10 to 0/100) in 35 min., $t_R$ 16.03 min.

The stereochemistry (Rp vs Sp) of the two NUC-3373 isomers described above has been assigned tentatively on the basis of comparison of $^{31}$P chemical shift, $^1$H NMR spectra, and HPLC retention times with those of other ProTides known in the literature. The stereochemistry of compound 12 has been tentatively assigned based on which isomer of NUC-3373 that isomer of compound 12 forms.

Example 9—Formation of Sp and Rp Isomers of NUC-7738

2'-TBDMS protected 3'-deoxyadenosine 21 can be made according to the following scheme.

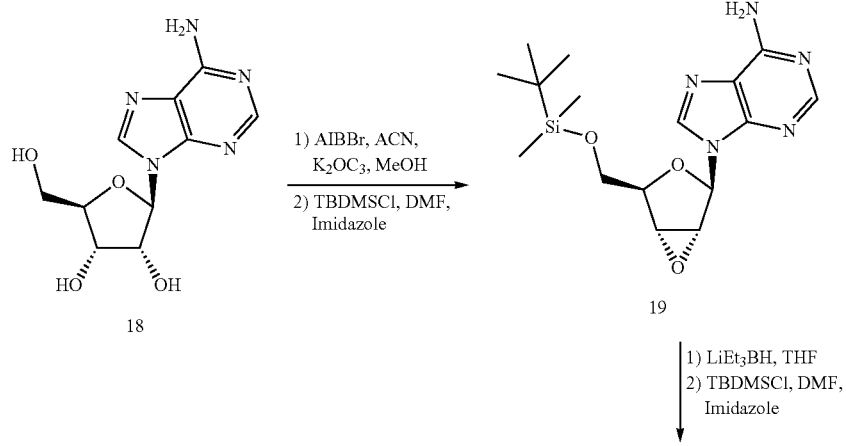

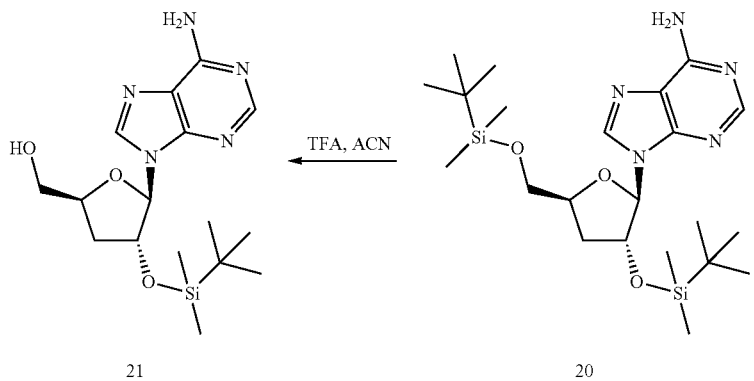
Compound 21 can then be coupled with a compound of formula IIb using the coupling process conditions described in Example 8. To form NUC-7738, the TBDMS group can be removed using TFA in THF.
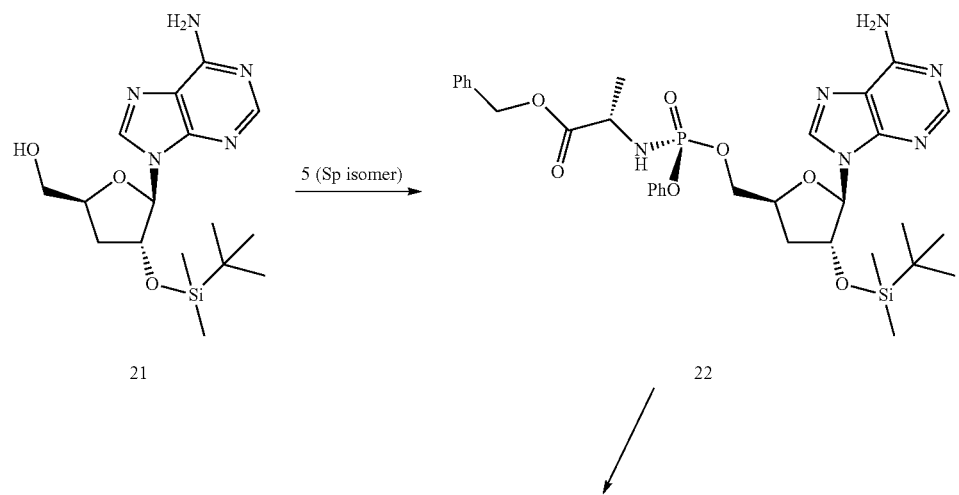
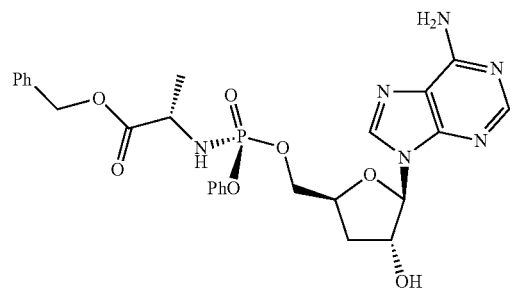
NUC-7738
Sp isomer

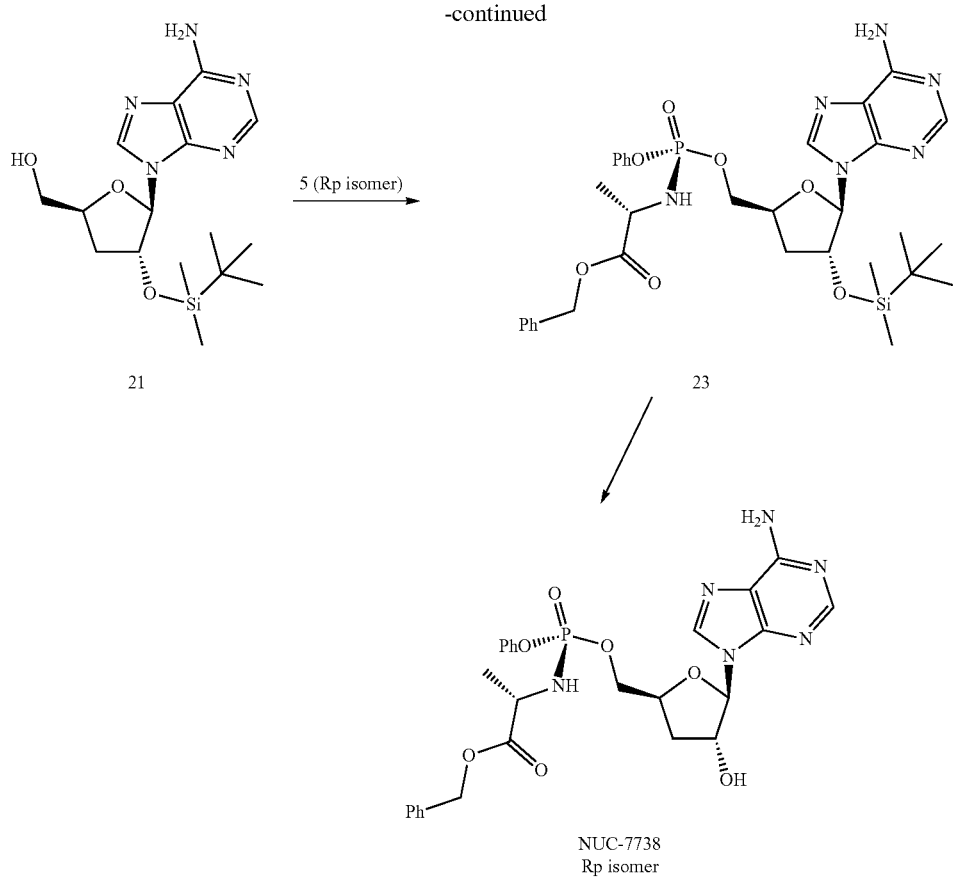

NUC-7738
Rp isomer

Adenosine (18) to Epoxide 19

One equivalent adenosine (18) was dissolved in 10 V acetonitrile and the mixture was cooled to 15° C. 3.0 molar equivalents acetoxy isobutyryl bromide was added slowly at 15° C. The mixture was warmed to room temperature and stirred for 8 hours. The reaction was quenched with sodium bicarbonate solution and extracted with ethyl acetate. The combined organic layers were washed with 5% sodium chloride solution and the organic layers were concentrated in vacuo.

The product was dissolved in 15 V methanol and 1 weight equivalent of potassium carbonate was added before stirring for 2 hours. The mixture was concentrated in vacuo and the product was washed with water before drying the product under vacuum at 60° C. to provide 2',3'-anhydro adenosine in a yield of 70-85%.

1 equivalent of 2',3'-anhydro adenosine and 1.6 equivalents imidazole were dissolved in 5V DMF. The mixture was cooled to 15° C. and 0.8 equivalents TBDMSCI was added. The mixture was stirred for 1 to 2 hours at 30° C. before a further 0.4 equivalents imidazole and 0.4 equivalents TBDMSCI were added. The mixture was stirred for a further 1 to 2 hours at 30° C. before water was added (5V). The mixture was extracted with ethyl acetate. The combined organic layers were sequentially washed with 7% sodium bicarbonate solution, water and 5% sodium chloride solution before being concentrated in vacuo. The product was washed with heptane before being dried under vacuum at 50° C. to obtain epoxide 19 in 75-90% yield.

Epoxide 19 to 5'-Silyl Cordycepin 21

1 Equivalent of epoxide 19 was dissolved in a mixture of DMSO (5V) and THF (5V). The mixture was cooled to 0° C. and the mixture was purged with nitrogen gas. 1M Lithium triethylborohydride (1 eq) in THF was added at 0(±5)° C. over a period of 1-2 hours. The mixture was stirred at 0° C. for 30 minutes, warmed to 30° C. and stirred for 2 hours before methanol (10 V) was slowly added at 5° C. 10V 10% sodium hydroxide and then 10V 10% hydrogen peroxide solution were added drop wise at 5° C. The mixture was extracted with ethyl acetate and the combined organic layers were washed sequentially with 10% sodium metabisulfite solution, water in to reactor, 7% sodium bicarbonate solution and 10% sodium chloride solution before being concentrated in vacuo. The product was washed with heptane before being dried under vacuum at 50° C. to obtain 2'-silyl cordycepin in 70-100% yield.

The 2'-silyl cordycepin, 2.5 equivalents imidazole and 0.15 equivalents DMAP were dissolved in 5V DMF. The mixture was cooled to 15° C. before 2.5 equivalents TBDMSCI were added portionwise. The reaction was stirred for 4 hours at 30° C. before being cooled to 15° C. 10V water was added and the mixture was extracted with ethyl acetate. The organic layers were washed with 7% sodium bicarbonate solution, water and 5% sodium chloride before being concentrated in vacuo.

The mixture was dissolved in 8V and 2V water was added before the mixture was cooled to 0° C. 2.5 Eq. trifluoroacetic acid was added to the reaction mixture at 0° C. over a period of 30-60 min. The mixture was warmed to 10° C. and stirred for 4 to 6 hours at 10° C. Water was added and the mixture was extracted with ethyl acetate. The combined organic layers were washed with 7% sodium bicarbonate solution, water (twice) and 5% sodium chloride solution before being concentrated in vacuo. The product was washed with heptane and dried under vacuum to provide 5'-silyl cordycepin 21 in 40-70% yield.

5'-Silyl Cordycepin 21 to $S_p$-NUC-7738

5'-silyl cordycepin 21 was dissolved in 10 V THF and cooled to 0° C. 2.0M t-BuMgCl (2.5 equivalents) was added and the mixture was stirred for 15 min. The $S_p$ isomer of compound 5 (2.5 eq) was dissolved in 5 V THF and was added to the reaction at 0° C. The mixture was stirred at 0° C. for 15 min before being warmed to 25° C. and stirred for a further 2 hours. The reaction was quenched into 10% ammonium chloride solution (10 vol) and extracted with ethyl acetate. The combined organic layers were washed with water and 10% brine solution before being concentrated in vacuo.

The product was dissolved in THF (10V) before being cooled to 0° C. A 10 V TFA and water (1:1) mixture was added to the reaction over a period of 30 min before the mixture was stirred for 45 min, warmed to 30° C. and stirred for a further 16 h. The reaction was quenched in to 7% $NaHCO_3$ solution (90 V) at 0° C. before being extracted with ethyl acetate. The combined organic layers were washed with water, 7% sodium bicarbonate solution and 10% brine solution before being concentrated in vacuo.

The product was purified by column chromatography by using silica gel (100-200 mesh), the column was eluted by 2 to 10% MeOH in DCM to provide $S_p$-NUC-7738 in 40% yield. The HPLC purity of the product was 99.50% and Chiral HPLC showed the $S_p$ isomer to be present in 99.90% and the $R_p$ isomer to be present in 0.10%.

The same procedure can be carried out to provide $R_p$-NUC-7738.

Rp-NUC-7738:

$^1$H NMR (500 MHz, $CDCl_3$) $\delta_H$ 8.26 (s, 1H, H8), 8.22 (s, 1H, H2), 7.37-7.25 (m, 7H, Ar), 7.22-7.12 (m, 3H, Ar), 6.01 (d, J=1.5 Hz, 1H, H1'), 5.12 (AB q, $J_{AB}$=12.0 Hz, $\Delta\delta_{AB}$=0.04, 2H, $CH_2$Ph), 4.74-4.70 (m, 1H, H2'), 4.69-4.62 (m, 1H, H4'), 4.44-4.38 (m, 1H, H5'), 4.28-4.21 (m, 1H, H5'), 3.99-3.90 (m, 1H, $CHCH_3$ L-Ala), 2.35-2.27 (m, 1H, H3'), 2.09-2.02 (m, 1H, H3'), 1.29 (d, J=7.0 Hz, 3H, $CHCH_3$ L-Ala).

$^{31}$P NMR (202 MHz, $CD_3OD$) Op 3.91.

MS (ES$^+$) m/z found 569.2 [M+H$^+$], 591.2 [M+Na$^+$], 1159.4 [2M+Na$^+$] $C_{26}H_{29}N_6O_7P$ required m/z 568.2 [M].

HPLC Reverse-phase HPLC (Varian Pursuit XRs 5 C18, 150×4.6 mm) eluting with $H_2O/CH_3CN$ from 90/10 to 0/100 in 30 minutes, F: 1 mL/min, λ=200 nm, shows one peak with $t_R$ 14.02 min.

Sp-NUC-7738:

$^1$H NMR (500 MHz, $CDCl_3$) $\delta_H$ 8.24 (s, 1H, H8), 8.22 (s, 1H, H2), 7.36-7.26 (m, 7H, Ar), 7.22-7.13 (m, 3H, Ar), 6.01 (d, J=1.5 Hz, 1H, H1'), 5.08 (AB q, $J_{AB}$=12.0 Hz, $\Delta\delta_{AB}$=0.01, 2H, $CH_2$Ph), 4.70-4.67 (m, 1H, H2'), 4.66-4.60 (m, 1H, H4'), 4.41-4.35 (m, 1H, H5'), 4.26-4.19 (m, 1H, H5'), 4.02-3.94 (m, 1H, $CHCH_3$ L-Ala), 2.36-2.27 (m, 1H, H3'), 2.08-2.01 (m, 1H, H3'), 1.34-1.30 (m, 3H, $CHCH_3$ L-Ala).

$^{31}$P NMR (202 MHz, $CD_3OD$) $\delta_P$ 3.73. MS (ES$^+$) m/z found 569.2 [M+H$^+$], 591.2 [M+Na$^+$], 1159.4 [2M+Na$^+$] $C_{26}H_{29}N_6O_7P$ required m/z 568.2 [M].

HPLC Reverse-phase HPLC (Varian Pursuit XRs 5 C18, 150×4.6 mm) eluting with $H_2O/CH_3CN$ from 90/10 to 0/100 in 30 minutes, F: 1 mL/min, λ=200 nm, shows one peak with $t_R$ 14.26 min.

The stereochemistry ($R_p$ vs $S_p$) of the two NUC-7738 isomers described above has been confirmed by conventional X-ray crystallographic analysis.

Example 10—Formation of NUC-9701

Dimethyl acetal 25 of 8-chloro-adenosine 24 can be made according to the following scheme (also described in WO2017/207989).

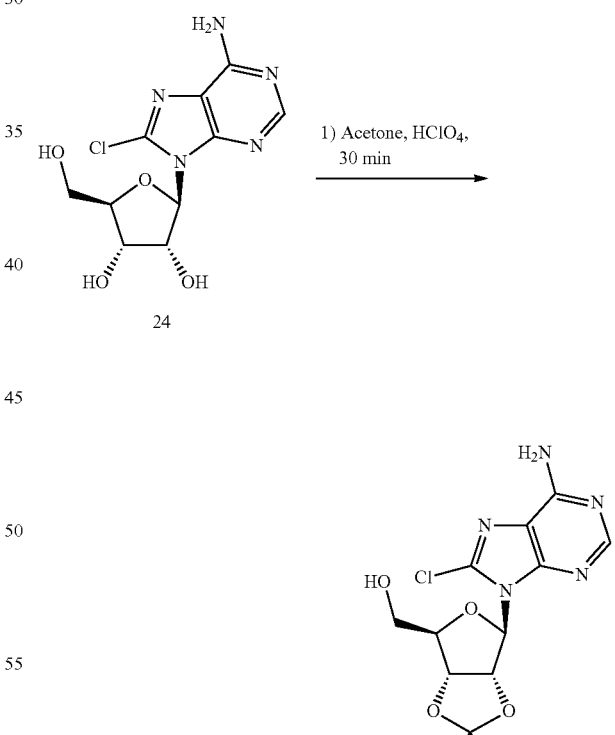

Compound 25 can then be coupled with a compound of formula IIa using the coupling process conditions described in Example 8. To form NUC-9701, dimethyl acetal can be removed using 1:1 TFA: water at 0° C. for 5 h.

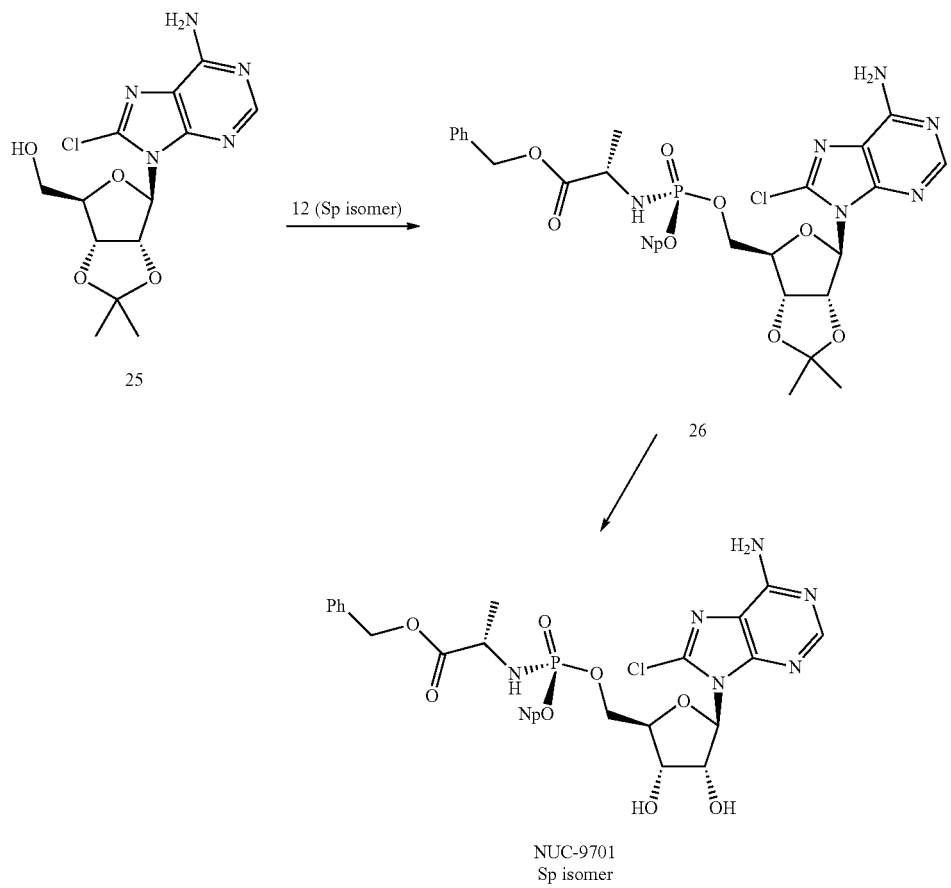

Compound 25 (30 g; 1 equivalent) and the desired isomer of compound 12 (58.08 g; 1.2 equivalents) were dissolved in 300 ml (10 V) of THF. The mixture was cooled to 0° C. before t-butyl magnesium chloride (76.8 ml of 2.0 M in THF; 1.75 equivalents) was added slowly, maintaining the temperature at 0° C., and the mixture was stirred for 4 hours. 300 mL (10V) of 10% Ammonium chloride solution was added to the reaction mixture, maintaining the temperature at below 15° C. The mixture was extracted with ethyl acetate and the combined organic layers were washed with 7% sodium bicarbonate solution (twice), water (twice) and 20% sodium chloride before being dried with anhydrous sodium sulphate and filtered. The ethyl acetate was removed in vacuo.

To the resultant product as added 600 ml (20V) of 60% formic acid in water and the reaction was stirred for 65-70 h at 25° C. before ethyl acetate (600 mL; 20V) was added slowly. 600 ml (20 V) of 20% sodium chloride solution was added and the layers were separated. The aqueous layer was extracted with ethyl acetate before 600 ml (20 V) 10% Ammonia solution was added dropwise to the combined organic layers and the layers were separated. The organic layer was washed with water (three times) and 20% sodium chloride solution, dried with 30 g (1 w/w) of anhydrous sodium sulphate and filtered before being concentrated in vacuo. The crude product was purified by column chromatography to provide 20-45 g NUC-9701.

Sp-NUC-9701:
$^1$H-NMR (500 MHz; MeOD-d4): $\delta_H$ 8.07 (1H, d J=8.5 Hz, H-Napht), 8.05 (1H, s, 2-H), 7.87 (1H, d J=8.5 Hz, H-Napht), 7.67 (1H, d J=8.5 Hz, H-Napht) 7.54-7.48 (2H, m, H-Napht), 7.41-7.30 (1H, m, H-Napht), 7.36-7.33 (1H, m, H-Napht), 7.26-7.22 (5H, m, —CH$_2$Ph), 6.03 (1H, d J=5.0 Hz, H-1'), 5.33 (1H, t J=5.0 Hz, H-2'), 5.01, 4.98 (AB, J$_{AB}$=12.3 Hz, CH$_2$Ph), 4.65 (1H t J=5.5 Hz, H-3'), 4.49-4.45 (1H, m, H$_a$-5'), 4.41-4.36 (1H, m, H$_b$-5'), 4.22-4.20 (1H, m, H-4'), 3.94-3.90 (1H, m, —CHCH$_3$), 1.17 (1H, d J=7.0 Hz, CH$_3$).

$^{31}$P NMR (202 MHz, MeOD-d4): $\delta_P$ 3.93 (1P, s).

Reverse-phase HPLC, eluting with H$_2$O/CH$_3$CN from 90/10 to 0/100 in 30 min; 1 mL/min, λ=254 nm, showed a peak with t$_R$=16.43 min Rp-NUC-9701:
$^1$H-NMR (500 MHz; MeOD-d4): $\delta_H$ 8.10 (1H, s, H-2), 8.08 (1H, d J=8.5 Hz, H-Napht), 7.87 (1H, d J=8.5 Hz, H-Napht), 7.67 (1H, d J=8.5 Hz, H-Napht), 7.53-7.50 (1H, m, H-Napht), 7.48-7.44 (1H, m, H-Napht), 7.40-7.38 (1H, m, H-Napht), 7.33-7.27 (6H, m, H-Napht and —CH$_2$Ph), 6.02 (1H, d J=5.0 Hz, H-1'), 5.28 (1H, t J=5.0 Hz, H-2'), 5.04, 5.02 (AB, J$_{AB}$=12.2 Hz, CH$_2$Ph), 4.63 (1H t J=5.5 Hz, H-3'), 4.48-4.46 (1H, m, H$_a$-5'), 4.38-4.35 (1H, m, H$_b$-5'), 4.23-4.20 (1H, m, H-4'), 4.05-4.01 (1H, m, —CHCH$_3$), 1.17 (1H, d J=7.0 Hz, CH$_3$).

$^{31}$P NMR (202 MHz, MeOD-d4): $\delta_P$ 3.83 (1P, s).

Reverse-phase HPLC, eluting with H$_2$O/CH$_3$CN from 90/10 to 0/100 in 30 min; 1 mL/min, λ=254 nm, showed a peak with t$_R$=16.59 min The stereochemistry (R$_p$ vs S$_p$) of the two NUC-9701 isomers described above has been assigned tentatively on the basis of comparison of $^{31}$P chemical shift, 1H NMR spectra, and HPLC retention times with those of other ProTides known in the literature.

We claim:

1. A process for the diastereoisomeric enrichment of a compound of Formula IIa wherein $R^1$ is selected from the group consisting of halogen, trifluoromethyl, cyano and nitro and a is an integer from 1 to 5:

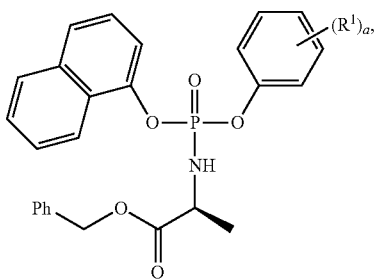

Formula IIa the process comprising steps a), b), and c), wherein the X-diastereoisomer of the compound of Formula IIa is the $(S_p)$-diastereoisomer and the Y-diastereoisomer of the compound of Formula IIa is the $(R_p)$-diastereoisomer, except when the $OPh(R^1)_n$ leaving group has lower priority assignment under the Cahn-Ingold-Prelog rules than the naphthyloxy group, in which case the X-diastereoisomer of the compound of Formula IIa is the $(R_p)$-diastereoisomer and the Y-diastereoisomer of the compound of Formula IIa is the $(S_p)$-diastereoisomer:

a) suspending or dissolving the Y-diastereoisomer of the compound of Formula IIa or a mixture of the Y- and X-diastereoisomers of the compound of Formula IIa in a solvent (S2), wherein S2 is a mixture of hexane or heptane and methyl tert butyl ether;

b) treating the solution or suspension with an organic amine base for 24 hours to 100 hours at a temperature from 10° C. to 35° C. to obtain the X-diastereoisomer having a diastereoisomeric purity of greater than 95%, wherein B2 is an organic amine base; and c) isolating the X-diastereoisomer of Formula IIa.

2. The process of claim 1, wherein B2 is a trialkylamine.

3. The process of claim 2, wherein B2 is triethylamine.

4. The process of claim 2, wherein B2 is diisopropylethyl amine.

5. The process of claim 1, wherein S2 is a mixture of hexane and methyl tert-butyl ether.

6. The process of claim 1, wherein S2 is a mixture of heptane and methyl tert-butyl ether.

7. The process of claim 1 wherein the solution or suspension of step (b) is stirred for at least 60 hours.

8. The process of claim 1, wherein the solution or suspension of step (b) is stirred for at least 72 hours.

9. The process of claim 1, wherein $R^1$ is halogen.

10. The process of claim 9, wherein halogen is fluorine.

11. The process of claim 9, wherein halogen is chlorine.

12. The process of claim 9, wherein halogen is bromine.

13. The process of claim 9, wherein halogen is iodine.

14. The process of claim 9, wherein a is 1.

15. The process of claim 9, wherein a is 2.

16. The process of claim 9, wherein a is 5.

17. The process of claim 1, wherein $R^1$ is fluorine and a is 5.

18. The process of claim 1, wherein $R^1$ is trifluoromethyl.

19. The process of claim 1, wherein $R^1$ is cyano.

20. The process of claim 1, wherein $R^1$ is nitro.

21. The process of claim 20, wherein a is 1.

22. The process of claim 20, wherein a is 2.

23. The process of claim 1, wherein $R^1$ is halogen and a is 1, 2, or 5.

24. The process of claim 1, wherein $R^1$ is nitro and a is 1 or 2.

25. The process of claim 1, wherein $R^1$ is cyano and a is 1.

26. The process of claim 1, wherein $R^1$ is trifluoromethyl and a is 1.

* * * * *